United States Patent
Lloyd et al.

(10) Patent No.: US 9,296,716 B2
(45) Date of Patent: Mar. 29, 2016

(54) ANDROGEN RECEPTOR LIGANDS

(71) Applicants: David George Lloyd, Malahide (IE); Darren Fayne, Dublin (IE); Mary Jane Meegan, Ballinteer (IE); Miriam Carr, Perrystown (IE); Gemma Karena Kinsella, Maynooth (IE); Laura Caboni, Blackrock (IE); Wiliam Nicholas Jagoe, Sandymount (IE); Billy Egan, Bray (IE); Fernando Blanco, Valencia (ES); D. Clive Williams, Dalkey (IE)

(72) Inventors: David George Lloyd, Malahide (IE); Darren Fayne, Dublin (IE); Mary Jane Meegan, Ballinteer (IE); Miriam Carr, Perrystown (IE); Gemma Karena Kinsella, Maynooth (IE); Laura Caboni, Blackrock (IE); Wiliam Nicholas Jagoe, Sandymount (IE); Billy Egan, Bray (IE); Fernando Blanco, Valencia (ES); D. Clive Williams, Dalkey (IE)

(73) Assignee: THE PROVOST, FELLOWS, FOUNDATION SCHOLARS, & THE OTHER MEMBERS OF BOARD, OF THE COLLEGE OF THE HOLY AND UNDIV. TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 14/360,081

(22) PCT Filed: Nov. 23, 2012

(86) PCT No.: PCT/EP2012/073525
§ 371 (c)(1),
(2) Date: May 22, 2014

(87) PCT Pub. No.: WO2013/076275
PCT Pub. Date: May 30, 2013

(65) Prior Publication Data
US 2014/0357682 A1    Dec. 4, 2014

(30) Foreign Application Priority Data

Nov. 23, 2011 (EP) .................................. 11190354

(51) Int. Cl.
| | | |
|---|---|---|
| C07D 307/91 | (2006.01) |
| C07D 209/56 | (2006.01) |
| C07D 307/92 | (2006.01) |
| A61K 31/166 | (2006.01) |
| A61K 31/175 | (2006.01) |
| A61K 31/343 | (2006.01) |
| C07C 251/86 | (2006.01) |
| C07D 213/56 | (2006.01) |
| C07D 307/54 | (2006.01) |

(52) U.S. Cl.
CPC ............ *C07D 307/92* (2013.01); *A61K 31/166* (2013.01); *A61K 31/175* (2013.01); *A61K 31/343* (2013.01); *C07C 251/86* (2013.01); *C07D 213/56* (2013.01); *C07D 307/54* (2013.01)

(58) Field of Classification Search
CPC ... C07D 307/91; C07D 333/74; C07D 209/60
USPC ..................................... 549/460, 48; 548/427
See application file for complete search history.

(56) References Cited

PUBLICATIONS

Cabone et al J. Med. Chem. vol. 55 No. 4 pp. 1635-1644 (2012).*

* cited by examiner

*Primary Examiner* — Andrew D Kosar
*Assistant Examiner* — Raymond Covington
(74) *Attorney, Agent, or Firm* — Scully Scott Murphy and Presser; Edward Grolz

(57) ABSTRACT

Non ligand binding pocket antagonists for the human androgen receptor. The androgen receptor (AR) is a member of the Nuclear Receptor (NR) family and its role is to modulate the biological effects of the endogenous androgens, testosterone (tes) and dihydrotestosterone (DHT). Synthetic androgens and anti-androgens have therapeutic value in the treatment of various androgen dependent conditions, from regulation of male fertility to prostate cancer. Current treatment of prostate cancer (PCa) typically involves administration of 'classical' antiandrogens, competitive inhibitors of natural AR ligands, DHT and tes, for the ligand binding pocket (LBP) in the C-terminal ligand binding domain (LBD) of the AR. However, prolonged LBP-targeting can often lead to androgen resistance and alternative therapies and therapeutic strategies are urgently required. Disclosed herein are a class of non-steroidal, small molecule AR antagonists which inhibit the transcriptional activity of the AR by non LBP-mediated modulation. The novel class reported demonstrates full ('true') antagonism in AR with low micromolar potency, high selectivity over both the Estrogen Receptors alpha and beta (ERα and ERβ) and the Glucocorticoid Receptor (GR) and only micromolar partial antagonism in the Progesterone Receptor (PR). Data provide compelling evidence for such non-LBP intervention as an alternative approach to classical PCa therapy. (Formula I).

(I)

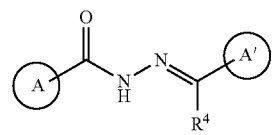

18 Claims, 18 Drawing Sheets

ANDROGEN RECEPTOR LIGANDS

FIELD OF THE INVENTION

The present invention provides for a novel class of nuclear receptor, small molecule ligands. In particular, the molecules may find applicability as antagonists of the androgen receptor, and in particular non ligand binding pocket (non-LBP) antagonists of the androgen receptor. The molecules may find utility in the treatment of conditions mediated by malfunction of the androgen receptor, for example prostate cancer, and in particular Castration Resistant Prostate Cancer (CRPC). The invention further relates to in silico methods for identifying ligands of the androgen receptor.

BACKGROUND TO THE INVENTION

Nuclear receptors (NRs) represent the largest family of ligand-dependent eukaryotic transcription factors transforming extra- and intracellular signals into cellular responses by triggering the transcription of target genes. The androgen receptor (AR) is a member of the NR family and its role is to modulate the biological effects of the endogenous androgens, testosterone (tes) and dihydrotestosterone (DHT). The AR plays many roles during male foetal and pubertal development as well as secondary sexual characteristics such as muscle and bone mass, strength, fat distribution and spermatogenesis. Androgen-dependent cells are dependent on activation of the androgen receptor (AR) for cell growth. Under normal circumstances, androgen natural hormones (tes and DHT) bind to the ligand binding pocket (LBP) placed at ligand-binding domain of the AR. The AR, in dimeric form, is then transferred into the nucleus, where it binds to androgen response elements (AREs). Nuclear co-activators and co-suppressors also bind to this complex, modulating the degree of transcription and cellular activation.

Androgens are required for the maintenance of normal sexual activity in adulthood and for enhancing muscle growth and lean body mass in adolescents and adults. Androgen receptor (AR) ligands with tissue selectivity have potential for treating muscle wasting, hypogonadism of aging, osteoporosis, female sexual dysfunction, and other indications. Similarly, excessive androgen concentrations can lead to a number of clinical pathologies.

Male pattern hair loss is the most common cause of balding. The pathogenesis involves androgen, and in particular dihydrotestosterone, binding to androgen receptors in the dermal papilla of sensitive hair follicles. Androgens also play pathogenic roles in acne mainly through stimulation of lipogenesis in sebaceous glands in a complex manner. Additionally, hirsutism is characterised by excessive coarse terminal hairs in a male-like pattern and is due to increased androgen production or increased sensitivity of androgen receptors. Polycystic ovary syndrome (PCOS) is by far the commonest cause of hirsutism.

Synthetic androgens and anti-androgens have therapeutic value in the treatment of various androgen dependent conditions, from regulation of male fertility to prostate cancer (PCa). The traditional ligand focussed treatment regime for PCa is reliant on the blockage of tes and DHT by AR LBP antagonists binding and thereby not allowing the activation of AR.

Anti-androgens traditionally act by two primary mechanisms: inhibition of hormone (androgens) binding to the androgen receptor, so-called androgen ablation therapy (AAT), and inhibition of androgen-independent activation of the receptor. The latter mechanism occurs via several pathways, including inhibiting nuclear co-activators, activating co-suppressors, and inhibiting transcription of a variety of androgen regulated genes.

A number of LBP anti-androgens have been demonstrated clinically as an effective therapy for the treatment of prostate cancer, including cyproterone acetate, flutamide and bicalutamide. These compounds compete with tes and its powerful metabolite, dihydrotestosterone (DHT) for binding to androgen receptors in the prostate gland. By doing so, it prevents them from stimulating the prostate cancer cells to grow. Flutamide is an anti-androgen drug which was primarily used to treat prostate cancer. Flutamide may also be used to treat excess androgen levels in women. Bicalutamide is an oral non-steroid al anti-androgen for prostate cancer, which has largely replaced flutamide due to a better side-effect profile. Nilutamide is an antiandrogen medication used in the treatment of advanced stage prostate cancer. Nilutamide blocks the AR preventing its interaction with testosterone. Because most prostate cancer cells rely on the stimulation of the androgen receptor for growth and survival, nilutamide can prolong life in men with prostate cancer.

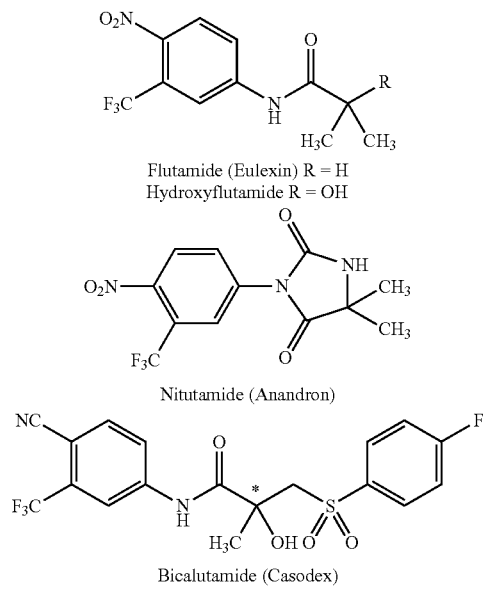

Flutamide (Eulexin) R = H
Hydroxyflutamide R = OH

Nitutamide (Anandron)

Bicalutamide (Casodex)

These anti-androgens exhibit good efficacy in many cases, however, prolonged LBP-targeting can often lead to androgen resistance. Recurrence occurs after a short period of response as they have partial agonist activities at high concentrations in vitro.

The structure of the NRs is extensively documented, and in general NRs share the following common organisation: a variable amino-terminal activation function domain (AF-1), a highly conserved DNA-binding domain (DBD), a hinge region which contains the nuclear localisation signal, a conserved C-terminal ligand-binding domain (LBD) comprising a 12 helical structure that encloses a central ligand binding pocket (LBP) and a second activation function domain (AF-2) which is located at the carboxy-terminal end of the LBD and which mediates ligand-dependent transactivation.

Traditional nuclear receptors (NRs) drug discovery has been focused at the heart of the C-terminal 12-alpha helical ligand binding domain (LBD), the ligand binding pocket (LBP), where natural ligands bind and drive conformational changes that indirectly modulate protein-protein interactions at non-LBP docking sites that are necessary for NR transcriptional activity. In response to the ligand binding to the LBP, the hydrophobic surface activation function 2 (AF-2), involving helices 3, 4, 5 and 12, is generated for the recruitment of coactivator proteins that ultimately have consequences in NR functional activity. In a recent work, an additional secondary function site called binding function 3 (BF-3) has been reported on the surface of the AR that could also play a relevant role in the allosteric modulation of the AF-2 (Estebanez-Perpina E, Arnold L A, Nguyen P, Rodrigues E D, Mar E, et al. (2007) A surface on the androgen receptor that allosterically regulates coactivator binding. *Proc. Natl. Acad. Sci. USA* 104:16074-16079). Alternative AR targeting through this regulatory interfaces (AF-2 and BF-3) has gained a great deal of attention over the past decade. The need of such approaches arises by the limitation of the currently marketed LBP-acting antiandrogens regarding their applications, especially in. for example, castrate resistant prostate cancer.

Notwithstanding the state of the art, novel anti-androgenic agents that exhibit no agonistic activity, so called "AR pure antagonists" are strived for. Inhibition of the transcriptional activity of the NRs by directly blocking critical receptor: coactivator interactions provides an attractive opportunity to find non-steroidal, small molecules that are tissue-selective and elicit the desired activity with reduced side effects, whilst at the same time exhibiting no partial agonist behaviour.

SUMMARY OF THE INVENTION

Disclosed herein are a class of non-steroidal, small molecule AR antagonists which inhibit the transcriptional activity of the AR by alternative non LBP-mediated modulation. Advantageously, the compounds have the potential to act in a tissue-selective manner with reduced side effects, whilst at the same time exhibiting no partial agonist behaviour. The compounds of the present invention may be pure AR antagonists or true non ligand binding pocket anti-androgens.

Accordingly, in a first aspect the present invention provides for a compound of the general formula (I), a tautomer thereof, a pharmaceutically acceptable salt thereof, or a solvate thereof for use in the treatment of a condition responsive to antagonism of the androgen receptor:

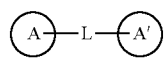
(I)

wherein:

A and A' are the same or different and may be independently selected from the group consisting of $C_5$-$C_{20}$ aryl, $C_3$-$C_{20}$ heteroaryl, $C_5$-$C_{20}$ aryl fused with $C_3$-$C_{20}$ cycloaliphatic or $C_2$-$C_{20}$ heterocycloaliphatic, $C_3$-$C_{20}$ heteroaryl fused with $C_3$-$C_{20}$ cycloaliphatic or $C_2$-$C_{20}$ heterocycloaliphatic, and combinations thereof, optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, CH$_2$F, CHF$_2$, CF$_3$, C≡N, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)R$^1$, N(R$^1$)C(=O)R$^2$, N(H)C(=O)OR$^1$, N(R$^1$)C(=O)OR$^2$, N(H)C(=O)NH$_2$, N(R$^1$)C(=O)NH$_2$, N(H)C(=O)NHR$^1$, N(R$^1$)C(=O)NHR$^2$, N(H)C(=O)NR$^1$R$^2$, N(R$^1$)C(=O)NR$^2$R$^3$, NO$_2$, SH, SR$^1$, S(=O)R$^1$, S(=O)$_2$R$^1$, SO$_3$H, OP(O)(OH)(OH), OP(O)(OH)(OR$^1$), OP(O)(OR$^1$)(OR$^2$), Cl, Br, F, and I;

L is an unsaturated moiety selected from the group consisting of $C_5$-$C_{20}$ aryl, $C_3$-$C_{20}$ heteroaryl, $C_3$-$C_{20}$ unsaturated aliphatic, $C_3$-$C_{20}$ unsaturated cycloaliphatic, $C_3$-$C_{20}$ unsaturated heteroaliphatic, $C_3$-$C_{20}$ unsaturated heterocycloaliphatic, optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, CH$_2$F, CHF$_2$, CF$_3$, C≡N, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)R$^1$, N(R$^1$)C(=O)R$^2$, N(H)C(=O)OR$^1$, N(R$^1$)C(=O)OR$^2$, N(H)C(=O)NH$_2$, N(R$^1$)C(=O)NH$_2$, N(H)C(=O)NHR$^1$, N(R$^1$)C(=O)NHR$^2$, N(H)C(=O)NR$^1$R$^2$, N(R$^1$)C(=O)NR$^2$R$^3$, NO$_2$, SH, SR$^1$, S(=O)R$^1$, S(=O)$_2$R$^1$, SO$_3$H, OP(O)(OH)(OH), OP(O)(OH)(OR$^1$), OP(O)(OR$^1$)(OR$^2$), Cl, Br, F, and I; and R$^1$, R$^2$ and R$^3$ are the same or different and may be independently selected from the group consisting of $C_1$-$C_{20}$ aliphatic, $C_3$-$C_{20}$ cycloaliphatic and combinations thereof.

The compounds of the present invention may be found or isolated in the form of prodrugs, tautomers, esters, salts, hydrates or solvates—all of which are embraced by the present invention.

With reference to the compound of the present invention L may comprise a moiety selected from the group consisting of hydrazidyl, oxadiazolyl, furyl, thienyl, pyrrolyl, pyridinyl, pyrazinyl, 1,4-dihydropyrazinyl, 1,2,3,4-tetrahydropyrazinyl, pyrimidinyl, pyridazinyl, 1,3-benzodioxolyl, 1,4-benzodioxanyl, 3,4-dihydro-2H-1,5-benzodioxepinyl, 2,3-dihydrobenzofuranyl, 2,3-dihydrobenzofuranyl, benzofuranyl, benzothiophenyl, benzothiophen-3-yl group, benzothiophen-4-yl group, benzothiophenyl, quinoxalinyl, indolyl, isoindolyl, isobenzofuranyl, chromenyl, imidazolyl, pyrazolyl, thiazolyl, oxazolyl, isoxazolyl, pyrrolidinyl, benzoimidazolyl, benzothiazolyl, benzoxazolyl, quinolinyl, isoquinolinyl, 1,3,4-thiadiazolyl, morpholino, triazolyl, tetrazolyl, indolinyl, 1,2,3,4-tetrahydroquinolinyl, 1,2,3,4-tetrahydroisoquinolinyl, and combinations thereof.

In one embodiment, the unsaturated moiety L may form a conjugated system with A and A'. As used herein, a conjugated system refers to a series of connected atomic p-orbitals with delocalized electrons. With reference to the compounds of the present invention L preferably comprises a hydrazidyl moiety.

Accordingly, in a preferred embodiment, the compound of the present invention may be of the general formula (II), wherein L comprises a hydrazidyl moiety:

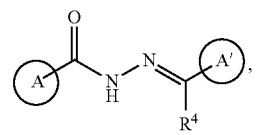
(II)

and wherein: A and A' are the same or different and may be independently selected from the group consisting of $C_5$-$C_{20}$ aryl, $C_3$-$C_{20}$ heteroaryl, $C_5$-$C_{20}$ aryl fused with $C_3$-$C_{20}$ cycloaliphatic or $C_2$-$C_{20}$ heterocycloaliphatic, $C_3$-$C_{20}$ heteroaryl fused with $C_3$-$C_{20}$ cycloaliphatic or $C_2$-$C_{20}$ heterocycloaliphatic, and combinations thereof, optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, CH$_2$F, CHF$_2$, CF$_3$, C≡N, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)

$R^1$, $N(R^1)C(=O)R^2$, $N(H)C(=O)OR^1$, $N(R^1)C(=O)OR^2$, $N(H)C(=O)NH_2$, $N(R^1)C(=O)NH_2$, $N(H)C(=O)NHR^1$, $N(R^1)C(=O)NHR^2$, $N(H)C(=O)NR^1R^2$, $N(R^1)C(=O)NR^2R^3$, $NO_2$, SH, $SR^1$, $S(=O)R^1$, $S(=O)_2R^1$, $SO_3H$, $OP(O)(OH)(OH)$, $OP(O)(OH)(OR^1)$, $OP(O)(OR^1)(OR^2)$, Cl, Br, F, and I; wherein $R^1$, $R^2$ and $R^3$ are the same or different and may be independently selected from the group consisting of $C_1$-$C_{20}$ aliphatic, $C_3$-$C_{20}$ cycloaliphatic and combinations thereof; and $R^4$ is selected from the group consisting of —H, $C_1$-$C_5$ alkyl, $C_3$-$C_6$ cycloalkyl, $C_5$-$C_{10}$ aryl, and $C_3$-$C_{10}$ heteroaryl.

In a preferred embodiment, $R^4$ is $C_1$-$C_5$ alkyl, for example methyl (Me). In one embodiment, when $R^4$ is Me, A' is 1,3-indandionyl or phthalimidyl.

With reference to the compound for the treatment of a condition responsive to antagonism of the androgen receptor of the present invention, a preferred compound has general formula (I), or is a tautomer thereof, a pharmaceutically acceptable salt thereof, or a solvate thereof,

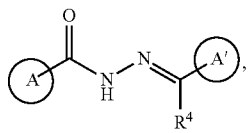

(I)

wherein A is selected from the group consisting of:

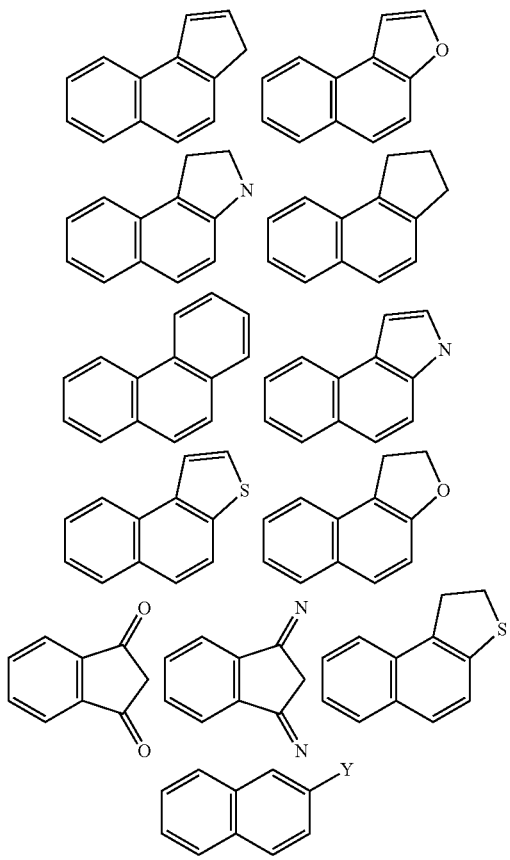

wherein A' is selected from the group consisting of:

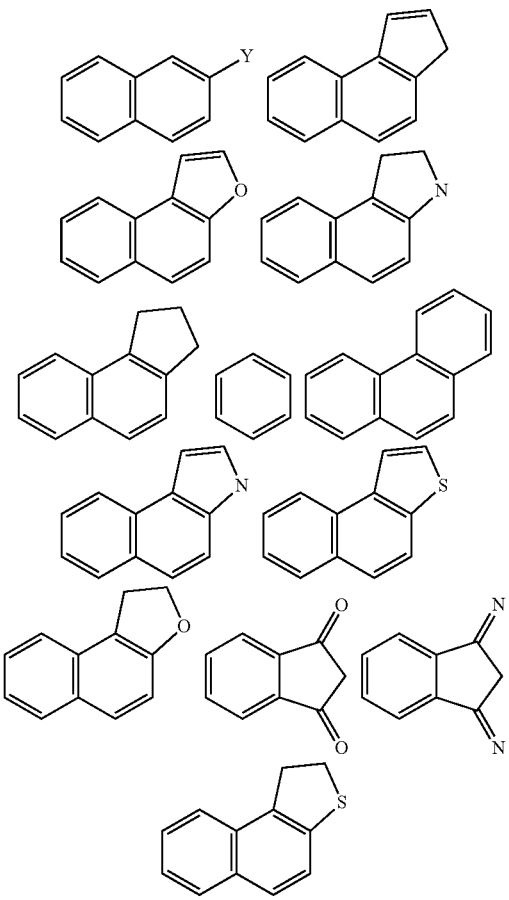

wherein at least one of A or A' is optionally substituted one or more times with at least one of $C_1$-$C_{10}$ alkyl, $C(=O)H$, $C(=O)OH$, $C(=O)OR^1$, $C(=O)NH_2$, $C(=O)NHR^1$, $C(=O)NR^1R^2$, $C(=O)R^1$, $CH_2F$, $CHF_2$, $CF_3$, $C\equiv N$, OH, $OR^1$, $OC(=O)R^1$, $OC(=O)OR^1$, $OC(=O)NH_2$, $OC(=O)NHR^1$, $OC(=O)NR^1R^2$, $NH_2$, $NHR^1$, $NR^1R^2$, $N(H)C(=O)R^1$, $N(R^1)C(=O)R^2$, $N(H)C(=O)OR^1$, $N(R^1)C(=O)OR^2$, $N(H)C(=O)NH_2$, $N(R^1)C(=O)NH_2$, $N(H)C(=O)NHR^1$, $N(R^1)C(=O)NHR^2$, $N(H)C(=O)NR^1R^2$, $N(R^1)C(=O)NR^2R^3$, $NO_2$, SH, $SR^1$, $S(=O)R^1$, $S(=O)_2R^1$, $SO_3H$, $OP(O)(OH)(OH)$, $OP(O)(OH)(OR^1)$, $OP(O)(OR^1)(OR^2)$, H, Hal, $CH_2Hal$; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I, and wherein $R^1$, $R^2$ and $R^3$ are the same or different and are independently selected from the group consisting of $C_1$-$C_{20}$ aliphatic, $C_3$-$C_{20}$ cycloaliphatic and combinations thereof; wherein Y is OH, SH or $NH_2$; and $R^4$ is H. Accordingly, the compounds of the invention, comprising a hydrazide linker, are provided for use in the treatment or prevention of a condition responsive to antagonism of the androgen receptor.

Preferably. The following compounds are excluded in from use in treatment of certain conditions 3-hydroxy-N'-(4-hydroxy-3,5-dimethoxybenzylidene)-2-naphthohydrazide (MDG489), N'-(3-methoxybenzylidene)naphtho[2,1-b]furan-2-carbohydrazide (MDG505), 3-hydroxy-N'-(2-hydroxy-3-chlorobenzylidene)-2-naphthohydrazide (MDG618), 3-hydroxy-N'-[(1E)-1-(2-hydroxy-5-chlorophenyl)ethylidene]-2-naphthohydrazide (MDG621) and 3-hydroxy-N'-benzylidene-2-naphthohydrazide (MDG628).

With reference to the compound for the treatment of a condition responsive to antagonism of the androgen receptor of the present invention the variables A and A' may be the same or different and may be independently selected from the group consisting of $C_5$-$C_{20}$ aryl, $C_3$-$C_{20}$ heteroaryl, and combinations thereof, optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, CH$_2$F, CHF$_2$, CF$_3$, C≡N, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)R$^1$, N(R$^1$)C(=O)R$^2$, N(H)C(=O)OR$^1$, N(R$^1$)C(=O)OR$^2$, N(H)C(=O)NH$_2$, N(R$^1$)C(=O)NH$_2$, N(H)C(=O)NHR$^1$, N(R$^1$)C(=O)NHR$^2$, N(H)C(=O)NR$^1$R$^2$, N(R$^1$)C(=O)NR$^2$R$^3$, NO$_2$, SH, SR$^1$, S(=O)R$^1$, S(=O)$_2$R$^1$, SO$_3$H, OP(O)(OH)(OH), OP(O)(OH)(OR$^1$), OP(O)(OR$^1$)(OR$^2$), Cl, Br, F, and I.

With reference to the compound for the treatment of a condition responsive to non-LBP antagonism of the androgen receptor of the present invention the variables A and A' may be the same or different and may be independently selected from the group consisting of:

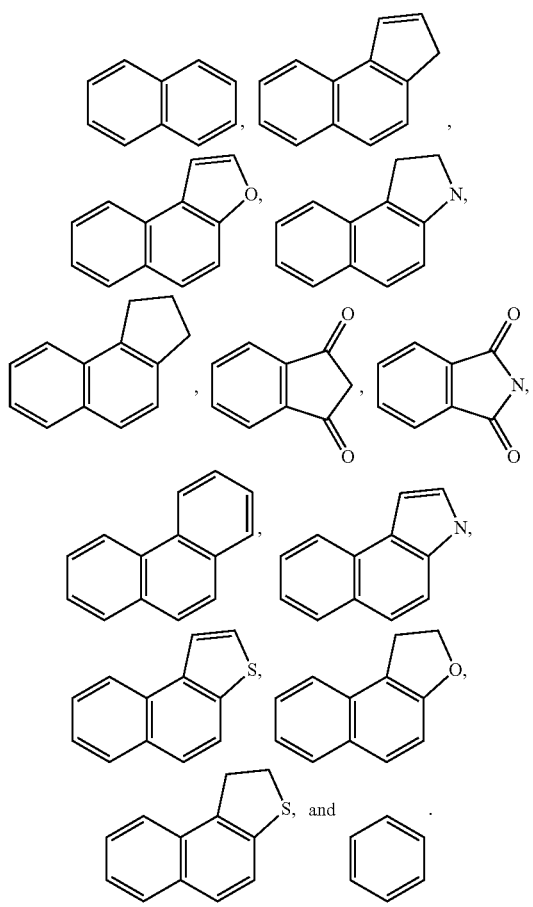

optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, CH$_2$F, CHF$_2$, CF$_3$, C≡N, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)R$^1$, N(R$^1$)C(=O)R$^2$, N(H)C(=O)OR$^1$, N(R$^1$)C(=O)OR$^2$, N(H)C(=O)NH$_2$, N(R$^1$)C(=O)NH$_2$, N(H)C(=O)NHR$^1$, N(R$^1$)C(=O)NHR$^2$, N(H)C(=O)NR$^1$R$^2$, N(R$^1$)C(=O)NR$^2$R$^3$, NO$_2$, SH, SR$^1$, S(=O)R$^1$, S(=O)$_2$R$^1$, SO$_3$H, OP(O)(OH)(OH), OP(O)(OH)(OR$^1$), OP(O)(OR$^1$)(OR$^2$), Cl, Br, F, and I, wherein
R$^1$, R$^2$ and R$^3$ are the same or different and may be independently selected from the group consisting of $C_1$-$C_{20}$ aliphatic, $C_3$-$C_{20}$ cycloaliphatic and combinations thereof.

With reference to the compound for the treatment of a condition responsive to antagonism of the androgen receptor of the present invention, preferred compounds comprise A which is selected from the group consisting of:

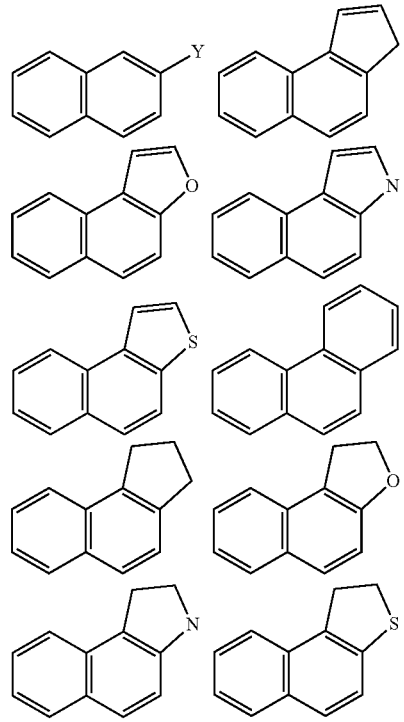

wherein A is optionally substituted one or more times with at least one of $C_1$-$C_{10}$ alkyl, C(=O)H, C(=O)OH, C(=O)OR$^1$, C(=O)NH$_2$, C(=O)NHR$^1$, C(=O)NR$^1$R$^2$, C(=O)R$^1$, OH, OR$^1$, OC(=O)R$^1$, OC(=O)OR$^1$, OC(=O)NH$_2$, OC(=O)NHR$^1$, OC(=O)NR$^1$R$^2$, NH$_2$, NHR$^1$, NR$^1$R$^2$, N(H)C(=O)R$^1$, N(R$^1$)C(=O)R$^2$, N(H)C(=O)OR$^1$, N(R$^1$)C(=O)OR$^2$, N(H)C(=O)NH$_2$, N(R$^1$)C(=O)NH$_2$, N(H)C(=O)NHR$^1$, N(R$^1$)C(=O)NHR$^2$, N(H)C(=O)NR$^1$R$^2$, N(R$^1$)C(=O)NR$^2$R$^3$, NO$_2$, SH, SR$^1$, S(=O)R$^1$, S(=O)$_2$R$^1$, SO$_3$H, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$, R$^2$ and R$^3$ are the same or different and are independently selected from the group consisting of $C_1$-$C_{20}$ aliphatic, $C_3$-$C_{20}$ cycloaliphatic and combinations thereof.

In other preferred embodiments, the use comprises compounds wherein A is selected from the group consisting of:

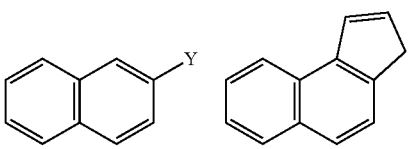

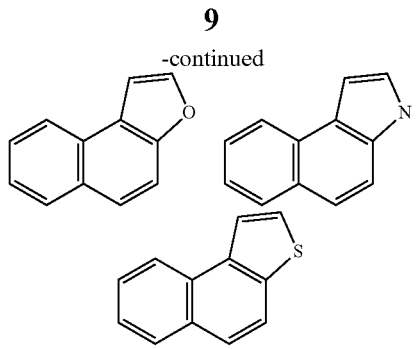

wherein A is optionally substituted one or more times with at least one of $C_1$-$C_6$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from $C_1$-$C_6$ aliphatic and combinations thereof.

Other preferred compounds for use in the present invention comprise A which is selected from the group consisting of:

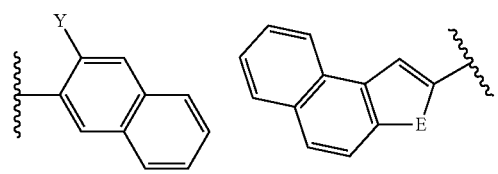

wherein Y is —OH, —SH or —NH$_2$, E is O, S or NH.

Particularly preferred compounds for the use of the invention comprise A which is selected from the group consisting of:

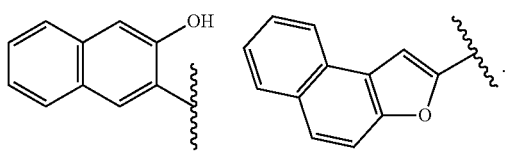

Other compounds used comprise A' that is optionally substituted one or more times with at least one of $C_1$-$C_6$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from $C_1$-$C_6$ aliphatic and combinations thereof.

Other compounds still comprise A' that is optionally substituted one or more times with at least one of $C_1$-$C_6$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from $C_1$-$C_6$ aliphatic and combinations thereof.

Of particular interest are compounds for use of the invention in which A' is selected from the group consisting of:

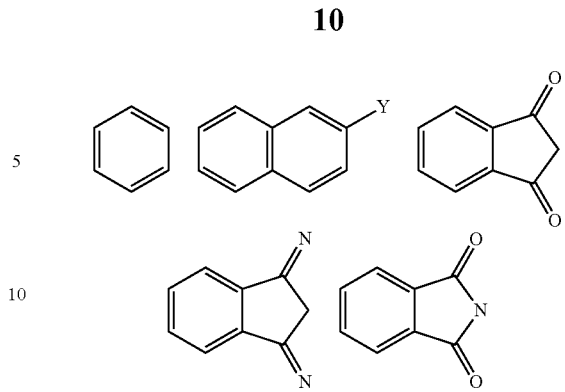

wherein A' is optionally substituted one or more times with at least one of $C_1$-$C_{10}$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, SO$_3$H, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from the group consisting of $C_1$-$C_{10}$ aliphatic, $C_3$-$C_{15}$ cycloaliphatic and combinations thereof.

Preferably, $C_1$-$C_{10}$ aliphatic is a $C_1$-C6 aliphatic, more particularly a $C_1$-$C_3$ aliphatic.

Desirably compounds for the use of the present invention comprise A' is selected from the group consisting of:

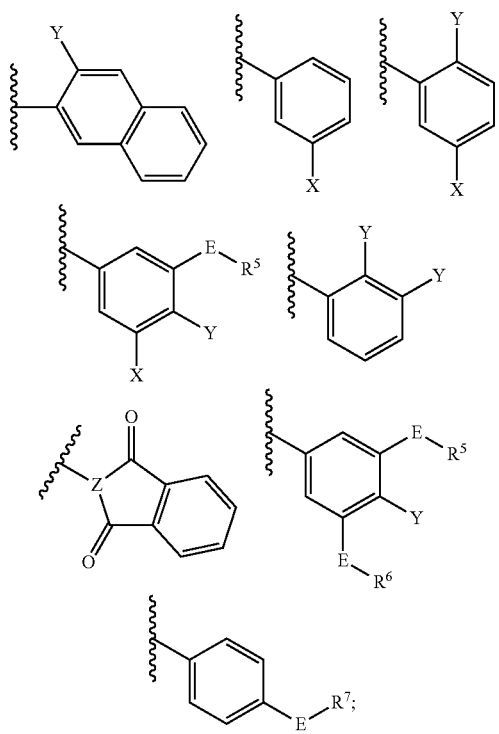

wherein
Y is selected from OH, SH, and NH$_2$;
X is selected from OH, OCH$_3$, COOH, COOCH$_3$, NO$_2$, Cl, Br, I and F;
Z is selected from CH and N;
E is selected from O, S, and NH;
R$^5$ and R$^6$ are the same or different and are $C_1$-$C_5$ alkyl; and
R$^7$ is $C_3$-$C_5$ straight chain alkyl.

More preferred still are compounds for use described herein wherein A' is selected from the group consisting of:

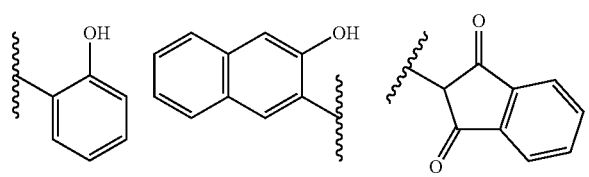

wherein A' is optionally substituted one or more times with at least one of methyl, C(=O)OH, C(=O)OMe, OH, OMe, NO$_2$, Cl, Br, and I.

A particular group of compounds for use of the invention comprise A which selected from the group consisting of:

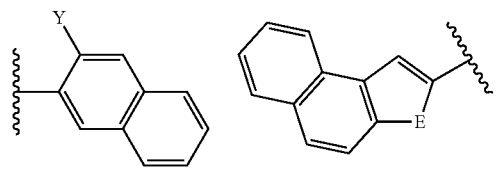

wherein Y is OH, —SH or —NH$_2$, E is O, S or NH; and wherein A' is selected from the group consisting of:

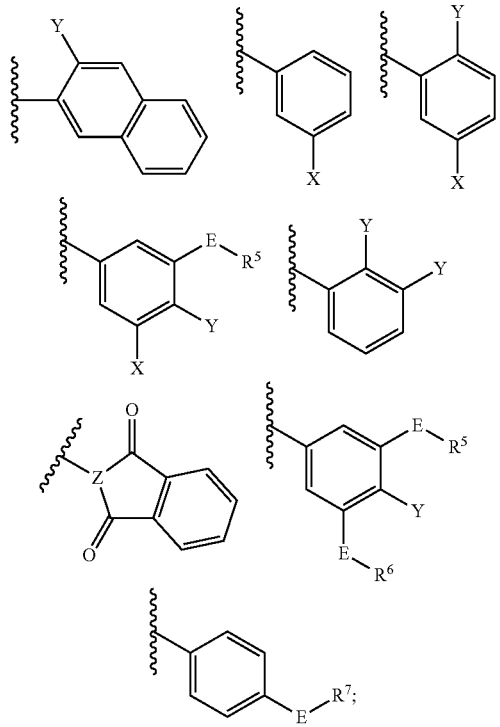

wherein
Y is selected from OH, SH, and NH$_2$;
X is selected from OH, OCH$_3$, COOH, COOCH$_3$, NO$_2$, Cl, Br, I and F;
Z is selected from CH and N;
E is selected from O, S, and NH;
R$^5$ and R$^6$ are the same or different and are C$_1$-C$_5$ alkyl; and
R$^7$ is C$_3$-C$_5$ straight chain alkyl.

As used herein, the bond broken by the squiggle line is utilised to indicate attachment of A (or whatever other variable is in question) to the linker L. In the above two examples, the carbons next to Y and E are bonded to the linker L.

A may be selected from the group consisting of:

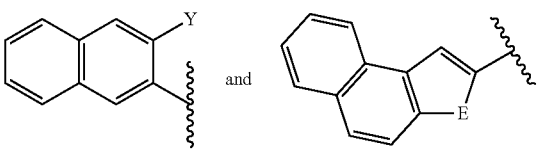

wherein
Y is OH; and
E is O.

In one embodiment, when A is selected from:

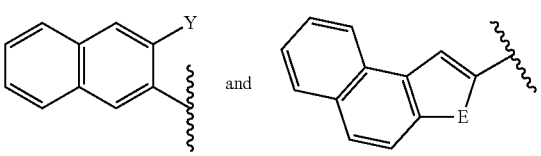

wherein
Y is selected from OH, SH, and NH$_2$; and
E is selected from O, S, and NH.
A' is selected from:

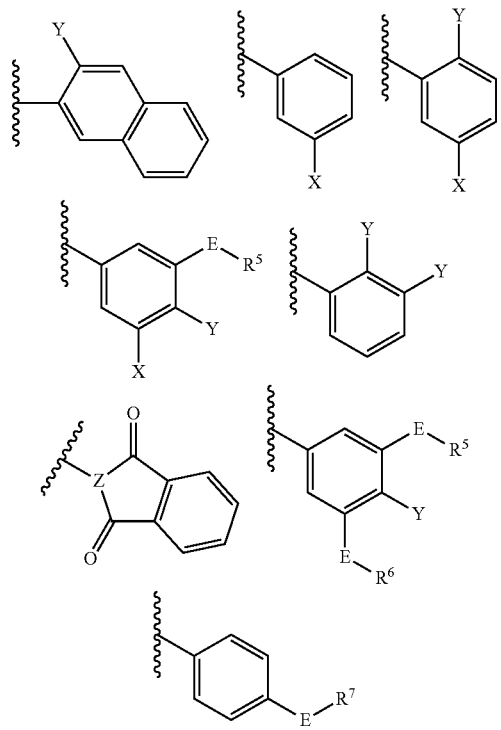

wherein
Y is selected from OH, SH, and NH$_2$;
X is selected from OH, OCH$_3$, COOH, COOCH$_3$, NO$_2$, Cl, Br, I and F;
Z is selected from CH and N;

E is selected from O, S, and NH;
R⁵ and R⁶ are the same or different and are $C_1$-$C_5$ alkyl; and
R⁷ is $C_3$-$C_5$ straight chain alkyl.

In a further embodiment, when A is:

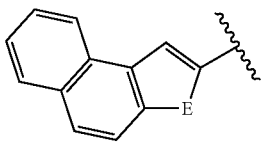

wherein
E is selected from O, S, and NH;
A' is selected from the group consisting of:

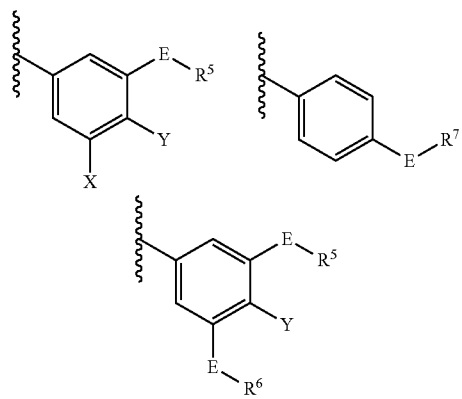

wherein
Y is selected from OH, SH, and NH₂;
X is selected from Cl, Br, I and F;
E is selected from O, S, and NH;
R⁵ and R⁶ are the same or different and are $C_1$-$C_5$ alkyl; and
R⁷ is $C_3$-$C_5$ straight chain alkyl.

In yet a further embodiment, when A is:

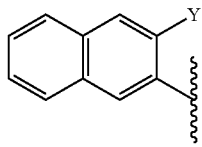

wherein
Y is selected from OH, SH, and NH₂;
A' is selected from the group consisting of:

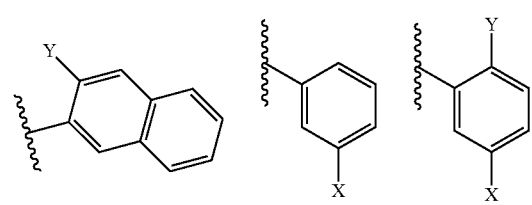

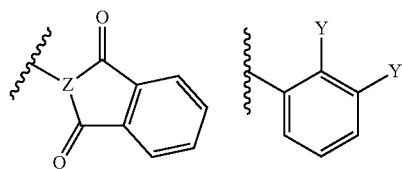

wherein
Y is selected from OH, SH, and NH₂;
X is selected from OH, OCH₃, COOH, COOCH₃, NO₂, Cl, Br, I and F;
Z is selected from CH and N.

Preferred A' groups in the compounds for use according to the invention are is selected from the group consisting of:

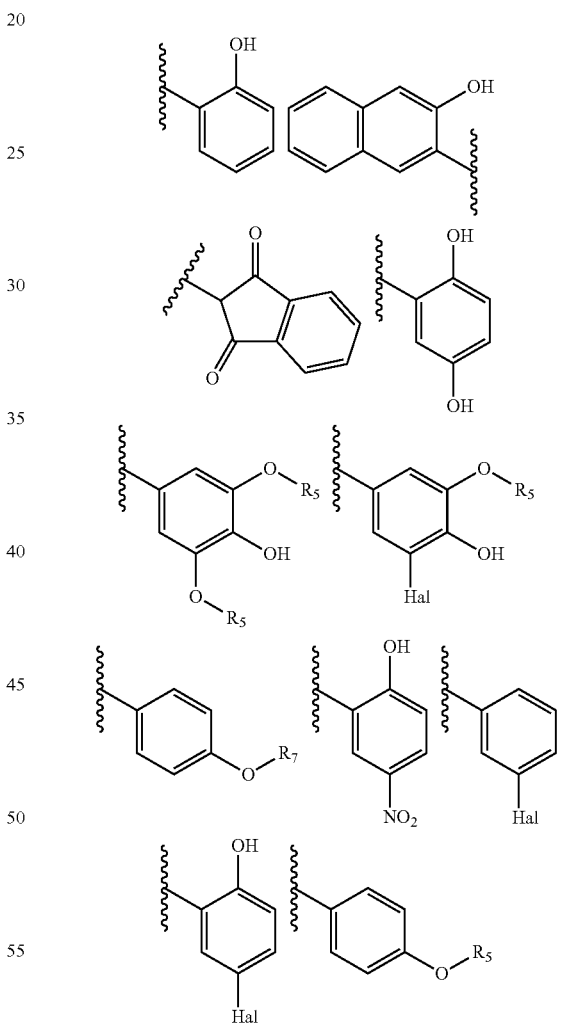

wherein Hal is Cl, Br, I or F; R5 is re the same or different and are $C_1$-$C_5$ alkyl; and R⁷ is $C_3$-$C_5$ straight chain alkyl.

For example, A' may be selected from the group consisting of:
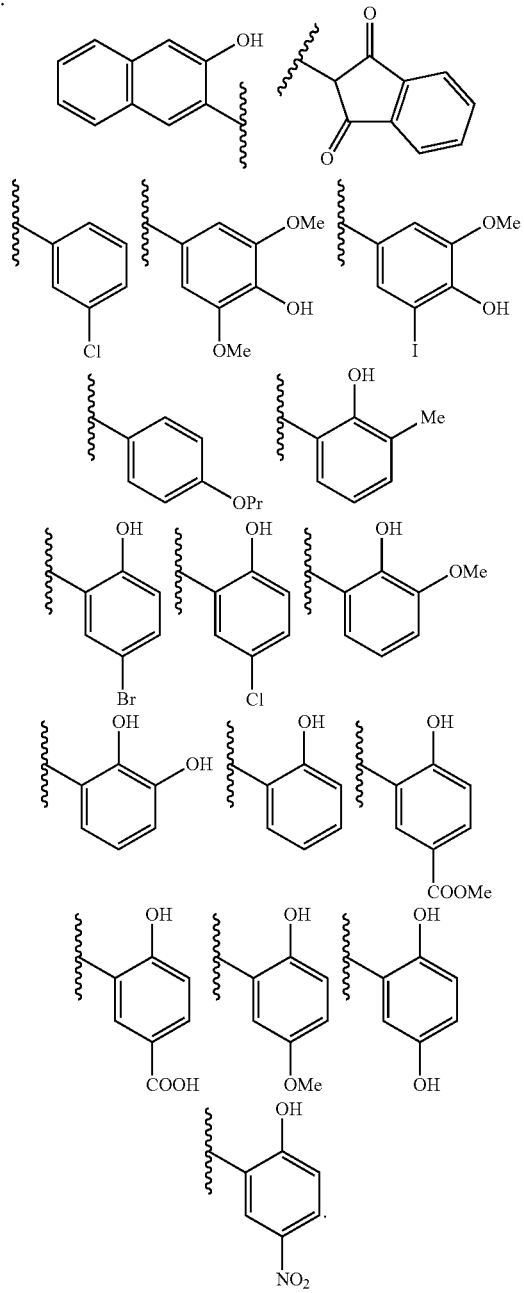
Thus certain preferred compounds of the present invention may be selected from the group consisting of:
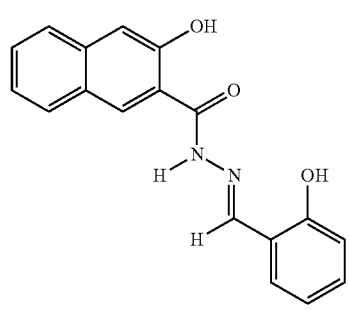
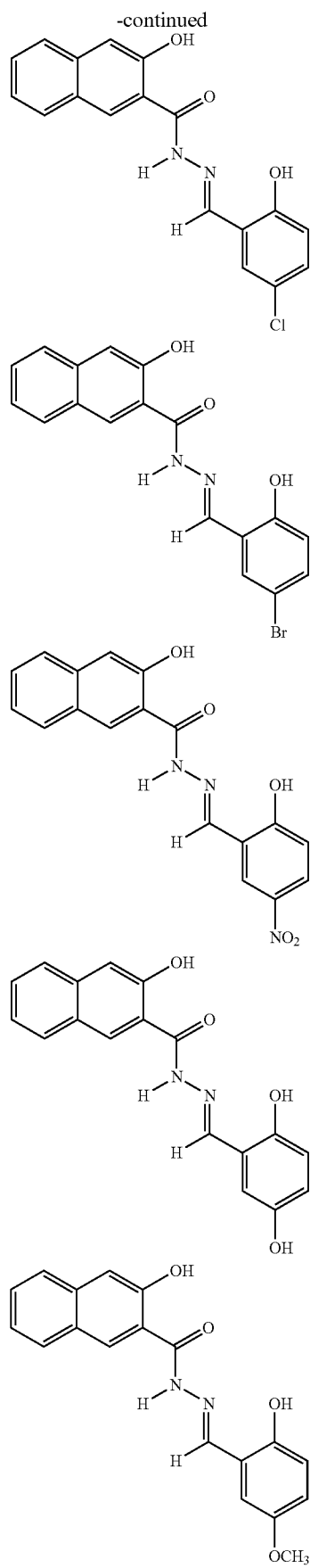

-continued
17
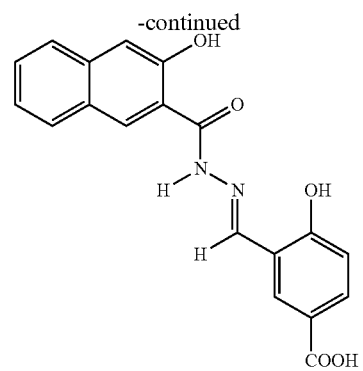
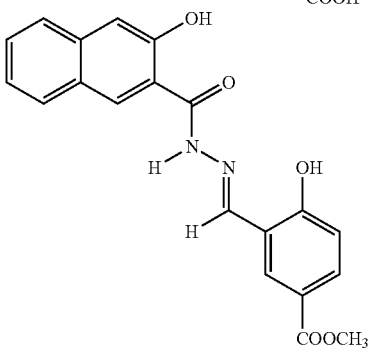
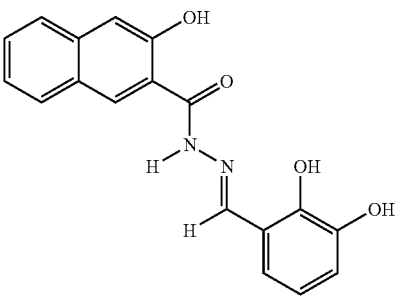
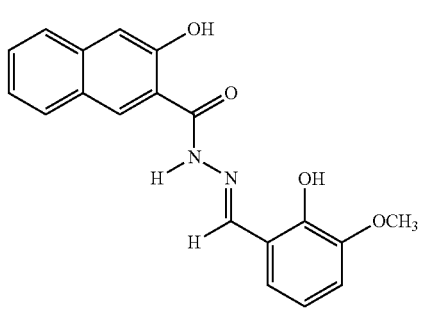
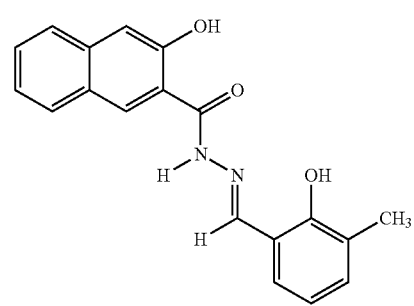
18
-continued
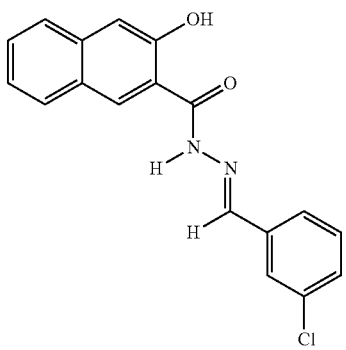
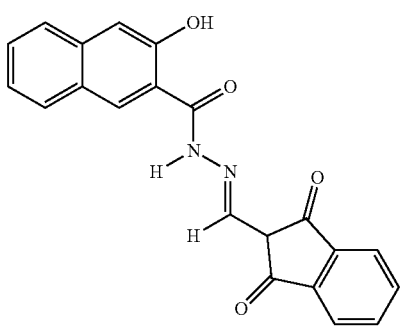
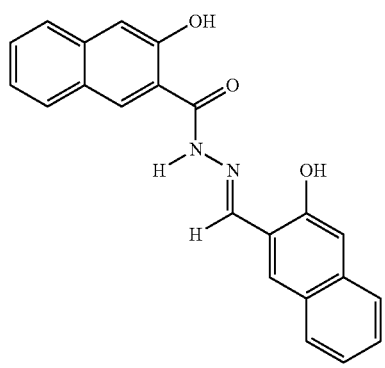
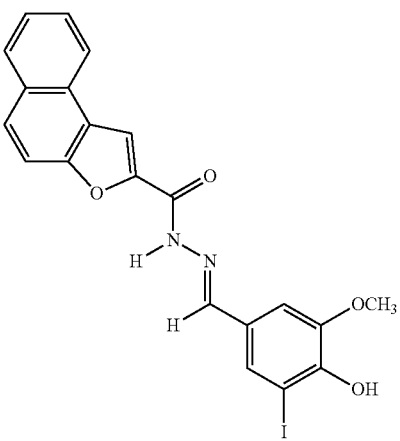

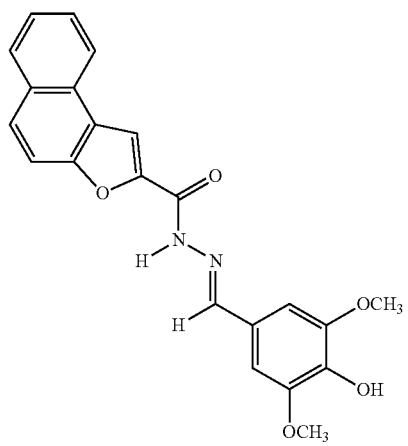
and
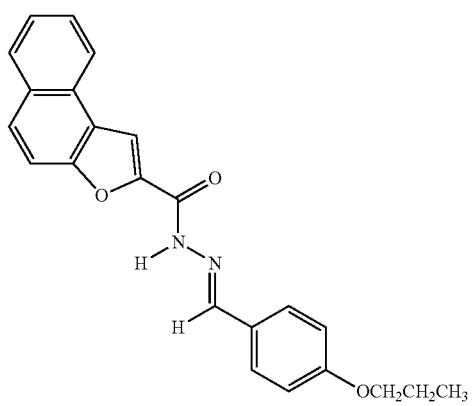
Most active compounds can be selected from the group consisting of:
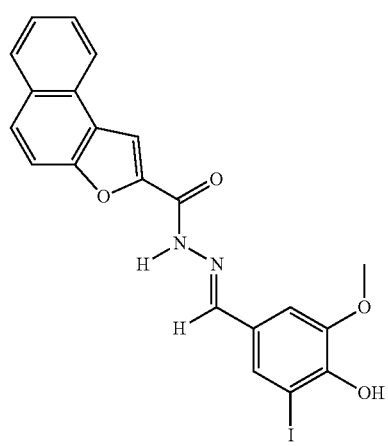
MDG15
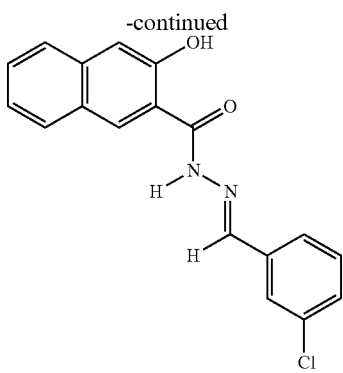
MDG491
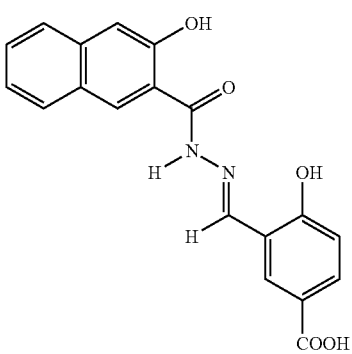
MDG630
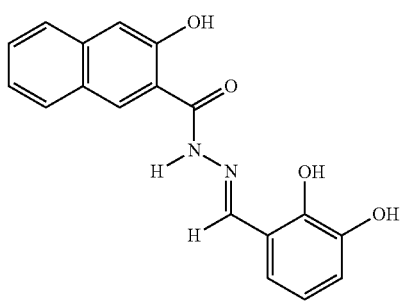
MDG173
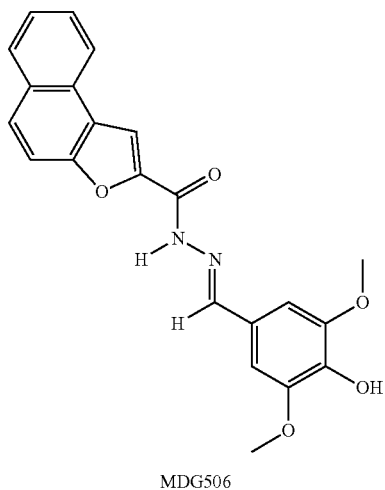
MDG506

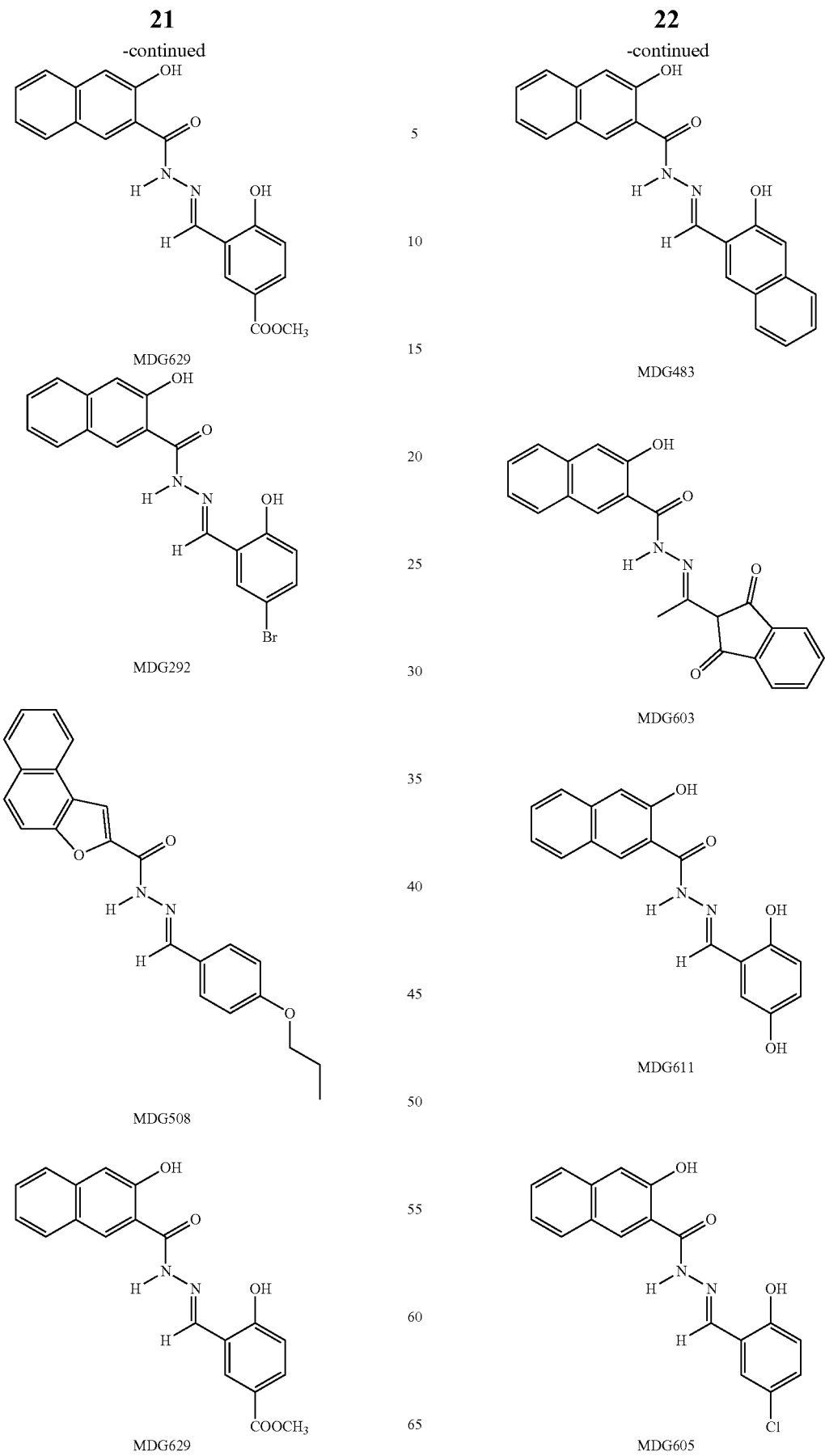

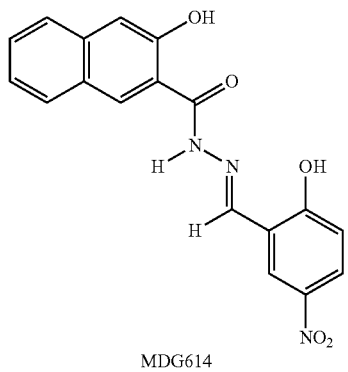 [SMILES: COc1ccc(O)c(/C=N/NC(=O)c2cc3ccccc3cc2O)c1]

MDG614

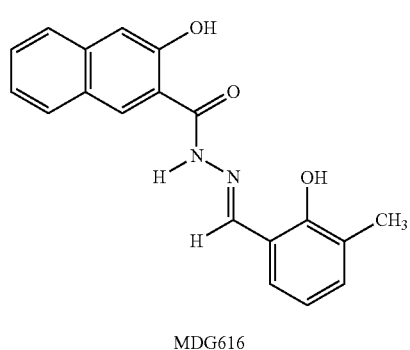

MDG616

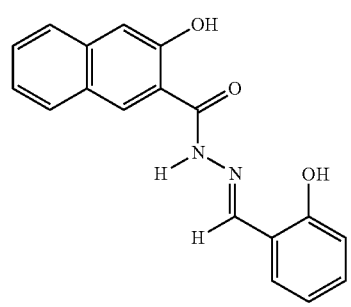

MDG608

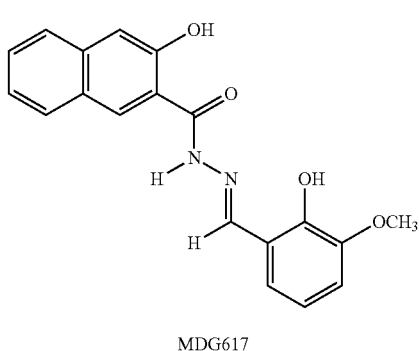

MDG617

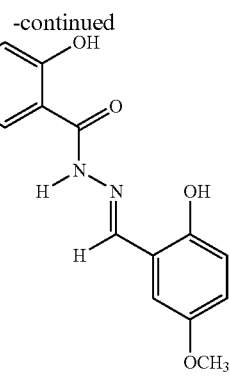

MDG612

Suitably, at least one compound of the invention can be used in the prevention and/or treatment of a condition responsive to antagonism of the androgen receptor, which may be selected from the group consisting of: prostate cancer (prostatic carcinoma), acne, hirsutism, male-pattern baldness, and prostatic hyperplasia. Particularly preferred conditions are prostate cancer (prostatic carcinoma), hirsutism, male-pattern baldness, and prostatic hyperplasia. Most preferred condition is castration resistance prostate cancer.

In a related aspect of the invention there is provided a compound (per se), a tautomer thereof, a pharmaceutically acceptable salt thereof, or a solvate thereof, of formula:

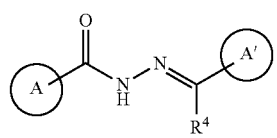

wherein A is:

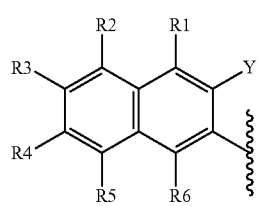

wherein Y is selected from OH. SH, and $NH_2$ each of R1-R6 are the same or different and are selected from the group consisting of $C_1$-$C_6$ alkyl, SH, $NH_2$, $NR_2$, COOH, COOR, $CH_2$Hal, H, Hal, $CH_2$Hal; $CH_2$OH, $CH_2$SH, $CH_2NH_2$, $CH_2NH_2$, $CH_2$COOH, $CH_2COOR^1$, NHC(NH)$NH_2$, wherein Hal is Cl, Br, F, and I; and wherein A' is selected from the group consisting of:

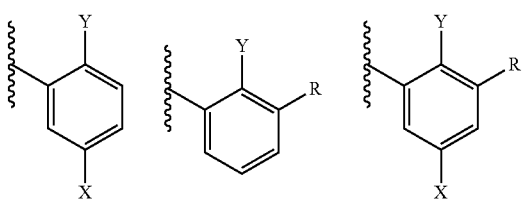

-continued

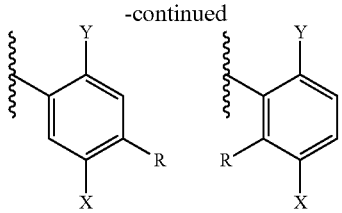

wherein
Y is selected from H, OH, SH, and NH$_2$;
X is selected from H. Hal, OH, OCH$_3$, COOCH$_3$, COOH, COOR, NO$_2$, wherein Hal is selected from Cl, I and F; and
R is selected from H. OH, C$_1$-C$_6$ alkyl, SH, NH$_2$, NR$_2$, COOH, COOR, CH$_2$Hal, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I.

Preferably, the following compounds are excluded from the compounds per se of the invention: 2-Naphthalenecarboxylic acid, 3-hydroxy-, 2-[(2,4-dihydroxyphenyl)methylene]hydrazide; 2-Naphthalenecarboxylic acid, 3-hydroxy-, 2-[(2,3-d hydroxyphenyl)methylene]hydrazide; 2-Naphthalenecarboxylic acid, 3-hydroxy-, 2-[(2,4,6-tri hydroxyphenyl)methylene]hydrazide; 2-Naphthalenecarboxylic acid, 3-hydroxy-, 2-[(2,3,4-tri hydroxyphenyl)methylene]hydrazide; 2-Naphthalenecarboxylic acid, 3-hydroxy-, 2-[[4-(diethylamino)-2-hydroxyphenyl]methylene]hydrazide; 2-Naphthalenecarboxylic acid, 3-hydroxy-, 2-[(5-bromo-2-hydroxy-3-iodophenyl)methylene]hydrazide; 2-Naphthalenecarboxylic acid, 3-hydroxy-, 2-[(3-bromo-2-hydroxy-5-nitrophenyl)methylene]hydrazide; 2-Naphthalenecarboxylic acid, 3-hydroxy-, 2-[(5-bromo-3-chloro-2-hydroxyphenyl)methylene]hydrazide; 2-Naphthalenecarboxylic acid, 3-hydroxy-, 2-[(2-hydroxy-3,5-diiodophenyl)methylene]hydrazide; 2-Naphthalenecarboxylic acid, 3-hydroxy-, 2-[(3-bromo-5-chloro-2-hydroxyphenyl)methylene]hydrazide; 2-Naphthalenecarboxylic acid, 3-hydroxy-, 2-[(3,5-dibromo-2-hydroxyphenyl)methylene]hydrazide; 2-Naphthalenecarboxylic acid, 3-hydroxy-, 2-[(3,5-dichloro-2-hydroxyphenyl)methylene]hydrazide; 2-Naphthalenecarboxylic acid, 3-hydroxy-, 2-[(2-hydroxy-3-nitrophenyl)methylene]hydrazide; 2-Naphthalenecarboxylic acid, 3-hydroxy-, 2-[(2-hydroxy-3,5-dinitrophenyl)methylene]hydrazide; or 2-Naphthalenecarboxylic acid, 3-hydroxy-, 2-[(5-chloro-2-hydroxy-3-nitrophenyl)methylene]hydrazide.

Preferably, the compound per se of the invention comprises A selected from:

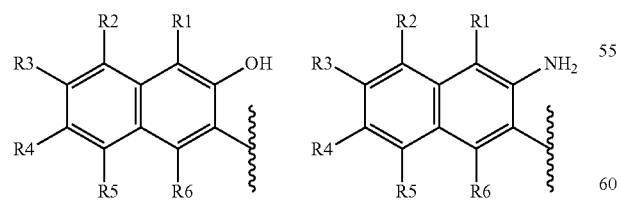

wherein each of R$^1$-R$^6$ are the same or different and are selected from the group consisting of C$_1$-C$_6$ alkyl, SH, NH$_2$, NR$_2$, COOH, COOR, CH$_2$Hal, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I; and wherein A' is selected from the group consisting of:

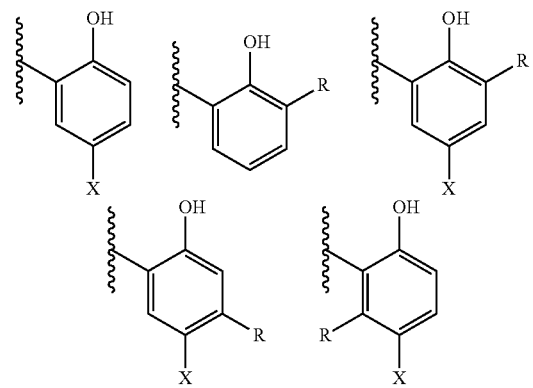

wherein
X is selected from H, Hal, OH, OCH$_3$, COOCH$_3$, COOH, COOR, NO$_2$, wherein Hal is selected from Cl, I and F; and
R is selected from H, OH, C$_1$-C$_6$ alkyl, SH, NH$_2$, NR$_2$, COOH, COOR, CH$_2$Hal, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$,
wherein Hal is Cl, Br, F, and I,
More preferred compound per se of the invention has general formula:

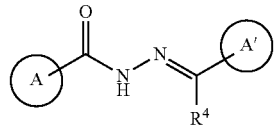

wherein A is:

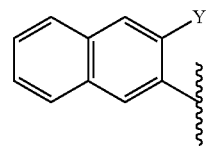

wherein Y is selected from OH. SH, and NH$_2$; and
wherein A' is selected from the group consisting of:

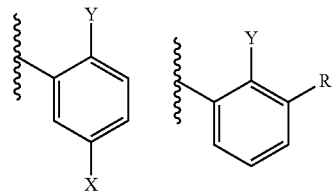

wherein
Y is selected from OH, SH, and NH$_2$;
X is selected from OH, COOH, COOR, NO$_2$, Cl, I and F; and
R is C$_1$-C$_6$alkyl.
Preferably, R is C$_1$-C$_3$alkyl. Preferably Y is OH. Preferably, X is OH. COOH or COOCH$_3$. X being Cl, I or Br is preferred. X being NO$_2$ is also desirable. Preferably. R is methyl, ethyl, propyl or butyl. Suitably, R is methyl or ethyl.

In a preferred embodiment. Y of A is OH; Y of A' is —OH; and X is OH, COOH or COOCH$_3$; and R is CH$_3$.

Most preferred compound per se may be selected from:

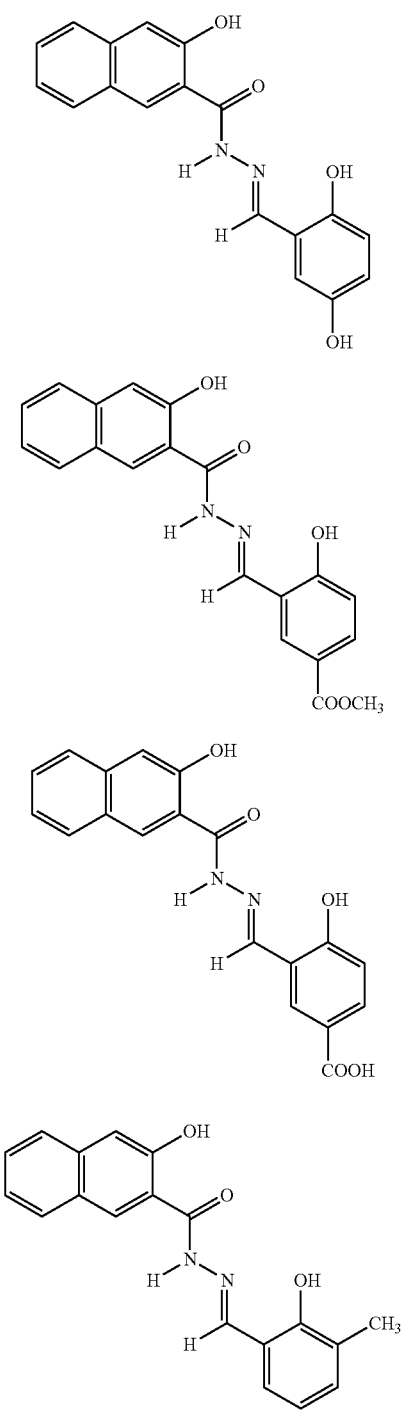

Suitably, the compounds (per se) of the invention may be used as a medicament. Desirably, the medicament is for the treatment and/or prevention of the above-mentioned conditions.

In a further related embodiment, there is provided a pharmaceutical composition comprising a compound according to the invention, a tautomer thereof, a pharmaceutically acceptable salt thereof, or a solvate thereof, and optionally a pharmaceutically acceptable excipient.

With reference to the compound of the present invention, a tautomer thereof, a pharmaceutically acceptable salt thereof, or a solvate thereof for use in the treatment of a condition responsive to non-LBP antagonism of the androgen receptor, the condition responsive to antagonism of the androgen receptor may be selected from the group consisting of prostate cancer (prostatic carcinoma), acne, hirsutism, male-pattern baldness, and prostatic hyperplasia. Use in the treatment of prostate cancer (prostatic carcinoma), hirsutism, male-pattern baldness, and prostatic hyperplasia is preferred. Desirably, the condition responsive to antagonism of the androgen receptor may be prostate cancer. Most preferably, the condition may be castration resistance prostate cancer.

Furthermore, the compounds of the invention may be used in the manufacture of medicaments for at least one of Prostate Cancer Therapy, Acne Therapy, Hirsutism Therapy, Hair Growth Stimulants, Chemopreventive Agents, Treatment of Male Sexual Dysfunction, Oncolytic Drugs, Ophthalmic Drugs, Premalignant Conditions Therapy, Benign Prostatic Hyperplasia Therapy, Breast Cancer Therapy, Gynecological Disorders, Cervical Cancer Therapy, and/or Immunostimulants.

The present invention further provides for a method of treating a condition responsive to antagonism of the androgen receptor in a patient in need thereof, comprising administering to the patient a pharmaceutically effective amount of a compound (for use in the treatment of a condition responsive to antagonism of the androgen receptor) according to the present invention, a tautomer thereof, a pharmaceutically acceptable salt thereof, or a solvate thereof.

With reference to the method of the present invention, the condition responsive to antagonism of the androgen receptor may be selected from the group consisting of prostate cancer (prostatic carcinoma), acne, hirsutism, male-pattern baldness, and prostatic hyperplasia.

The present invention also provides for a pharmaceutical composition comprising the compound (per se) of the present invention, a tautomer thereof, a pharmaceutically acceptable salt thereof, or a solvate thereof and a pharmaceutically acceptable excipient.

In a related embodiment, one or more of the compounds of the invention may be used in a combination product for the treatment of a disease or conditions as recited herein. For example, combinations of one or more of the following actives may be provided, wherein the active is selected from the group consisting of: Calcitriol; Topitriol, Chlormadinone acetate, Cyproterone acetate, Aminoglutethimide, Eflornithine hydrochloride (BAN; Rec INNM; USAN); alpha-Difluoromethylornithine hydrochloride Goserelin (BAN; Rec INN; USAN), Triptorelin (BAN; Rec INN; USAN), Itraconazole (BAN; Rec INN; USAN), Flutamide (BAN; Rec INN; USAN) Estramustine phosphate sodium (BAN; Rec INNM; USAN) 5-Azacytidine; Azacitidine (Prop INN; USAN); Azacytidine; Ladakamycin (formerly) Mitoxantrone hydrochloride (Rec INNM; USAN); Mitozantrone hydrochloride (BANM), Thalidomide (BAN; Rec INN; USAN) Disulfuram (BAN; JAN; Rec INN; USAN), Diethylstilbestrol; Stilbestrol; Stilboestrol, Venlafaxine EA; Venlafaxine hydrochloride (BANM; JAN; Rec INNM; USAN), Nilutamide (BAN; Rec INN; USAN), Paclitaxel (BAN; Rec INN); Intaxel (from Himalayan Yew), Navelbine (tartrate); Vinorelbine (BAN; Rec INN; USAN), Mepacrine hydrochloride;

Quinacrine hydrochloride (BANM; Prop INNM), Gemcitabine hydrochloride (BANM; Rec INNM; USAN), Histrelin (Rec INN; USAN), Toremifene (BAN; Rec INN; USAN), Medroxyprogesterone acetate (USAN), Nadroparin calcium (BAN; Rec INN), Leuprolide acetate (USAN); Leuprorelin acetate (BANM; Rec INNM), Buserelin acetate (BANM; Rec INN; USAN), Suramin sodium (DCF; Rec INN; USAN; USP), Leflunomide (Rec INN; USAN) Ketoconazole (BAN; JAN; Rec INN; USAN), Cytarabine (BAN; DCF; JAN; Rec INN; USAN; USP) Octeotride SDI; Octreotide LAR; Octreotide acetate (BANM; JAN; Rec INNM; USAN) Carboplatin (BAN; Rec INN; USAN), Epoetin; Erythropoietin Bicalutamide (BAN; Rec INN; USAN), Angiopeptin acetate; Lanreotide acetate (BANM; Rec INNM; USAN) Lexidronam Sm 153 (Prop INN); Samarium Sm 153 lexidronam (USAN) Ecteinascidin 743; Trabectedin (Rec INN; USAN), Docetaxel (BAN; Rec INN; USAN); Docetaxol (former INN) Leuprolide acetate depot; Leuprorelin acetate depot, Zoledronate; Zoledronic acid monohydrate (Rec INNM), Finasteride (BAN; Rec INN; USAN) Temoporfin Silipide; Silybin phosphatidylcholine complex, Romidepsin (Rec INN; USAN), Masoprocol (Rec INN; USAN); Nordihydroguaiaretic acid, Fulvestrant (Prop INN; USAN), Sargramostim (BAN; Rec INN; USAN), Atorvastatin calcium (Rec INNM; USAN), Epoetin alfa (BAN; JAN; Rec INN; USAN), Ibandronate sodium hydrate (USAN); Ibandronic acid monosodium salt monohydrate (BANM; Rec INNM), Liposomel doxorubicin hydrochloride; PEG-liposomal doxorubicin hydrochloride, Histrelin acetate (Rec INNM; USAN), Trastuzumab (Prop INN), Tegafur/gimeracil/oteracil, Efavirenz (Prop INNM), Everolimus (Rec INN; USAN), Doxercalciferol (Rec INN; USAN) Silymarin Abiraterone acetate (BANM; Prop INNM; USAN), Temsirolimus (Rec INN; USAN); Temserolimus (former INN), Strontium chloride Sr 89 (USAN), Vinflunine (Prop INN; USAN), Metformin hydrochloride (BAN; Rec INN; USAN) Dutasteride (Prop INNM; USAN), Phenylbutyric acid sodium salt; Sodium phenylbutyrate (USAN), Bevacizumab (Rec INN), Imatinib mesylate (Rec INNM; USAN), Suberanilohydroxamic acid; Suberoylanilide hydroxamic acid; Vorinostat (Rec INN; USAN) Cetuximab (Rec INN; USAN), Gefitinib (Prop INN; USAN), Chorionic gonadotropin (human), Histamine dihydrochloride (Rec INNM; USAN), Paracalcin; Paricalcitol (Prop INN; USAN), Erlotinib hydrochloride (Rec INNM; USAN), Abarelix (Prop INN; USAN), Leuprolide acetate implant, Sipuleucel-T (USAN), Glufanide (USAN; former USAN); Oglufanide disodium (Rec INNM; USAN); Timogen, Bortezomib (Rec INN; USAN), Deltacortisone; Deltadehydrocortisone; Prednisone (BAN; Rec INN), Tolfenamic acid Arsenic trioxide (USAN), Narcosine; Noscapine (BAN; JAN; Rec INN; USAN); alpha-Narcotine, Degarelix acetate (Rec INNM; USAN), Panitumumab (Rec INN; USAN), Atrigel-Leuprolide Lenalidomide (Rec INN; USAN), Hydroxychloroquine sulfate Nimotuzumab (Rec INN) Ipilimumab (Rec INN; USAN), Kunecatechins; Sinecatechins (USAN), Cabazitaxel (Prop INN; USAN), Eribulin mesilate (Prop INNM); Eribulin mesylate (USAN), Paclitaxel nanoparticles; nab-paclitaxel, 16-Aza-epothilone B; Ixabepilone (Rec INN; USAN), Polyestradiol phosphate (BAN; Rec INN), L-Selenomethionine; Selenomethionine Pertuzumab (Rec INN; USAN), Lapatinib ditosylate (Rec INN; USAN), Sorafenib (Rec INN; USAN) Cinacalcet hydrochloride (Rec INNM; USAN) Aflibercept (Rec INN; USAN); Ziv-aflibercept, Vandetanib (Rec INN; USAN), Pasireotide (Rec INN; USAN), Sunitinib malate (Rec INNM; USAN) Axitinib (Rec INN; USAN), Holmium-166-Chitosan complex Pazopanib hydrochloride (Rec INNM; USAN), Denosumab (Rec INN; USAN) Dasatinib (Rec INN; USAN), Calciol; Cholecalciferol (BAN; Rec INN; USAN); Vitamin D3, Pomegranate juice, Enzalutamide (Prop INN; USAN), Ruxolitinib phosphate (Prop INNM; USAN), Genistein Combined Polysaccharide, Vismodegib (Prop INN; USAN), Kanglaite and Indole-3-carbinol/epigallocatechin-3-gallate.

In yet a further aspect the present invention provides for an antagonist of the androgen receptor for use in the treatment of at least one of prostate cancer, acne, hirsutism, male-pattern baldness, and prostatic hyperplasia, wherein the antagonist exhibits no partial agonist activity at the androgen receptor. The antagonist may be an allosteric modulator of the androgen receptor. Preferably, Suitably, the antagonist is an allosteric modulator of the androgen receptor. the condition is not acne. The most preferred condition is castration resistance prostate cancer.

In another embodiment, there is provided a method of identifying an allosteric modulator of the androgen receptor, the method comprising:
 i) generating a screening pharmacophore using structural data of the AF-2 region of the androgen receptor and at least one peptide sequence selected from the group consisting of FxxLF, LxxLL, and FxxLW, where x is any amino acid;
 ii) screening a virtual compound database for compounds possessing the pharmacophore generated in step i); and
assessing the ability of the compounds identified in step to fit in the AF-2 region of a crystal structure of the androgen receptor.

The step of generating a screening pharmacophore may comprise using structural data of the AF-2 region of the androgen receptor and the peptide sequence FxxLF, where x is any amino acid.

The step of screening a virtual compound database for compounds possessing the pharmacophore generated in step i) may comprise screening a plurality of virtual compound databases.

The step of assessing the ability of the compounds identified in step ii) to fit in the AF-2 region of a crystal structure of the androgen receptor may comprise screening the compounds on a plurality of androgen receptor crystal structures and considering those compounds that exhibit good binding on all said plurality of androgen receptor crystal structures.

As used herein, the term $C_x$-$C_y$ aliphatic refers to linear, branched, saturated and unsaturated hydrocarbon chains comprising $C_x$-$C_y$ carbon atoms (and includes $C_x$-$C_y$ alkyl, $C_x$-$C_y$ alkenyl and $C_x$-$C_y$ alkynyl). Similarly, references to $C_x$-$C_y$ alkyl, $C_x$-$C_y$ alkenyl and $C_x$-$C_y$ alkynyl include linear and branched $C_x$-$C_y$ alkyl, $C_x$-$C_y$ alkenyl and $C_x$-$C_y$ alkynyl As used herein, the term "$C_x$-$C_y$ cycloaliphatic" refers to unfused, fused, spirocyclic, polycyclic, saturated and unsaturated hydrocarbon rings comprising $C_x$-$C_y$ carbon atoms (and includes $C_x$-$C_y$ cycloalkyl, $C_x$-$C_y$ cycloalkenyl and $C_x$-$C_y$ cycloalkynyl).

The terms heteroaliphatic and heterocycloaliphatic embrace compounds of the above definitions, but where the carbon atoms of the hydrocarbon chains and hydrocarbon rings, respectively, are interspaced one or more times with at least one O, N or S.

As used herein, the term aryl/aromatic refers to an aromatic carbocyclic structure which is monocyclic or polycyclic, and which is unfused or fused. As used herein, the term heterocycle refers to cyclic compounds having as ring members atoms of at least two different elements. The cyclic compounds may be monocyclic or polycyclic and unfused or fused. As used herein, the term heteroaromatic/heteroaryl refers to an aromatic heterocyclic structure having as ring members atoms of at least two different elements. The heterocycle may be monocyclic or polycyclic and unfused or fused.

Where suitable, it will be appreciated that all optional and/or preferred features of one embodiment of the invention may be combined with optional and/or preferred features of another/other embodiment(s) of the invention.

BRIEF DESCRIPTION OF THE DRAWINGS

Additional features and advantages of the present invention are described in, and will be apparent from, the detailed description of the invention and from the drawings in which.

DETAILED DESCRIPTION

Figure 1:
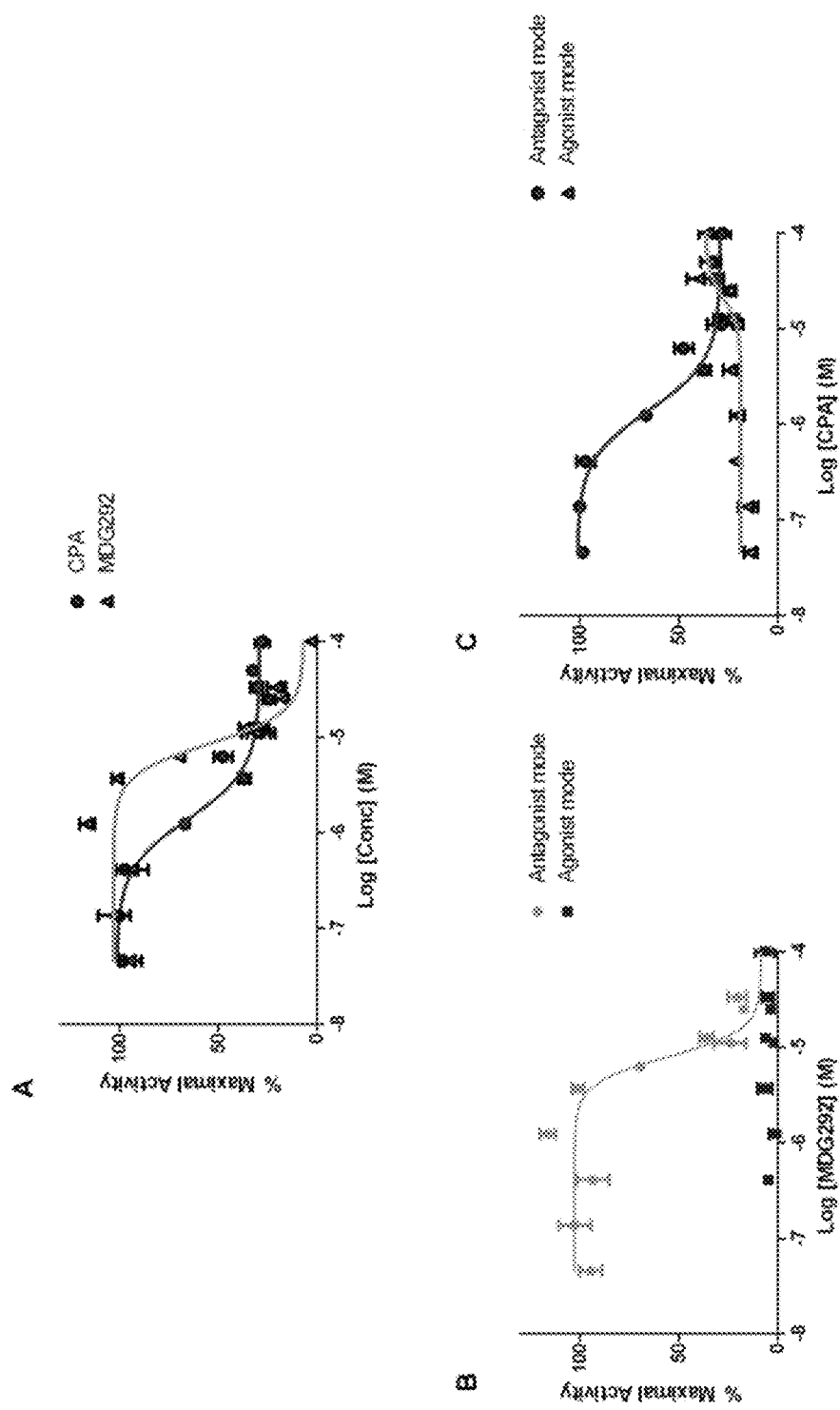
FIG. 1 illustrates the ability of Diarylhydrazides of the present invention to inhibit the AR recruitment of a D11-FxxLF peptide. Diarylhydrazides are full AR antagonist when compared to a classical antagonist like CPA. (A) A direct comparison between MDG292 and CPA in AR TR FRET antagonist mode. (B) MDG292 in both agonist and antagonist mode, showing full AR antagonism and (C) CPA in both agonist and antagonist mode, showing partial AR antagonism. Compounds were tested in a TR-FRET assay across a concentration range from 100 µM to 45 nM in presence of a concentration of DHT=$EC_{80}$ in AR-LBD wt. Data points represent the mean of two independent experiments performed in triplicate. Data was fitted using Log antagonist concentration vs response (variable slope)

It should be readily apparent to one of ordinary skill in the art that the examples disclosed herein below represent generalised examples only, and that other arrangements and methods capable of reproducing the invention are possible and are embraced by the present invention.

Methodology—Virtual Screening

A virtual screen was designed to select compounds mapping onto the peptide binding surface (AF2) of the AR receptor, based on an ensemble of documented X-ray crystal structures: 1T73, 1T74, 1T76, 1T79, 1T7F, 1T7M, 1T7R &1T7T [Hur E, Pfaff S J, Payne E S, Gron H, Buehrer B M, et al. (2004) Recognition and accommodation at the androgen receptor coactivator binding interface. *PLoS Biol* 2:E274. Molecular Operating Environment (MOE) software was employed to preprocess the proteins and removal of the coactivator peptides from the complexes. An initial pharmacophore was generated using the MOE pharmacophore elucidator and considering the most significant features, which involved hydrophobic, donor and acceptor features. The seven X-ray structures of coactivator peptide bound AR supra were used to define key ligand-derived pharmacophoric features of the most represented motifs occurring in known AR coactivators. Initially, common key interaction motifs within the peptide of the form FxxLF, LxxLL or FxxLW were considered to generate a consensus AF-2 pharmacophore. Subsequently, a second site-derived pharmacophore model was advanced based on the specific characteristics of the androgen receptor AF-2 region, which included two additional hydrophobic/aromatic features to represent the Phe side chains present in the FxxLF coactivator motif (1T7R), so as to increase the selectivity for AR over other families of nuclear receptor. These pharmacophore models were then applied for in silico screens of small-molecule commercial libraries to identify compounds that resemble the "active principle" of the starting peptides.

A number of vendor databases were selected for screening of ligands, including Amsterdam (5,389 compounds), Peakdale (8,188), Asinex—Platinum collection (75,258), Specs (175,800), Maybridge (56,870) and Zinc (4.6 million) compounds. A Bayesian analysis was performed on the peptide structures to estimate parameters of an underlying distribution based on the observed distribution. The above databases were then filtered for those compounds with properties similar to the peptides, thus focusing the search on the AR ligand chemical space. Any salts or duplicates were removed. All molecules were standardised for stereochemistry and charges and ionised at a pH of 7.4 and all calculable tautomers were enumerated. At this stage the conformational flexibility of the screening compounds were explored using the Omega software (OpenEye Scientific package). A maximum of 50 conformations were generated for each molecule in the dataset.

The virtual molecules were overlaid on and compared to the generated pharmacophore of the active ligands and those molecules that compared favourably were advanced for additional virtual screening and scoring. The Fast Rigid Exhaustive Docking (FRED) software as implemented in OpenEye Scientific's package was used to exhaustively examine all possible poses within the protein site, filtering for shape complementarity and scoring. The smaller databases (Amsterdam and Peakdale) were screened on all 13 crystal structures and only ligands scoring well on more than one crystal structure were considered. The larger databases SPECS, ASINEX, Maybridge and Zinc were screened on the 1T7R crystal structure.

This initial screen identified two small molecules (MDG15 and MDG173), both Diarylhydrazides, as possible non-LBP AR antagonists. Non LBP modulatory activity was experimentally evidenced by demonstration of an $IC_{50}$ in the range of 50-100 µM in AR TR-FRET coactivator displacement assay and their inability to displace bound fluorescently-labelled ligand from the LBP through an FP assay. These first round 'hit' molecules mapped only partially to the screening pharmacophore. Accordingly, an optimization round of screening was initiated to explore the utility of the scaffold for more effective disruption of AR:coactivator interaction.

A structural similarity search was conducted on MDG173 and MDG15 using a Tanimoto coefficient of >70% on the Specs compound database to furnish a new screening series of 37 compounds bearing the desired diarylhydrazide scaffold. This second round screen identified four small molecules (MDG506, MDG 508, MDG 483 and MDG292) with improved activity ($IC_{50}$<50 µM in an AR TR-FRET assay). These ligands were taken forward for additional investigation. Considering the first and second screening rounds results, a new series of Diarylhydrazide analogues was synthesized in our labs, based on pure chemical Structure-Activity Relationship (SAR) criteria and evaluated biologically following our standard protocol for AR non-ligand-binding pocket antagonists.

Synthetic Methods

General scheme for the synthesis of compounds of the present invention:

Scheme 1.

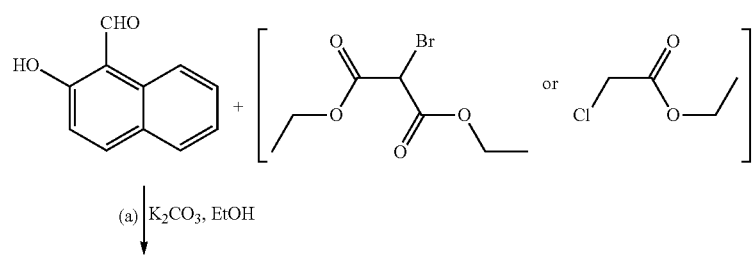

(a) $K_2CO_3$, EtOH

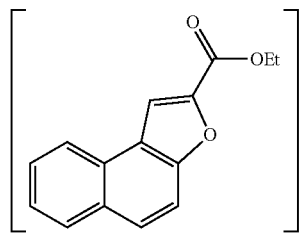
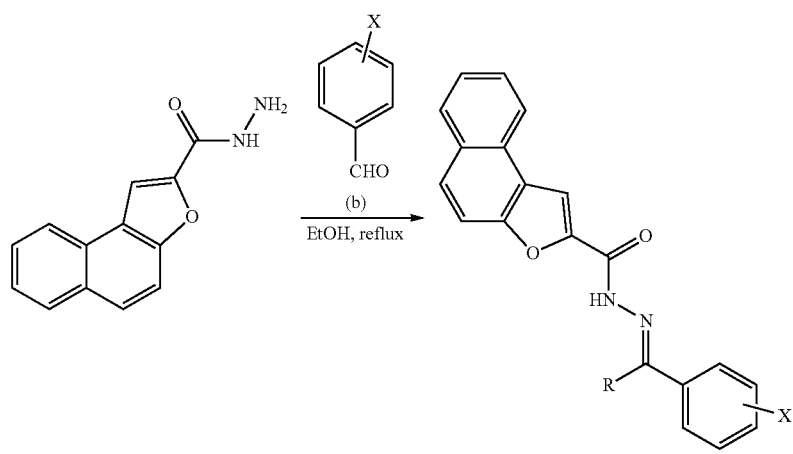
Scheme 2.
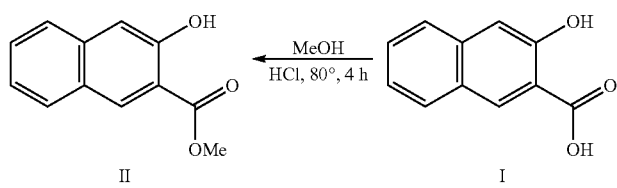

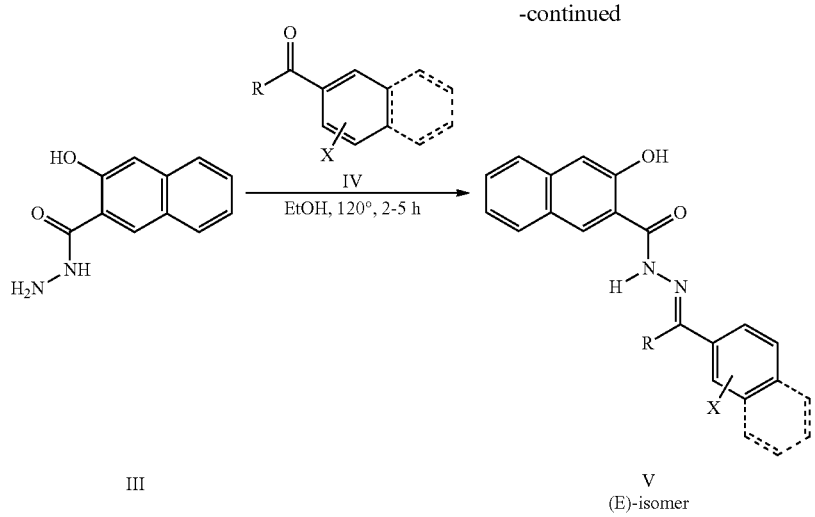

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Biochemistry I (on Target Studies)
Diarylhydrazides are Full AR Non-LBP Antagonists of the Androgen Receptor Diarylhydrazides obtained through Virtual Screening and SAR processes showed activity as inhibitors of the recruitment of the fluorescent labelled (fl) D11-FXXLF coactivator peptide in the presence of an agonist (DHT) concentration equal to $EC_{80}$ using time-resolved FRET assays. D11-FXXLF is a peptide developed from random phage display technology that resembles the SRC family of coactivator proteins in its flanking sequence but that also has an AR N-terminal interaction domain of the type FXXLF44. Thus, it is a biological mimic of the N-terminal and the SRC coactivator interactions with the AR LBD.

Figure 4:
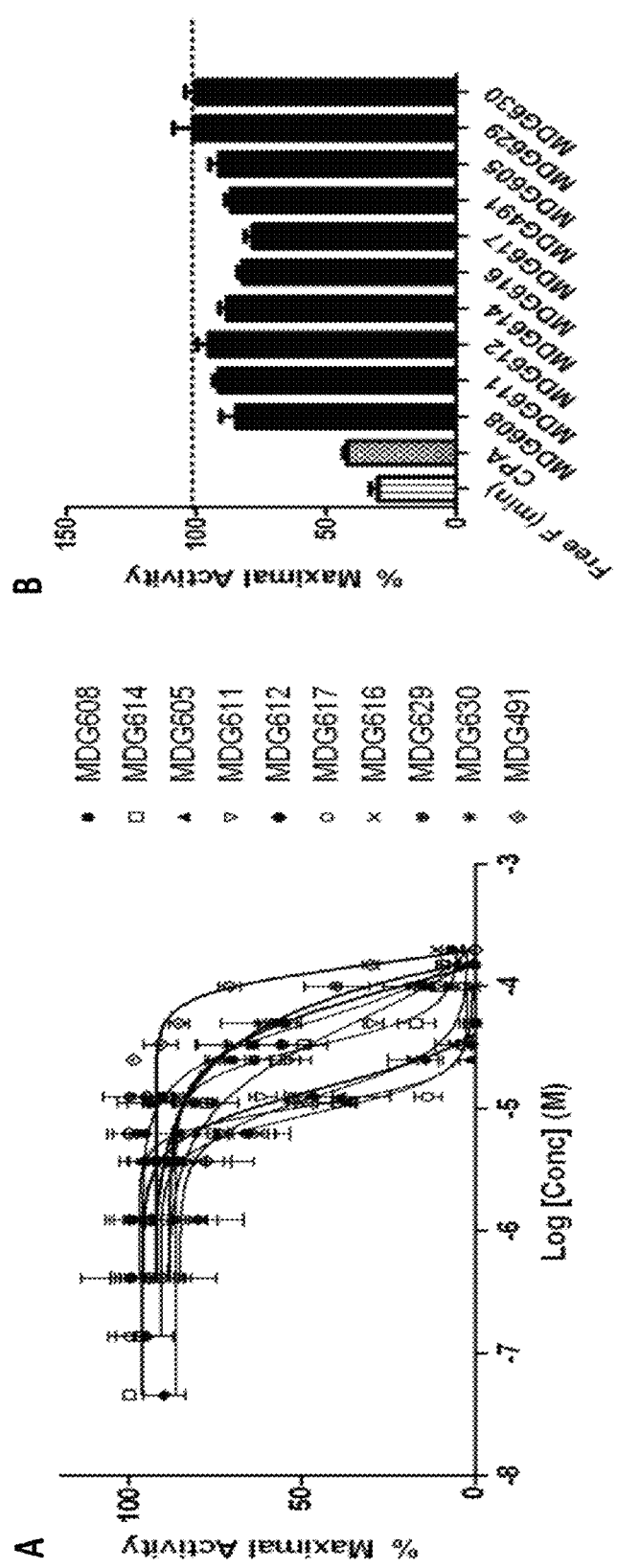
FIG. 4 illustrates the ability of Diarylhydrazides of the present invention to inhibit the AR recruitment of a D11-FxxLF peptide. (A) Compounds MDG491, MDG605, MDG608, MDG611, MDG612, MDG614, MDG616, MDG617, MDG629 & MDG630 tested in a TR-FRET assay across a concentration range from 100 µM to 45 nM in presence of a concentration of DHT=$EC_{80}$ in AR-LBD wt. Data points represent the mean of two independent experiments performed in triplicate. (B) Fluorescence polarization data of MDG491, MDG605, MDG608, MDG611, MDG612, MDG614, MDG616, MDG617, MDG629 & MDG630 plotted as % Maximal Activity represented by AR-LBD and fluorophore complex (0% inhibition). Minimum control value represents free fluorophore (Free F) in solution (100% inhibition)

A full 12 point dose-response curve was determined for those compounds which exhibited a dose-responsive behaviour in inhibiting the coactivator recruitment to AR, as shown by a reduction in the measured TR-FRET signal as 520 nm/495 nm emission ratio from the Fluorescein and Terbium respectively. Diarylhidrazides MDG15, MDG173, MDG292, MDG483, MDG491, MDG506, MDG508, MDG603, MDG605, MDG608, MDG611, MDG612, MDG614, MDG616, MDG617, MDG629 and MDG630 were identified as full AR antagonists (FIGS. 2A & 4A).

| Compounds | AR (wt) | AR T877A |
|---|---|---|
| MDG483 | 15.9 ± 3.2 µM | 11.1 ± 3.2 µM |
| MDG292 | 13.3 ± 3.1 µM | 12.4 ± 2.2 µM |
| MDG506 | 26.3 ± 3.8 µM | 33.2 ± 5.9 µM |
| MDG508 | 17.9 ± 6.9 µM | 28.1 ± 6.7 µM |

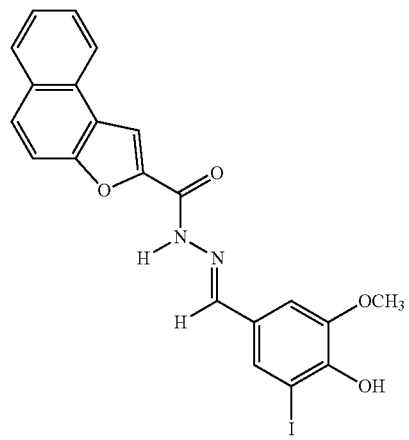

MDG15

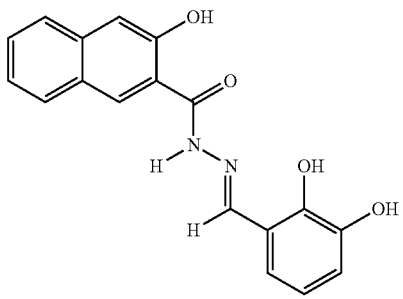

MDG173

MDG292
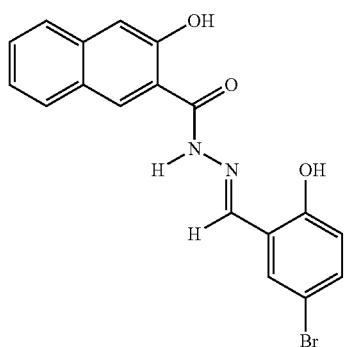
MDG508
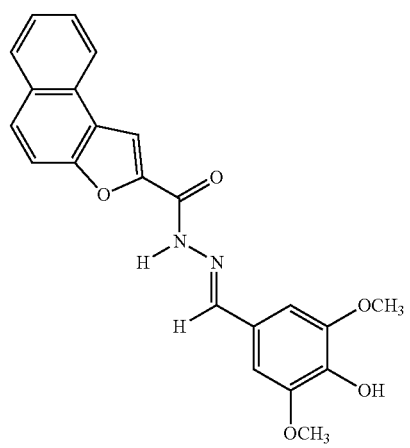
MDG483
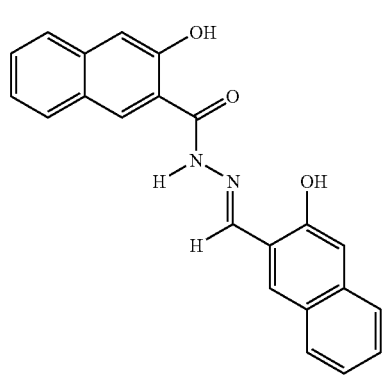
MDG603
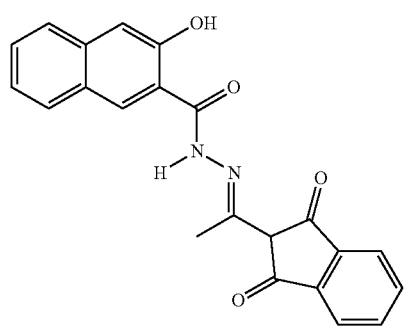
MDG491
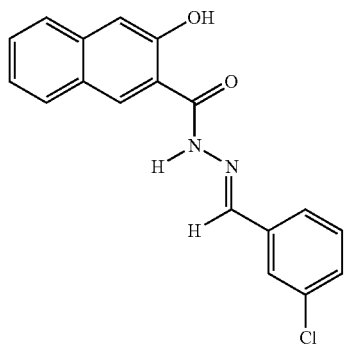
MDG605
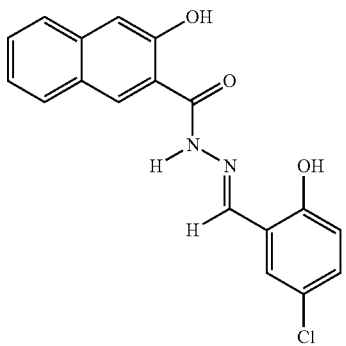
MDG506
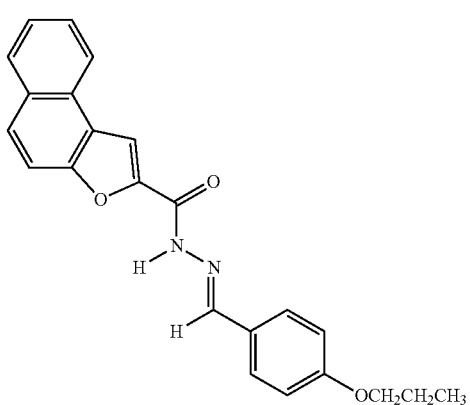
MDG608
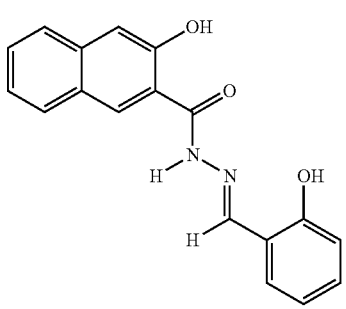

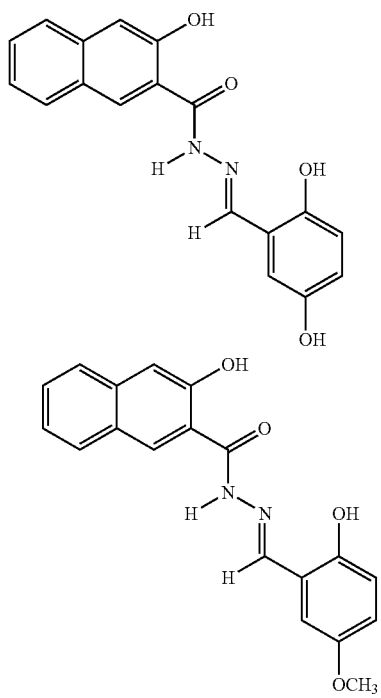

MDG611

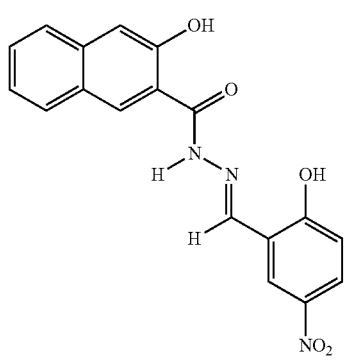

MDG614

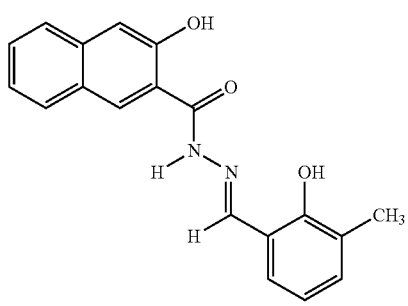

MDG616

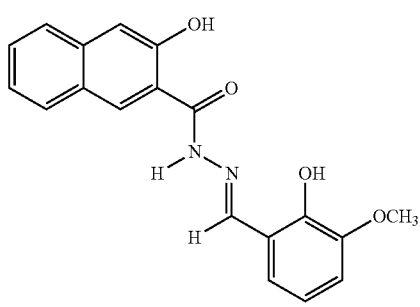

MDG617

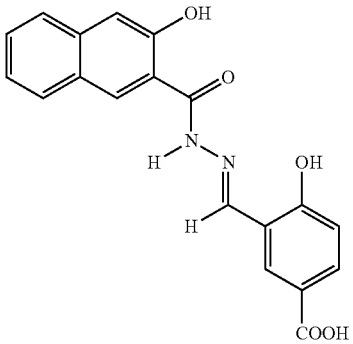

MDG629

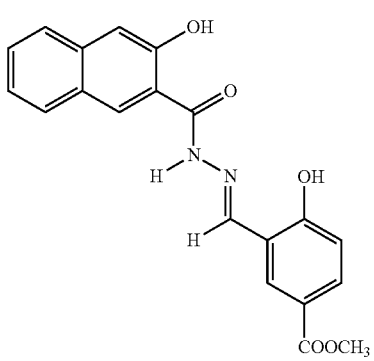

MDG630

The maximal activity value in presence of a saturating concentration of DHT was calculated as per established methods [Gunther J R, Du Y, Rhoden E, Lewis I, Revennaugh B, et al. (2009)]. The background signal, representing diffusion enhanced FRET in the absence of AR LBD, was subtracted from the FRET value of each compound and from the maximal signal, representing FXXLF bound AR in presence of DHT at an $EC_{80}$ concentration.

$$\frac{(FRET \text{ signal} - \text{background}) \text{compound}}{(FRET\text{max signal} - \text{background})DMSO} * 100. \quad \text{Equation 1}$$

To further validate the utility of these ligands in PCa, on-target binding experiments were also performed using the recombinant T877A AR mutant, characteristic of advanced stage androgen-independent PCa. In TR-FRET T877A AR mutant, Diarylhidrazides demonstrated similar activity to that observed in the wild type assays, indicating their potential in advanced phases of prostate cancer (FIG. 2B).

One of the 'classical' antiandrogens drawbacks is their intrinsic partial agonistic activity, which limits their utility in CRPC. To improve these limitations, advances in LBP targeted therapy have yielded a second generation of antiandrogens, such as MDV3100 and ARN-509, characterized as full AR antagonists, and currently in clinical trials (phase III and phase II respectively) for their potential treatment of CRPC. Differentiation of Diarylhidrazides action mechanism of antagonism compared to 'classical' partial antiandrogens like CPA, was proved by running the TR-FRET assay in both antagonist and agonist mode. Diarylhydrazides are full AR antagonist when compared to a classical antagonist like CPA (FIG. 1).

Diarylhydrazides Inhibit FXXLF Recruitment by AR Through a Non-LBP Mediated Mechanism The TR-FRET assay cannot differentiate between direct coactivator antagonists acting on the LBD surface and 'classical' AR antagonists which also functionally disrupt coactivator recruitment by displacing DHT from the ligand binding pocket. To characterize the nature of the antagonist effect, compounds were tested for their ability to displace a potent fluorescent ligand (fluorophore) from the AR LBP through a fluorescence polarization (FP) assay at a single point concentration (50 µM), using Cyproterone Acetate (CPA) at the same concentration as a reference, a known AR LBP-mediated antagonist. Diarylhydrazides showed inhibition of the AR-LBD and fluorophore complex, indicating a non-LBP mediated mechanism of AR inhibition (FIGS. 1C & 4B).

Fluorescence polarization assays are susceptible by fluorescence interference/aggregation and light scattering issues by compounds present in the wells. This could lead to false positive or false negative hits. This problem is addressed in and the presence of false 'hits' can be determined by plotting the total fluorescence intensity of the assay versus the anisotropy for each compound.

Figure 3:
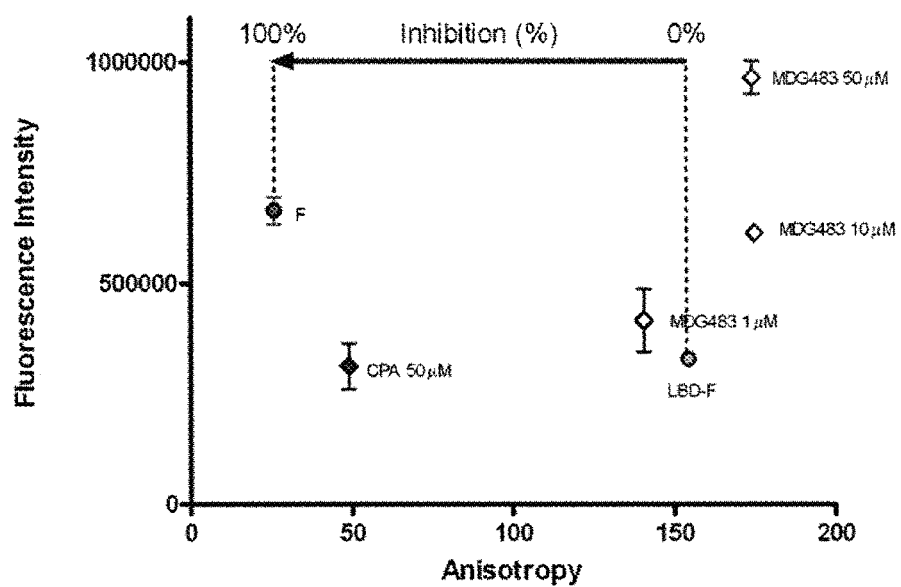
FIG. 3 illustrates fluorescence interference/aggregation assays. MDG483 is a false negative at 50 µM but returns to the inhibition range at 1 µM. MDG483 appears to have solubility issues in the chosen assay buffer at high concentration. MDG483 is therefore a true negative at 1 µM where the inhibition of the LBD-F complex is around 0%. CPA 50 µM was used as a true positive control.

To minimize the possibility of such false negative or positive reporting, the FP data was rigorously interrogated through examination of both auto-fluorescence and aggregation (FIG. 3). None of the compounds tested showed competing auto-fluorescence in the assay conditions or was shown to be a false negative.

Diarylhydrazides are AR Potential Selective Coactivator Interaction Disruptors

The selectivity of these compounds for AR over other members of the same phylogenetic branch of the steroidal nuclear receptor subfamily was proved. Compound binding affinities for Progesterone Receptor (PR), Glucocorticoid Receptor (GR), Estrogen Receptor alpha and Estrogen Receptor beta were determined using TR-FRET (Table 2).

TABLE 2

Data are presented as averages of at least two independent experiments. $IC_{50}$ values are shown as ± SEM (n = 6).
NA = not active at 100 µM.
NR LBDs $IC_{50}$ (µM)

| Compounds | GR | PR | ER-α | ER-β |
| --- | --- | --- | --- | --- |
| MDG483 | >100 | 8.4 ± 1.4 | 10.2 ± 3 | 12 ± 0.4 |
| MDG292 | >100 | 22.5 ± 5.4 | >100 | >100 |
| MDG506 | >100 | 27.7 ± 7.3 | >100 | >100 |
| MDG508 | >100 | 5.9* | 4 ± 1.4 | 2.9* |
| MDG608 | >100 | >100 | >100 | nd |
| MDG611 | >100 | nd** | nd | nd |
| MDG612 | >100 | 50-100** | nd | nd |
| MDG614 | >100 | nd** | >100 | >100 |
| MDG616 | >100 | nd** | nd | nd |
| MDG617 | >100 | nd** | nd | nd |
| MDG629 | >100 | nd | nd | nd |
| MDG630 | >100 | nd | nd | nd |
| MDG605 | >100 | nd | 50-100 | 50-100 |
| MDG491 | >100 | 50-100 | >100 | >100 |

Figure 5:
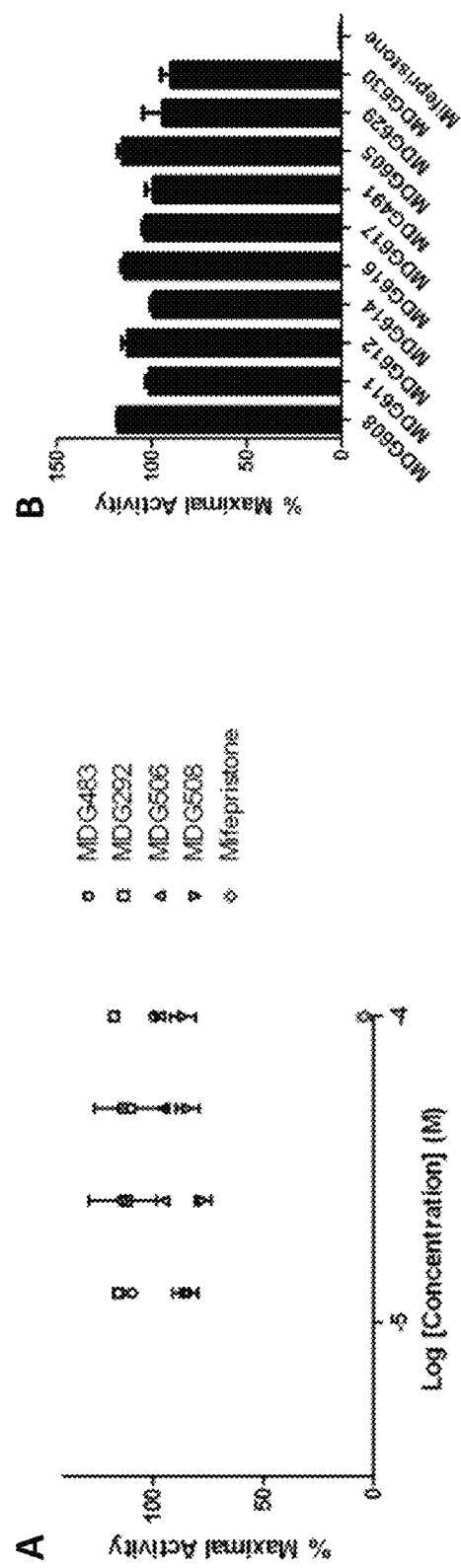
FIG. 5 illustrates the selectivity of Diarylhydrazides of the present invention amongst the steroid receptor subfamily (Glucocorticoid Receptor, GR). (A) Diarylhydrazides MDG292, MDG483, MDG506 & MDG508 do not affect SRC1-4 recruitment by GR LBD. Compounds were tested in a TR-FRET assay across a concentration range from 100 µM to 12.5 µM in presence of a concentration of Dexamethasone=$EC_{80}$. Mifepristone, a known GR antagonist, was included at a single point concentration of 100 µM. Data points represent the mean of two independent experiments performed in triplicate. (B) Diarylhydrazides MDG491, MDG605, MDG608, MDG611, MDG612, MDG614, MDG616, MDG617, MDG629 & MDG630 do not affect SRC1-4 recruitment by GR LBD. Compounds and Mifepristone were tested in a TR-FRET assay at a single point concentration of 100 µM in presence of a concentration of Dexamethasone=$EC_{80}$. Data points represent the mean of two independent experiments performed in triplicate.

Selectivity of the diarylhydrazide scaffold for the AR was demonstrated through TR-FRET evaluation in GR. Dexamethasone bound receptor recruitment of the fluorescently labelled SCR1-4 coactivator was unimpaired at screening concentrations up to 100 µM for all the diarylhydrazides evaluated (FIG. 5).

Figure 6:
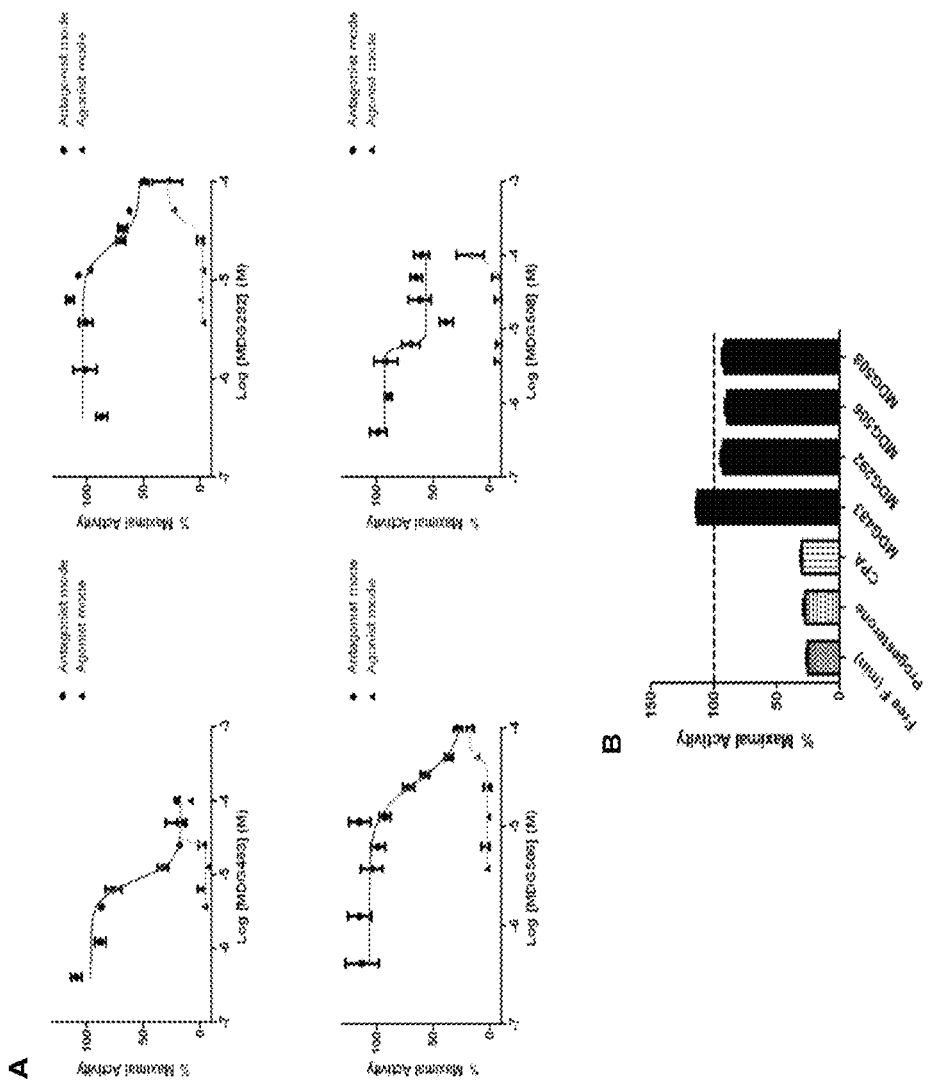
FIG. 6 illustrates the selectivity of Diarylhydrazides of the present invention amongst the steroid receptor subfamily (Progesterone Receptor, PR). (A) Diarylhydrazides MDG292, MDG483, MDG506 & MDG508 partially inhibit the PR recruitment of a fluorescent labelled SRC1-4. Compounds were tested in a TR-FRET assay across a concentration range from 100 µM to 45 nM where applicable in presence of a concentration of Progesterone=$EC_{80}$ in PR-LBD (antagonist mode) or in absence of progesterone (agonist mode). Data points represent the mean of two independent experiments performed in triplicate. Data was fitted using Log antagonist concentration vs response (variable slope). (B) Fluorescence polarization data of MDG292, MDG483, MDG506 & MDG508 plotted as % Maximal Activity represented by PR-LBD and fluorophore complex (0% inhibition). Minimum control value represents free fluorophore (Free F) in solution (100% inhibition)
Figure 7:
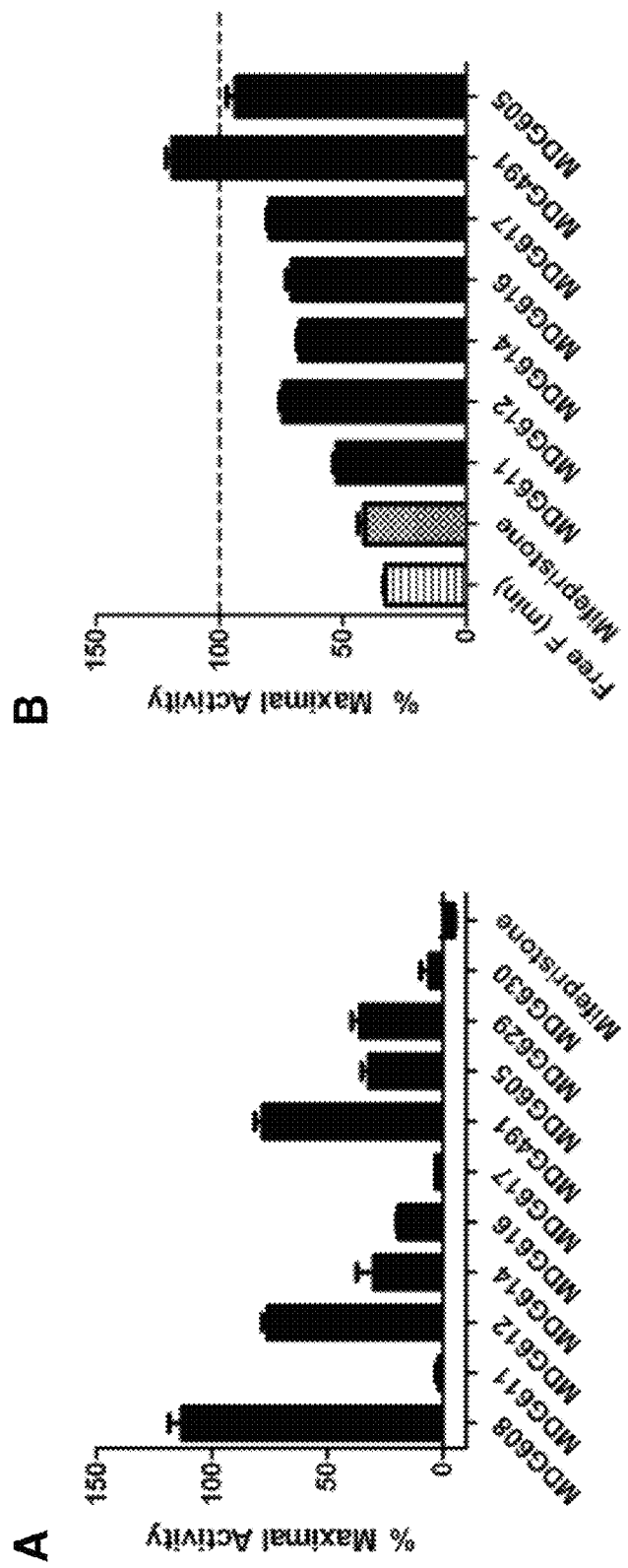
FIG. 7 illustrates the selectivity of Diarylhydrazides of the present invention amongst the steroid receptor subfamily (Progesterone Receptor, PR). (A) Diarylhydrazides MDG419, MDG605, MDG608, MDG611, MDG612, MDG614, MDG616, MDG617, MDG629 & MDG630 evaluated in the SAR study inhibit the PR LBD recruitment of a fluorescent labelled SRC1-4 coactivator. Compounds were tested in a TR-FRET assay at a maximal concentration of 100 µM in presence of a concentration of Progesterone=$EC_{80}$. Data points represent the mean of two independent experiments performed in triplicate. (B) Fluorescence polarization data of MDG419, MDG605, MDG611, MDG612, MDG614, MDG616 & MDG617 plotted as % Maximal Activity represented by PR-LBD and fluorophore complex (0% inhibition). Minimum control value represents free fluorophore (Free F) in solution (100% inhibition)

Diarylhydrazides were found to partially displace progesterone bound PR recruitment of the fluorescently labelled SCR1-4 coactivator in a TR-FRET assay (FIGS. 6 & 7).

Figure 2:
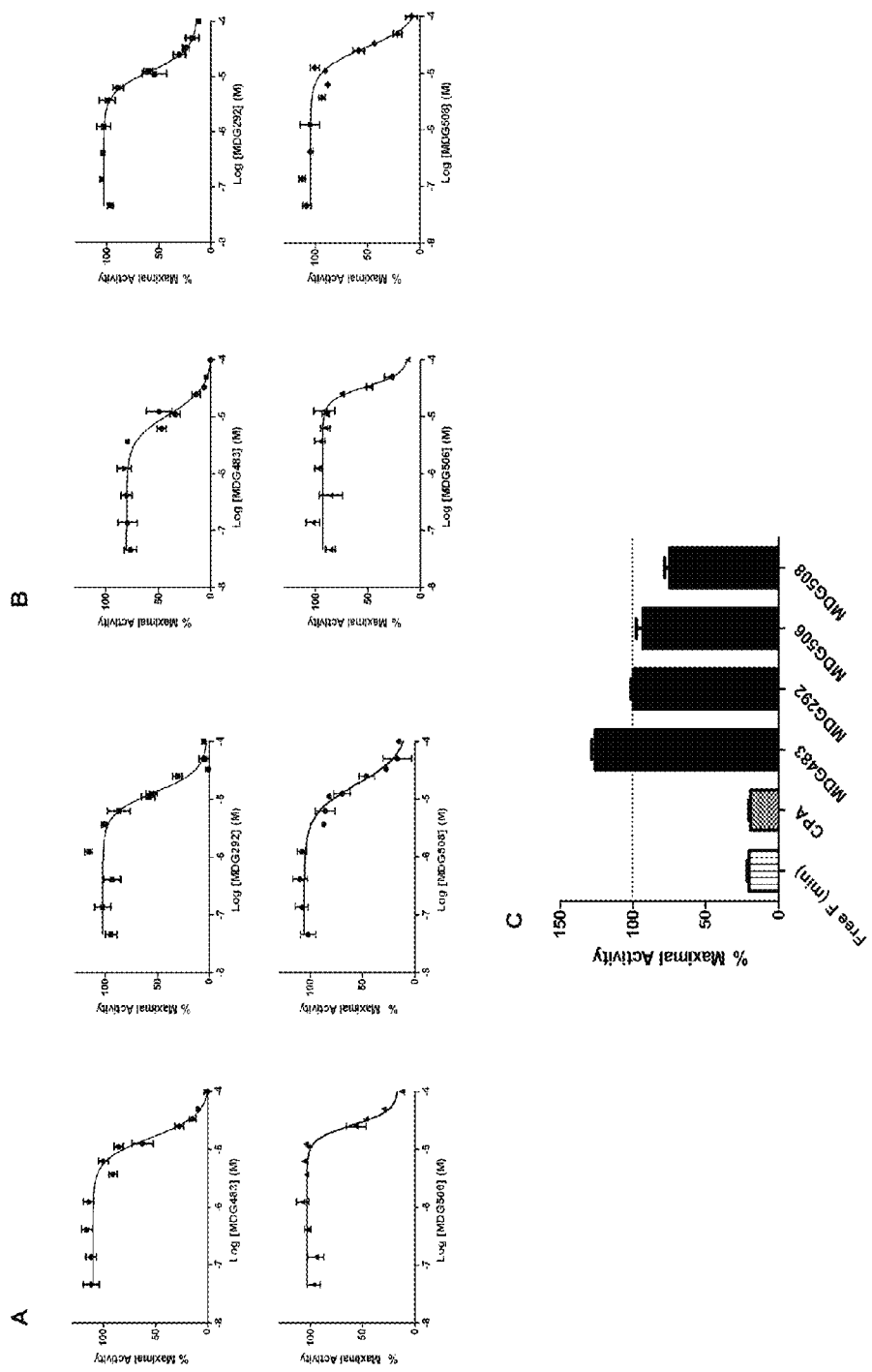
FIG. 2 illustrates the ability of Diarylhydrazides of the present invention to inhibit the AR recruitment of a D11-FxxLF peptide. (A) Compounds MDG292, MDG483, MDG506 & MDG508 tested in a TR-FRET assay across a concentration range from 100 µM to 45 nM in presence of a concentration of DHT=$EC_{80}$ in AR-LBD wt. Data points represent the mean of two independent experiments performed in triplicate. (B) Compounds MDG292, MDG483, MDG506 & MDG508 tested in a TR-FRET assay across a concentration range from 100 µM to 45 nM in presence of a concentration of DHT=$EC_{80}$ in AR-LBD T877A mutant. Data points represent the mean of two independent experiments performed in triplicate. (C) Fluorescence polarization data of MDG292, MDG483, MDG506 & MDG508 plotted as % Maximal Activity represented by AR-LBD and fluorophore complex (0% inhibition). Minimum control value represents free fluorophore (Free F) in solution (100% inhibition)
Figure 8A:
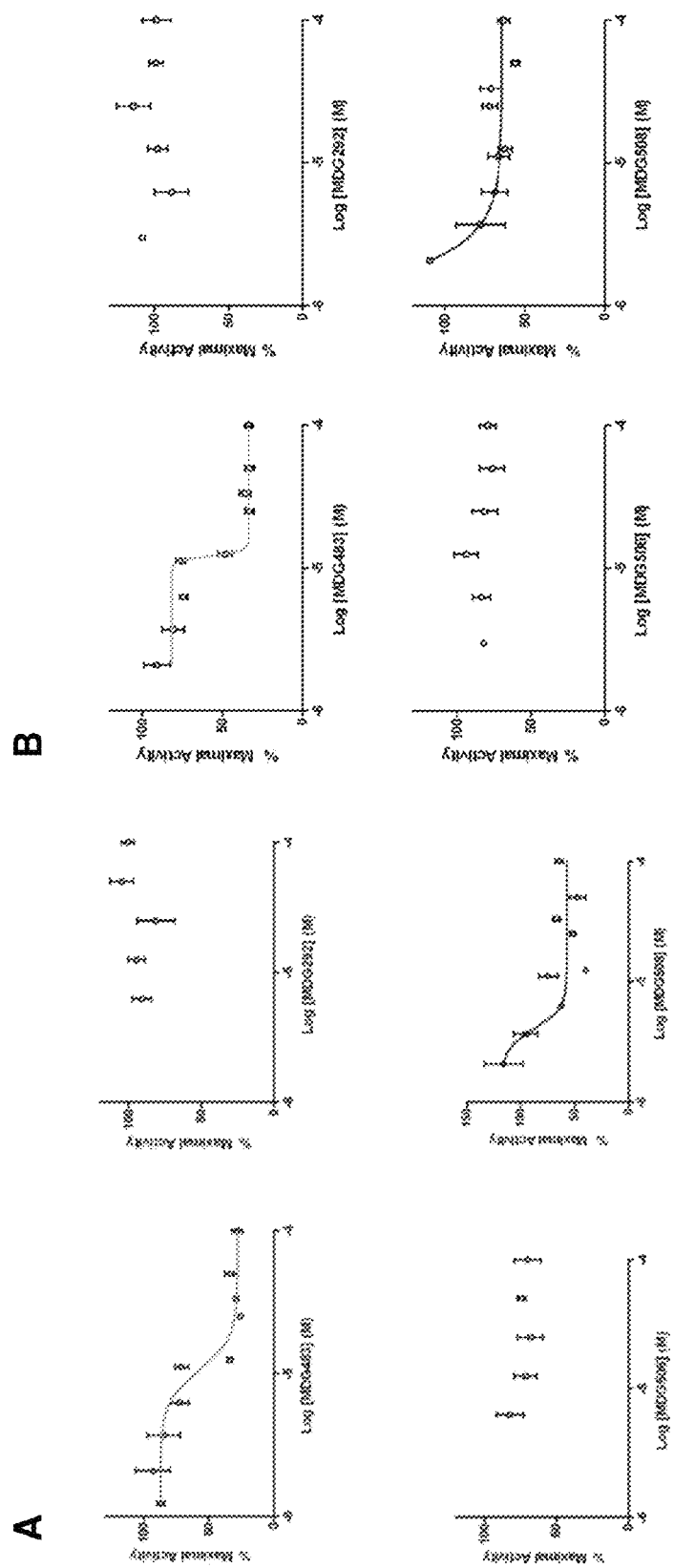
FIG. 8 illustrates the selectivity of Diarylhydrazides of the present invention amongst the steroid receptor subfamily (Estrogen Receptor Alpha and Beta, ERα & ERβ). (A) Diarylhydrazides MDG292, MDG483, MDG506 & MDG508 partially inhibit the ERα recruitment of a fluorescent labelled PGC1-α. Compounds were tested in a TR-FRET assay across a concentration range from 100 µM to 45 nM where applicable in presence of a concentration of Estradiol=$EC_{80}$. Data points represent the mean of two independent experiments performed in triplicate. Data was fitted using Log antagonist concentration vs response (variable slope). (B) Diarylhydrazides MDG292, MDG483, MDG506 & MDG508 partially inhibit the ERβ recruitment of a fluorescent labelled PGC1-α. Compounds were tested in a TR-FRET assay across a concentration range from 100 µM to 45 nM where applicable in presence of a concentration of Estradiol=$EC_{80}$. Data points represent the mean of two independent experiments performed in triplicate. Data was fitted using Log antagonist concentration vs response (variable slope). (C) Fluorescence polarization data of MDG483 & MDG508 plotted as % Maximal Activity represented by ERα LBD or ERβ LBD and fluorophore complex (0% inhibition). Minimum control value represents free fluorophore (Free F) in solution (100% inhibition).
Figure 8:
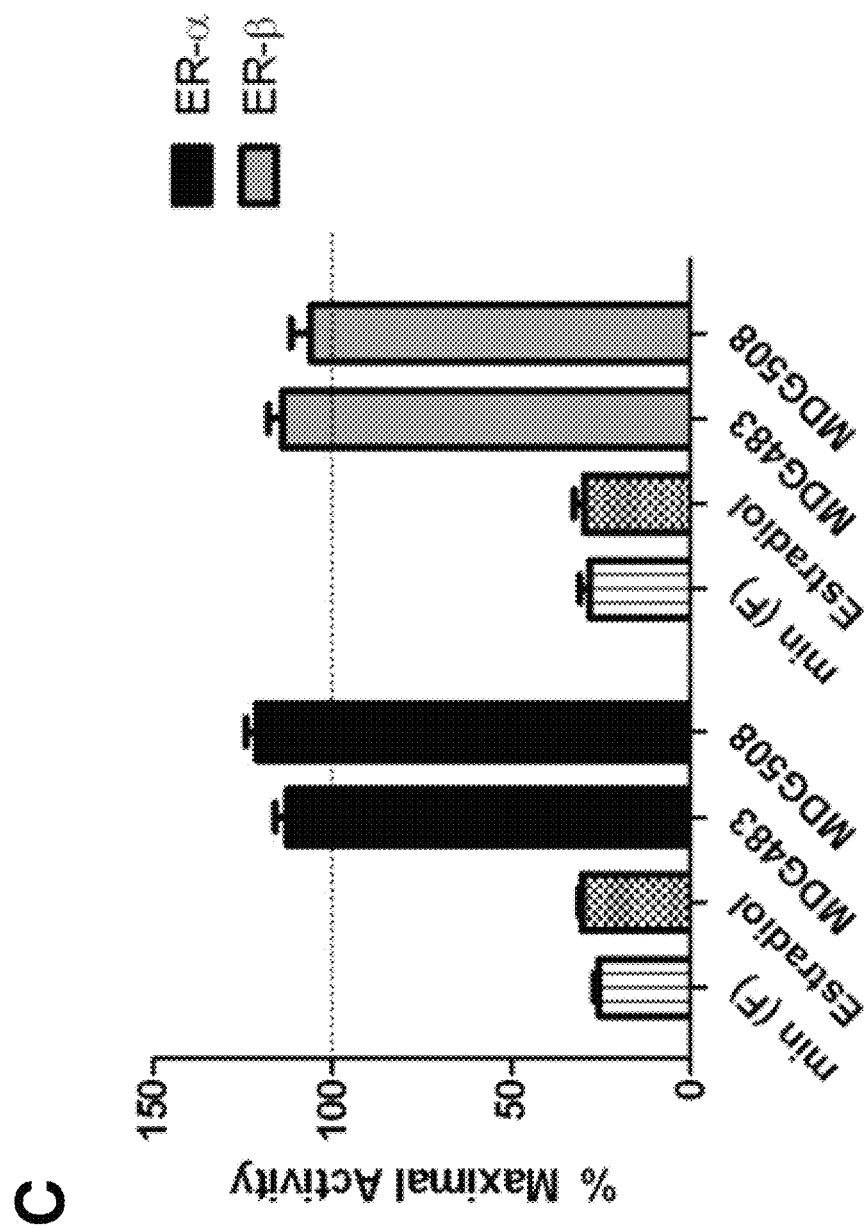
Figure 9:
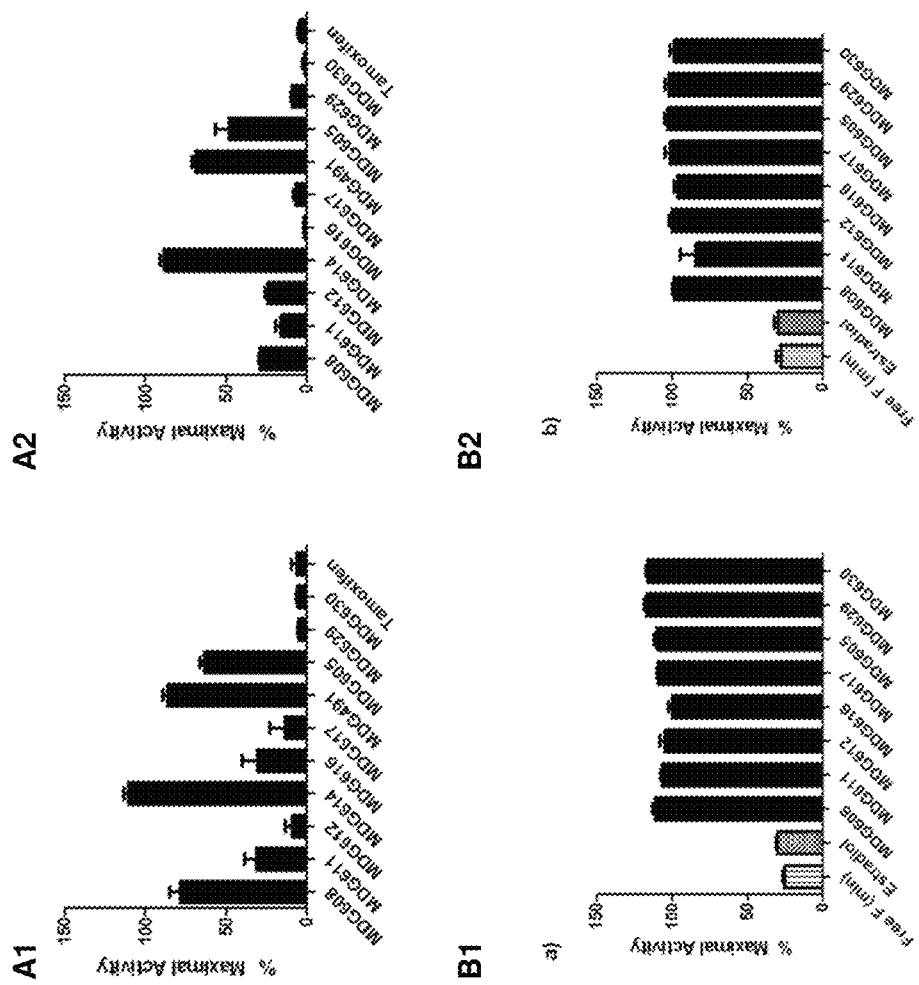
FIG. 9 illustrates the selectivity of Diarylhydrazides of the present invention amongst the steroid receptor subfamily (Estrogen Receptor Alpha and Beta, ERα & ERβ). (A) Diarylhydrazides MDG491, MDG605, MDG608, MDG611, MDG612, MDG614, MDG616, MDG617, MDG629 & MDG630 evaluated in the SAR study inhibit the ERα LBD (A1) and ERβ (B1) LBD recruitment of a fluorescent labelled PGC1-α coactivator. Compounds were tested in a TR-FRET assay at a maximal concentration of 100 µM in presence of a concentration of Estradiol=$EC_{80}$. Data points represent the mean of two independent experiments performed in triplicate. (B) Fluorescence polarization data of MDG605, MDG608, MDG611, MDG612, MDG616, MDG617, MDG629 & MDG630 plotted as % Maximal Activity represented by ERα LBD (B1) and ERβ LBD (B2) and fluorophore complex (0% inhibition). Minimum control value represents free fluorophore (Free F) in solution (100% inhibition)

Selectivity of the diarylhydrazide scaffold for the AR was determined through a TR-FRET assay in ERα (FIGS. 8A & 9A1) and ERR (FIGS. 8B & 9A2). Some of the diarylhydrazides investigated demonstrated partial antagonism in both isoforms of Estradiol bound ER LBD in recruiting a fluorescently labelled PGC-1α55 coactivator. The non-LBP nature of this inhibition was confirmed by a FP assay (FIGS. 9C, 9B1 & 9B2).

Biochemistry II (Cell Viability Studies: Cellular Compound Screening)

Diarylhydrazides Demonstrate Low Toxicity in Different Prostate Cancer Cellular Models'

To ascertain the translational (clinical) potential of these ligands, compounds were evaluated in cellular models of prostate cancer (LNCaP, an androgen-dependent cell line, PC-3, an androgen-independent cell line, and 22Rv1, a cell line representative of CRPC conditions) and in the 'normal' prostatic epithelia cell line PWR-1E.

Figure 10:
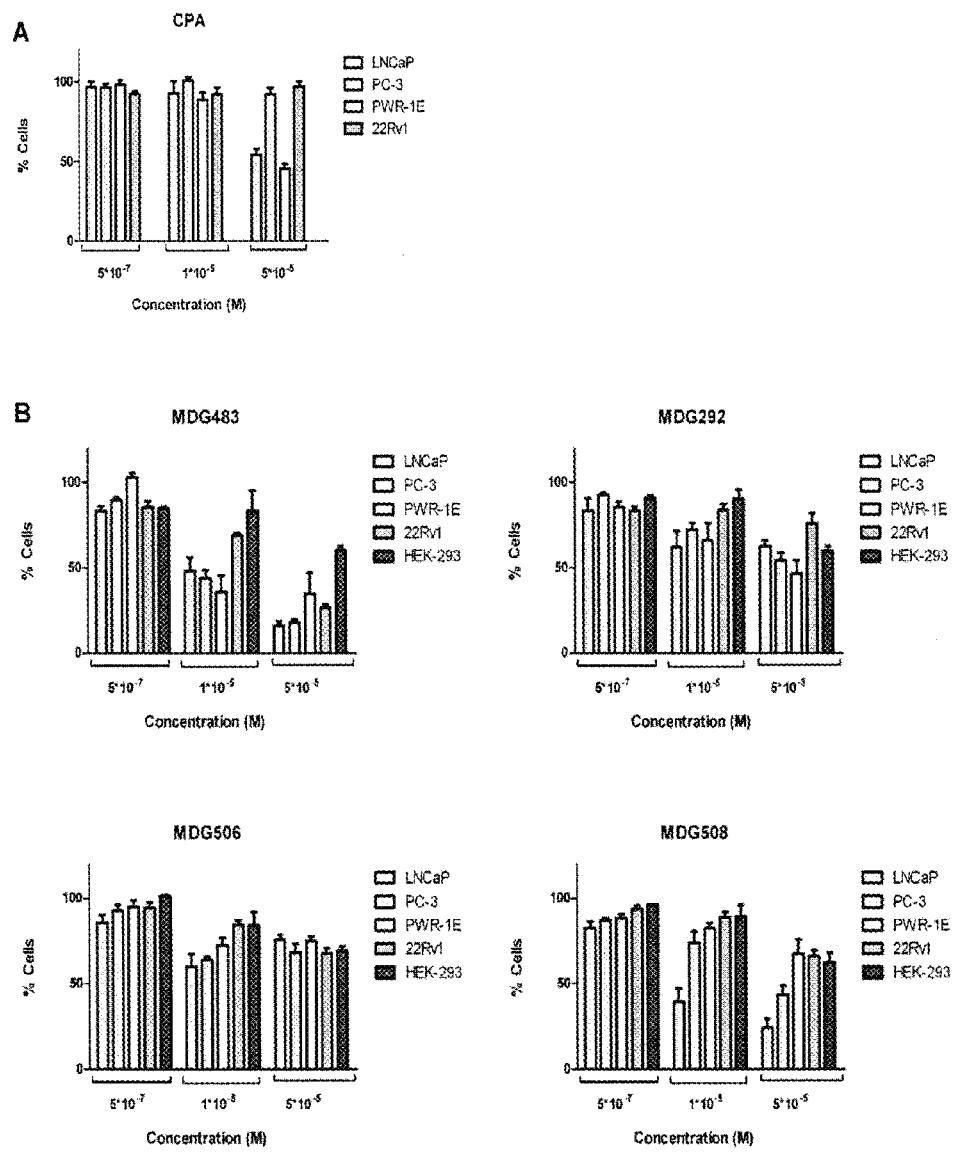
FIG. 10 illustrates the effect of Diarylhydrazides of the present invention on Cell Viability in LNCaP, PC-3, PWR-1E, 22Rv1 and HEK-293 cell lines. (A) Cyproterone Acetate (CPA) effect on cell viability at three point concentration. Cells were seeded at $2.5*10^4$/ml and treated with CPA 24 hours later. Results were evaluated following the AlamarBlue protocol 24 hours after treatment. Compounds dilutions were prepared from 200× stocks to achieve a final concentration of DMSO per well of 0.5%. Data plotted represent mean±SEM for at least three independent experiments where each well was performed in triplicate. (B) Diarylhydrazides effect (MDG292, MDG483, MDG506 & MDG508) on cell viability at three point concentration. Cells were seeded at $2.5*10^4$/ml and treated with the compounds 24 hours later. Results were evaluated following the AlamarBlue protocol 24 hours after treatment. Compounds dilutions were prepared from 200× stocks to achieve a final concentration of DMSO per well of 0.5%. Data plotted represent mean±SEM for at least three independent experiments where each well was performed in triplicate.

Cell viability was assessed after 24 hours of incubation with the test compounds initially at three different concentrations to establish their dose-responsiveness, considering 50 µM as the highest concentration (FIG. 10). The 'classical' antiandrogen CPA was used as a reference, which shows a minor effect at 50 µM in the androgen independent cell line PC-3 (FIG. 10A).

Figure 11:
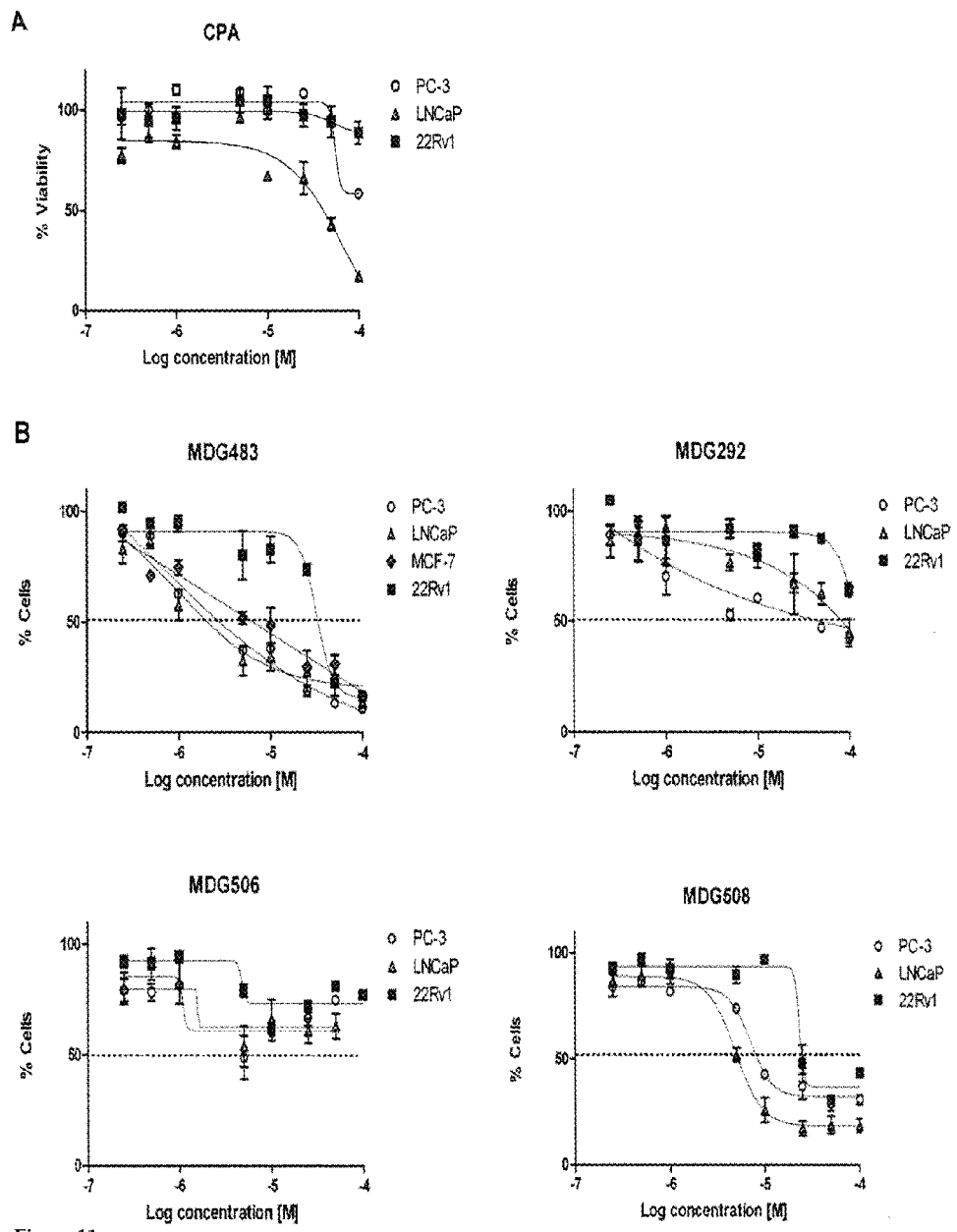
FIG. 11 illustrates the effect of Diarylhydrazides of the present invention on Cell Viability in LNCaP, PC-3, PWR-1E, 22Rv1 and HEK-293 cell lines. (A) Cyproterone Acetate (CPA) effect on cell viability at eight point concentration. Cells were seeded at $2.5*10^4$/ml and treated with CPA 24 hours later. Results were evaluated following the Alamar Blue protocol 24 hours after treatment. Compounds dilutions were prepared from 200× stocks to achieve a final concentration of DMSO per well of 0.5%. Data plotted represent mean±SEM for at least three independent experiments where each well was performed in triplicate. (B) Diarylhydrazides effect (MDG292, MDG483, MDG506 & MDG508) effect on cell viability at eight point concentration. Cells were seeded at $2.5*10^4$/ml and treated with compounds 24 hours later. Results were evaluated following the AlamarBlue protocol 24 hours after treatment. Compounds dilutions were prepared from 200× stocks to achieve a final concentration of DMSO per well of 0.5%. Data plotted represent mean±SEM for at least three independent experiments where each well was performed in triplicate.

In order to determine the IC50, compounds were evaluated in different cell lines at eight points of concentration (FIG. 11).

MDG506 Reduces DHT Dependent Cell Proliferation and PSA Expression in LNCaP

Figure 12:
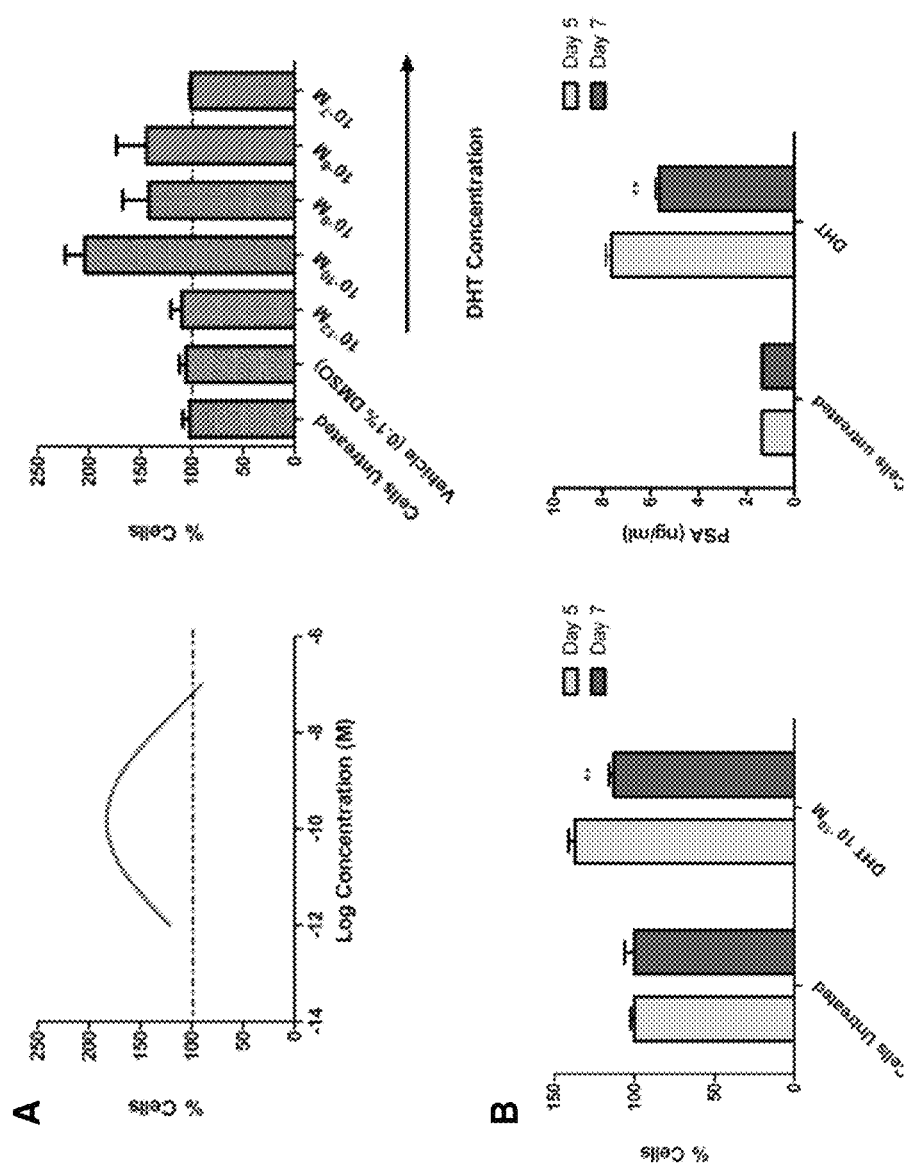
FIG. 12 illustrates the variance of DHT dependent cell proliferation and PSA expression in LNCaP cell lines. (A) DHT effect on LNCaP cell proliferation. Cells were seeded at $2*10^4$/ml and treated for five consecutive days after 48 hrs of equilibration in androgen deprived media. Media and treatment were replaced every second day or third day. DHT has a Gaussian type effect reaching a maximum of 2-fold increase at a concentration of $10^{-10}$M in 0.1% DMSO in steroid depleted conditions. Data plotted represent mean±SEM for at least three independent experiments where each well was performed in triplicate. (B) DHT effect on LNCaP cell proliferation is optimal after 5 days of treatment. Cells were seeded at $2*10^4$/ml in 24-well plates and treated for five or seven consecutive days after 48 hrs of equilibration in androgen deprived media. Media and treatment were replaced every second day or third day. There was a significant (P<0.01) reduction in viable cells and secreted PSA levels in the media after 7 days treatment with the same concentration of DHT as shown by two-way ANOVA analysis (Bonferroni post-test). Data plotted represent mean±SEM for at least three independent experiments where each well was performed in triplicate.

To determine the optimal DHT concentration and length of treatment required for cell proliferation assays, we tested a range of DHT concentrations in 0.1% DMSO for 5 or 7 days in LNCaP cells cultured in FBS stripped phenol red free media. We found that treatment with 0.1 nM DHT for 5 days to be the optimal conditions to stimulate LNCaP cell proliferation in absence of endogenous androgens. Media and treatments were replaced every second incubation day (FIGS. 12 A and B)

Figure 13:
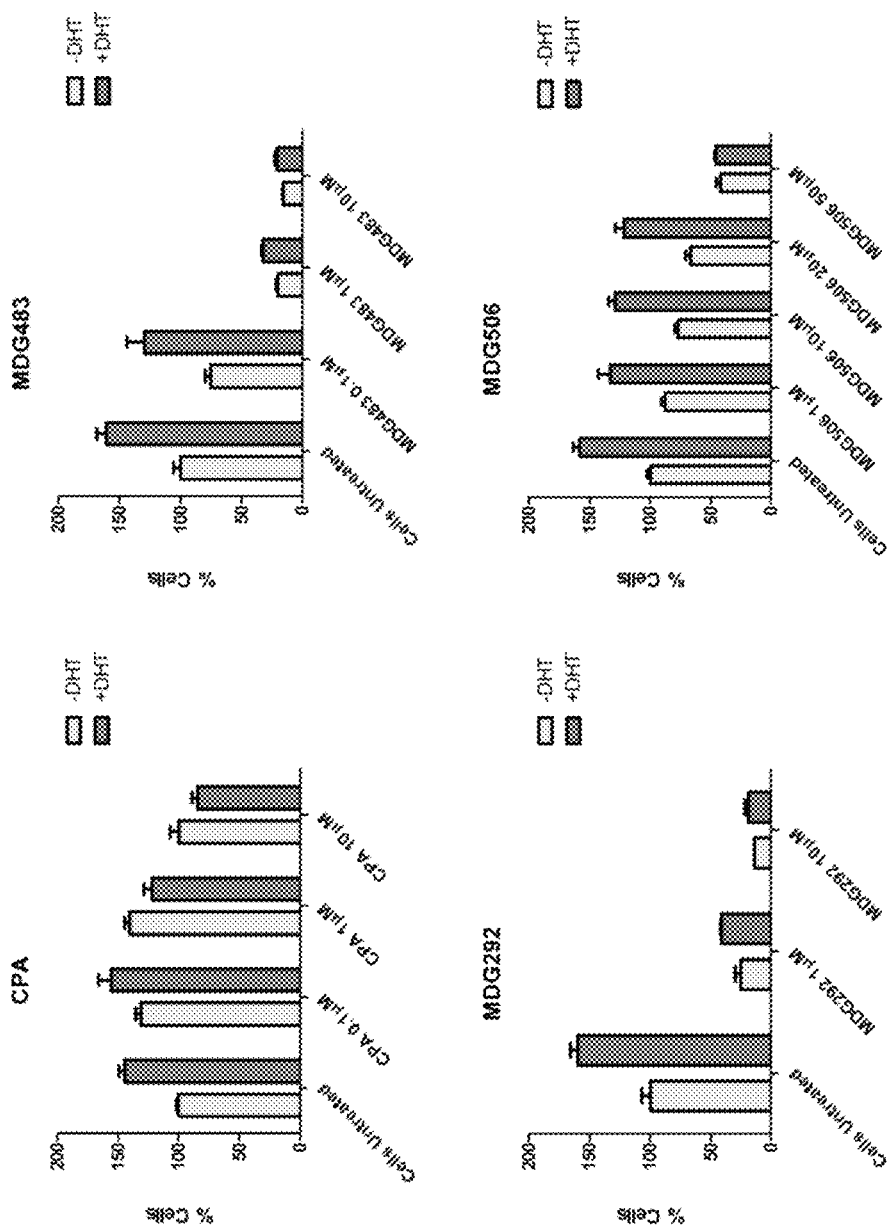
FIG. 13 illustrates the effect of Diarylhydrazides of the present invention on Cell Viability in LNCaP. Diarylhydrazides effect effect (MDG292, MDG483 & MDG506) on DHT stimulated LNCaP cell proliferation. Cells were seeded at $2*10^4$/ml in 24-well plates and treated for five consecutive days. Media and treatment were replaced every second day or third day. Data plotted represent mean±SEM for at least three independent experiments where each well was performed in triplicate.

We tested different concentrations of our test compounds (CPA, MDG292, MDG506 and MDG483) in presence or in absence of DHT 0.1 nM to investigate their dose-dependent inhibitory effects on LNCaP cell proliferation. We found that CPA induces cell proliferation in absence of DHT, and MDG506 has a clear dose dependent effect in reducing DHT dependent cell proliferation (FIG. 13)

Figure 14:
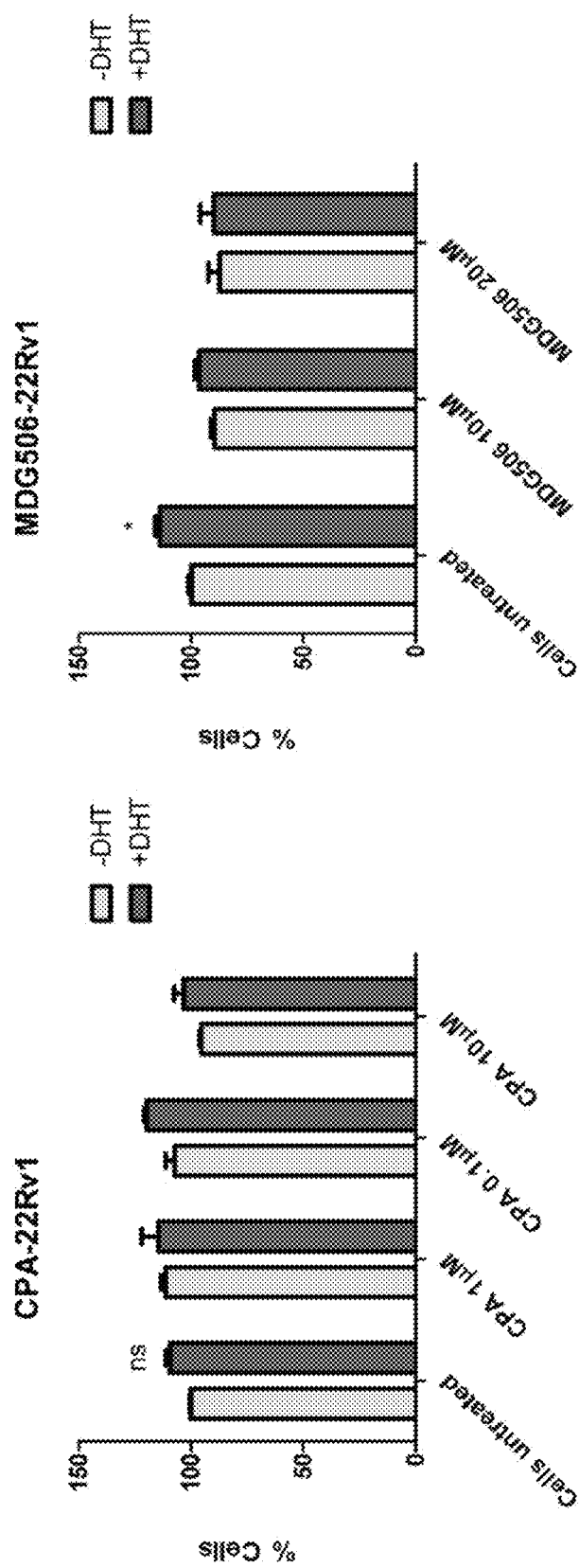
FIG. 14 illustrates the effect of Diarylhydrazides of the present invention on DHT stimulated 22Rv1 cell proliferation. CPA and MDG506 effect on DHT stimulated 22Rv1 cell proliferation. 22Rv1 cells were exposed to a concentration of DHT equal to $10^{-10}$M and viability was measured after five days of treatment in androgen deprived condition. Data plotted represent mean±SEM for at least three independent experiments where each well was performed in triplicate.

We tested MDG506 and CPA in another cell line, 22Rv1. This cell line possesses partial androgen-independent characteristics and does not respond to exogenous DHT stimulation. Thus, inhibition on cell proliferation by the compounds could not be evaluated (FIG. 14)

Figure 15:
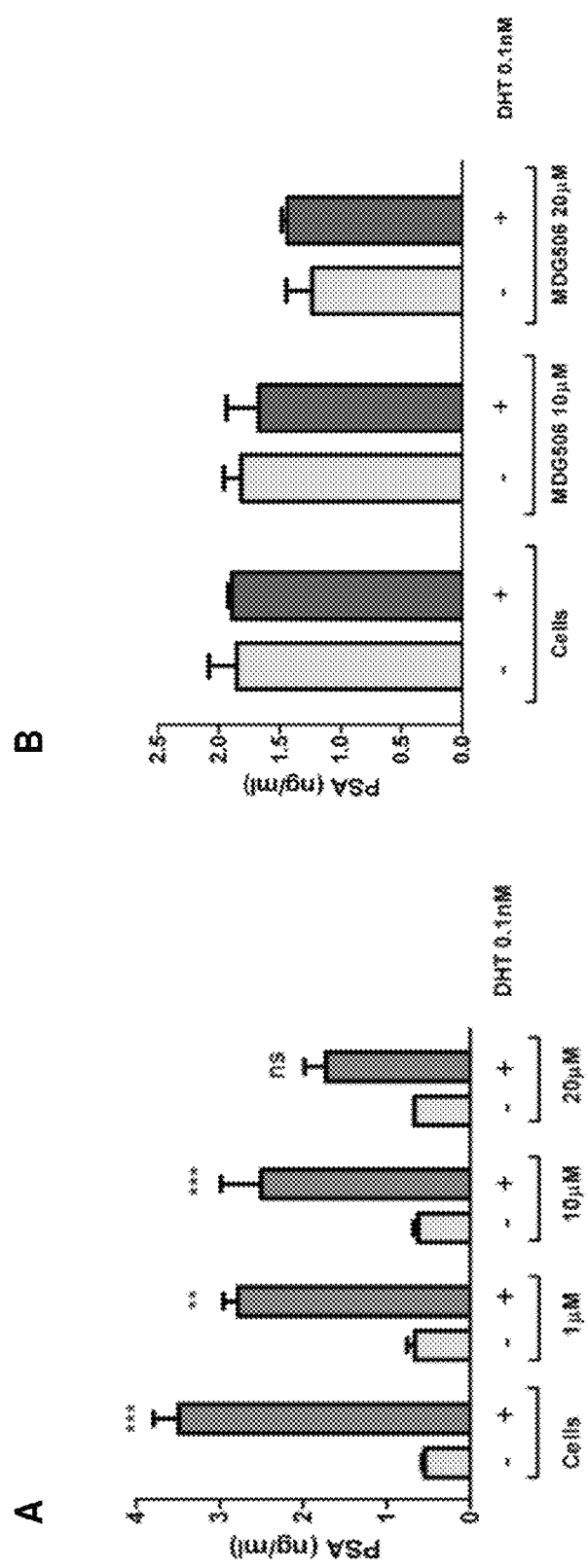
FIG. 15 illustrates the effect of Diarylhydrazides of the present invention on reduction of DHT dependent cell proliferation and PSA expression in LNCaP and 22Rv1 cell lines. (A) MDG506 dose dependent effect on DHT stimulated PSA secretion in LNCaP cells. Data plotted represent mean±SEM for at least three independent experiments where each well was performed in triplicate. (B) MDG506 dose dependent effect on DHT stimulated PSA secretion in 22Rv1 cells. Data plotted represent mean±SEM for at least three independent experiments where each well was performed in triplicate.

To investigate compounds effect on PSA expression, a common biomarker for prostate cancer, we utilized a human PSA ELISA assay. We found that in LNCaP (FIG. 15A) we have dose dependent inhibition of PSA expression at MDG506 concentrations up to 20 µM. The same experiment was repeated in 22Rv1 cells, but no effect could be seen as this cell line does not express PSA depending on DHT stimulation (FIG. 15B)

MDG506 Reduces CPA Stimulated PSA Expression in LNCaP and 22Rv1 Cells

Figure 16:
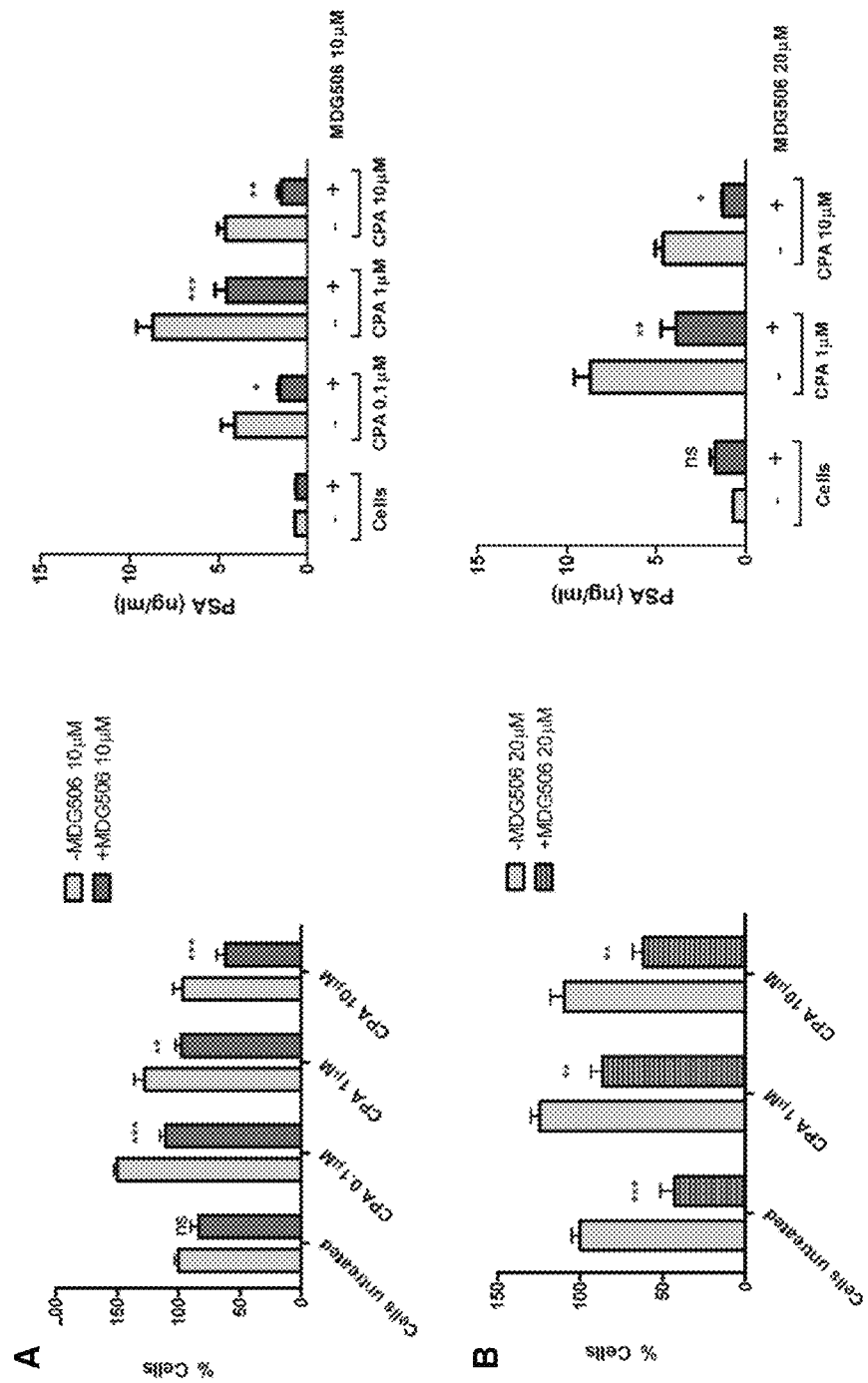
FIG. 16 illustrates the effect of Diarylhydrazides of the present invention on reduction of CPA stimulated PSA expression in LNCaP. (A) MDG506 10 µM dose dependent effect on CPA stimulated PSA secretion in LNCaP cells. CPA effect on LNCaP PSA secretion is bell-shaped, reaching a maximal stimulatory concentration at 1 µM. MDG506 significantly (P<0.001) reduces CPA induction of PSA secretion. Data plotted represent mean±SEM for at least three independent experiments where each well was performed in triplicate. (B) MDG506 20 µM dose dependent effect on CPA stimulated PSA secretion in LNCaP cells. Data plotted represent mean±SEM for at least three independent experiments where each well was performed in triplicate.

Since we found that CPA stimulates cell proliferation in absence of endogenous androgens, we evaluated if MDG506 at different concentrations could block this effect. We performed a cell proliferation assay and a PSA ELISA assay in presence of MDG506 at 10 or 20 µM (FIGS. 16A and 16B). MDG506 reduces CPA induced cell proliferation and PSA expression. In contrast with CPA'S behaviour, MDG506 does not induce cell proliferation or PSA expression in absence of androgens, lacking intrinsic agonistic activity.

Figure 17:
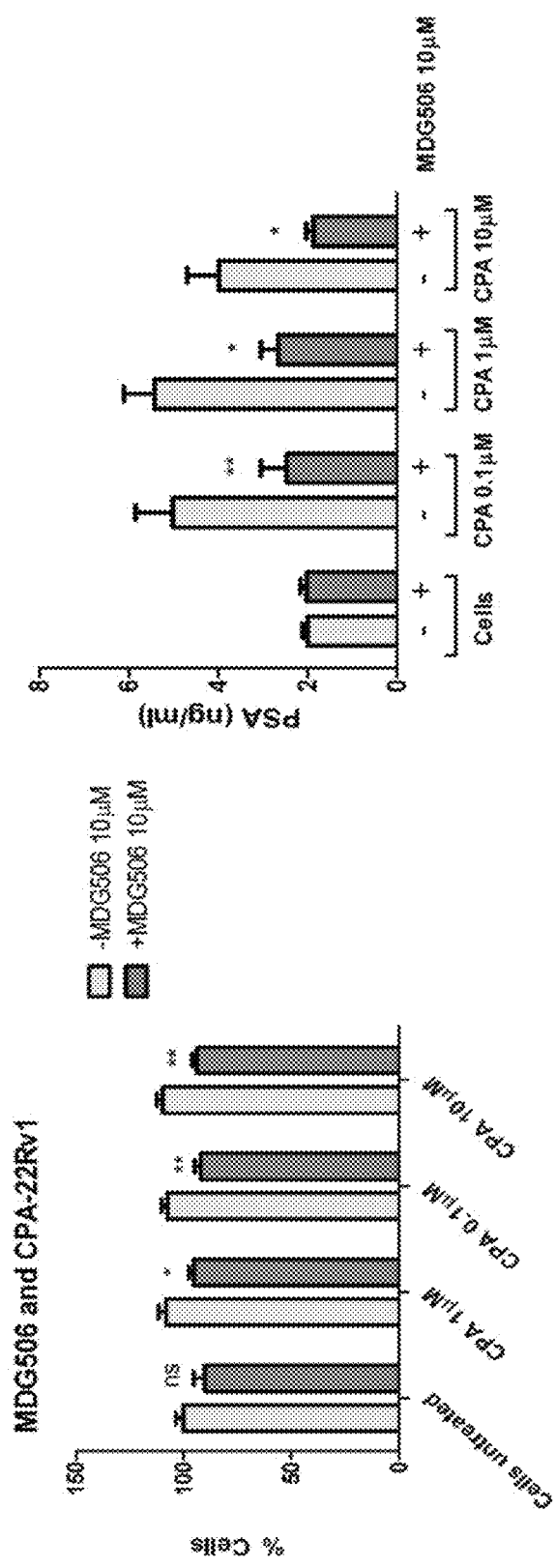
FIG. 17 illustrates the effect of Diarylhydrazides of the present invention on reduction of CPA stimulated PSA expression in 22rv1 cells. MDG506 10 µM dose dependent effect on CPA stimulated PSA secretion in 22rv1 cells. Data plotted represent mean±SEM for at least three independent experiments where each well was performed in triplicate.

We repeated the same experiment in 22Rv1 cell line. Although we couldn't see a remarkable increase in cell proliferation, we observed a remarkable increase in PSA expression by CPA, which was indeed reduced by MDG506 at different concentrations. Again, in contrast with CPA'S behaviour, MDG506 does not induce cell proliferation or PSA expression in absence of androgens (FIG. 17)

Additional Activity Data

| COMPOUND | Supplier | Supplier_ID | Structure | Activity (AR wt TR-FRET) |
|---|---|---|---|---|
| MDG15 | SPECS | AN-988/40680570 | 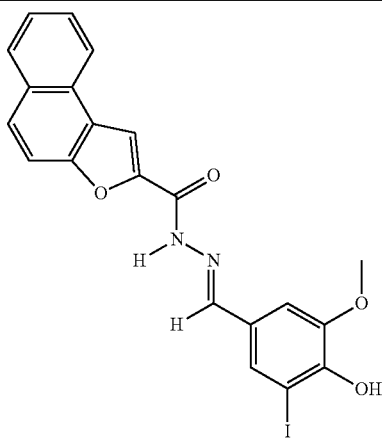 | 43.2 µM |
| MDG173 | SPECS | AK-968/11482603 | 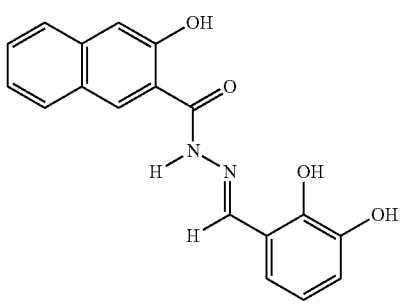 [SMILES: O=C(N/N=C/c1cccc(O)c1O)c1cc2ccccc2cc1O] | 40.8 ± 2.5 µM |
| MDG292 | SPECS | AE-848/34517025 | 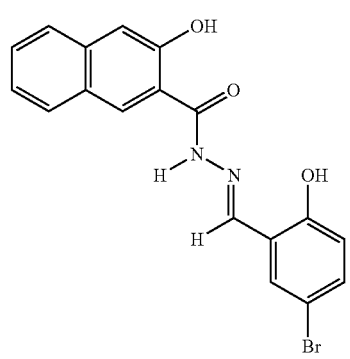 | 13.3 ± 3.1 µM |
| MDG481 | SPECS | AG-205/06971039 | 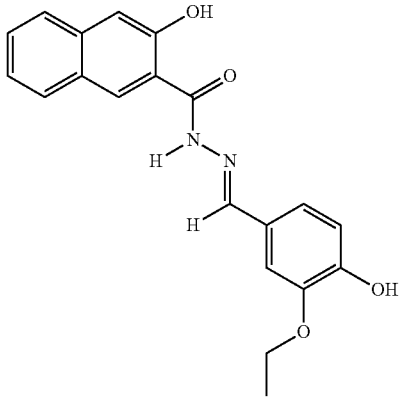 [SMILES: CCOc1cc(/C=N/NC(=O)c2cc3ccccc3cc2O)ccc1O] | >100 µM |

| COMPOUND | Supplier | Supplier_ID | Structure | Activity (AR wt TR-FRET) |
|---|---|---|---|---|
| MDG482 | SPECS | AG-205/32388043 | 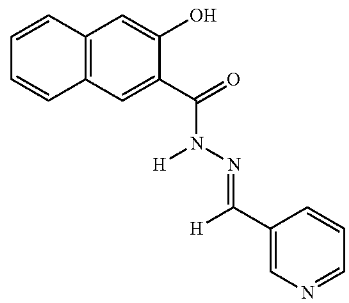 [SMILES: O=C(N/N=C/c1cccnc1)c1cc2ccccc2cc1O] | >100 μM |
| MDG483 | SPECS | AG-690/11156274 | 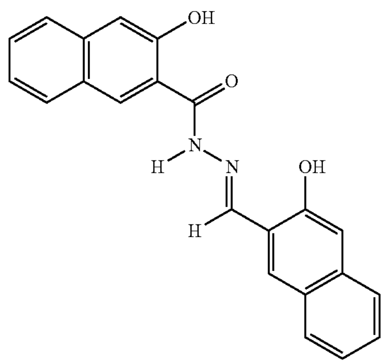 [SMILES: O=C(N/N=C/c1cc2ccccc2cc1O)c1cc2ccccc2cc1O] | 15.9 ± 3.2 μM |
| MDG484 | SPECS | AG-690/11191237 | 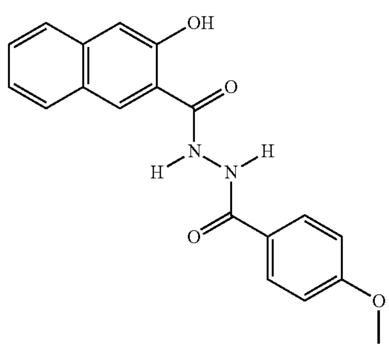 [SMILES: COc1ccc(C(=O)NNC(=O)c2cc3ccccc3cc2O)cc1] | >100 μM |
| MDG485 | SPECS | AG-690/11450109 | 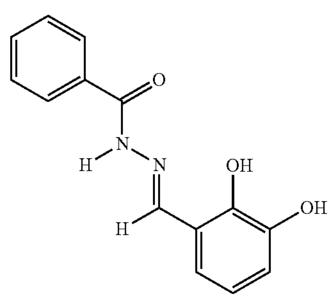 [SMILES: O=C(N/N=C/c1cccc(O)c1O)c1ccccc1] | >100 μM |

| COMPOUND | Supplier | Supplier_ID | Structure | Activity (AR wt TR-FRET) |
|---|---|---|---|---|
| MDG486 | SPECS | AG-690/11450119 | 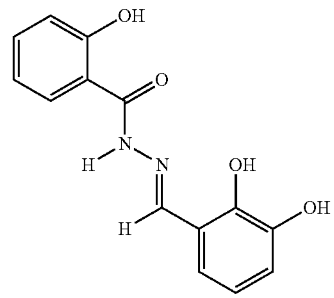 [SMILES: O=C(N/N=C/c1cccc(O)c1O)c1ccccc1O] | >100 μM |
| MDG487 | SPECS | AK-968/40052375 | 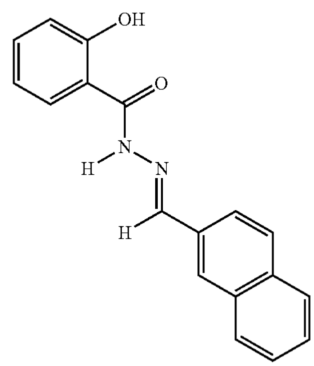 [SMILES: O=C(N/N=C/c1ccc2ccccc2c1)c1ccccc1O] | >100 μM |
| MDG488 | SPECS | AK-968/40225178 | 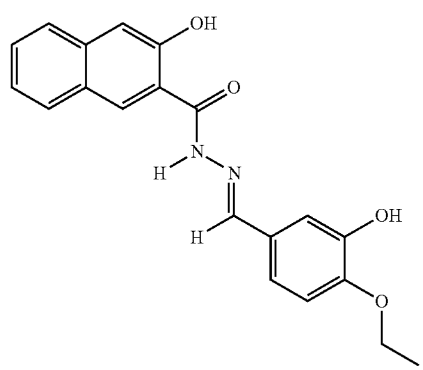 [SMILES: CCOc1ccc(/C=N/NC(=O)c2cc3ccccc3cc2O)cc1O] | >100 μM |
| MDG489 | SPECS | AK-968/40320181 | 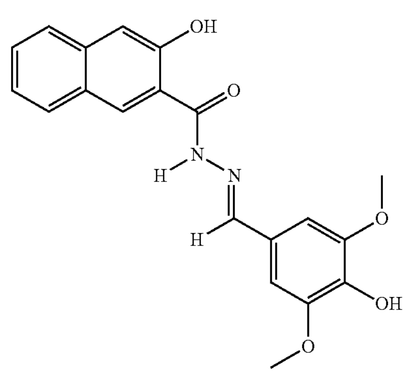 [SMILES: COc1cc(/C=N/NC(=O)c2cc3ccccc3cc2O)cc(OC)c1O] | >100 μM |

| COM-POUND | Supplier | Supplier_ID | Structure | Activity (AR wt TR-FRET) |
|---|---|---|---|---|
| MDG490 | SPECS | AK-968/40660142 | 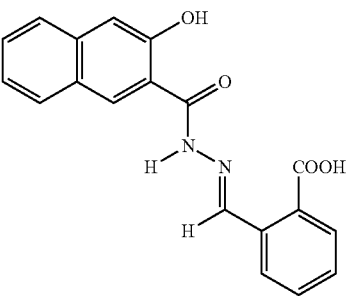 [SMILES: O=C(N/N=C/c1ccccc1C(=O)O)c1cc2ccccc2cc1O] | >100 μM |
| MDG491 | SPECS | AN-329/10500005 | 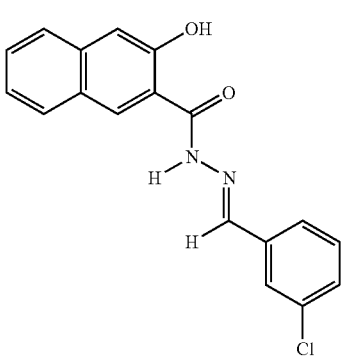 [SMILES: O=C(N/N=C/c1cccc(Cl)c1)c1cc2ccccc2cc1O] | 42.7 ± 3.5 μM |
| MDG492 | SPECS | AN-329/11481807 | 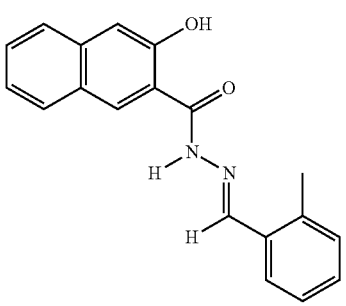 [SMILES: Cc1ccccc1/C=N/NC(=O)c1cc2ccccc2cc1O] | >100 μM |
| MDG493 | SPECS | AN-329/11481810 | 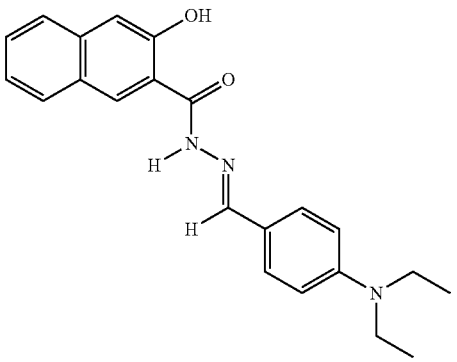 [SMILES: CCN(CC)c1ccc(/C=N/NC(=O)c2cc3ccccc3cc2O)cc1] | >100 μM |

-continued

| COMPOUND | Supplier | Supplier_ID | Structure | Activity (AR wt TR-FRET) |
|---|---|---|---|---|
| MDG494 | SPECS | AN-329/11481813 | 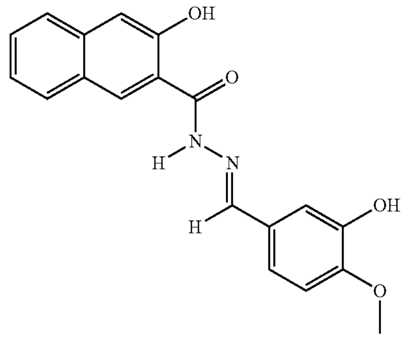 [SMILES: COc1ccc(/C=N/NC(=O)c2cc3ccccc3cc2O)cc1O] | >100 μM |
| MDG495 | SPECS | AN-329/11481815 | 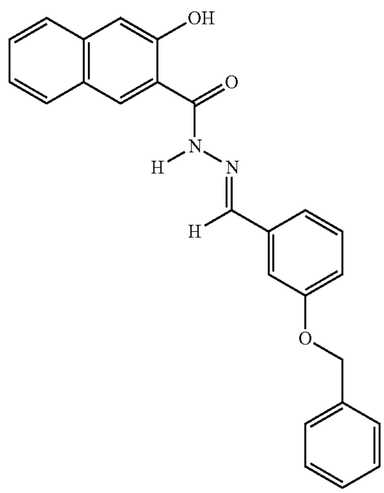 [SMILES: O=C(N/N=C/c1cccc(OCc2ccccc2)c1)c1cc2ccccc2cc1O] | >100 μM |
| MDG496 | SPECS | AN-329/11482595 | 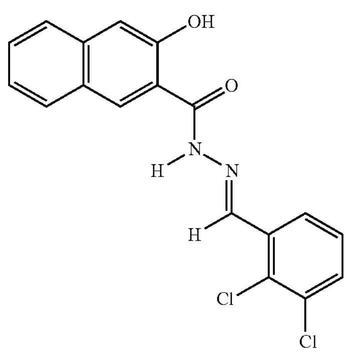 [SMILES: O=C(N/N=C/c1cccc(Cl)c1Cl)c1cc2ccccc2cc1O] | >100 μM |
| MDG497 | SPECS | AN-329/11482596 | 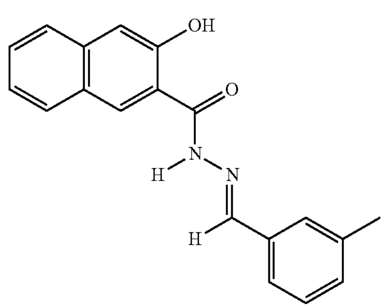 [SMILES: Cc1cccc(/C=N/NC(=O)c2cc3ccccc3cc2O)c1] | >100 μM |

-continued

| COMPOUND | Supplier | Supplier_ID | Structure | Activity (AR wt TR-FRET) |
|---|---|---|---|---|
| MDG499 | SPECS | AN-988/40679770 | 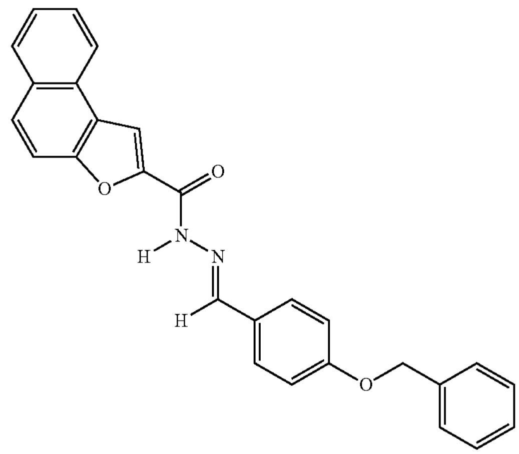 [SMILES: O=C(N/N=C/c1ccc(OCc2ccccc2)cc1)c1cc2c(ccc3ccccc32)o1] | >100 μM |
| MDG500 | SPECS | AN-988/40679802 | 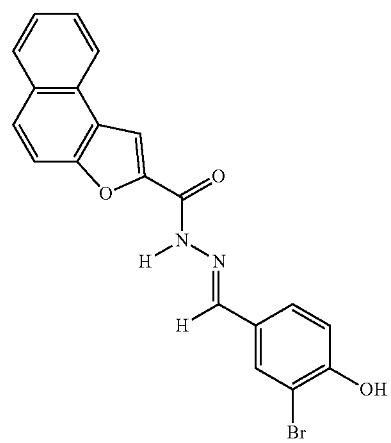 [SMILES: O=C(N/N=C/c1ccc(O)c(Br)c1)c1cc2c(ccc3ccccc32)o1] | >100 μM |
| MDG501 | SPECS | AN-988/40679809 | 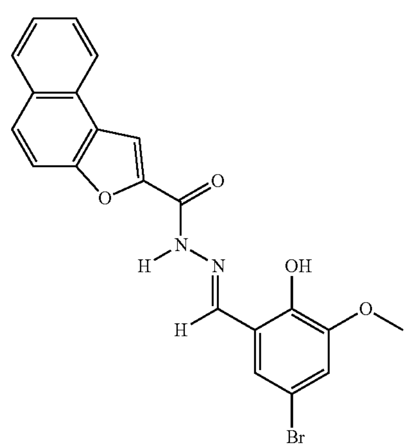 [SMILES: COc1cc(Br)cc(/C=N/NC(=O)c2cc3c(ccc4ccccc43)o2)c1O] | >100 μM |

-continued

| COMPOUND | Supplier | Supplier_ID | Structure | Activity (AR wt TR-FRET) |
|---|---|---|---|---|
| MDG502 | SPECS | AN-988/40679916 | 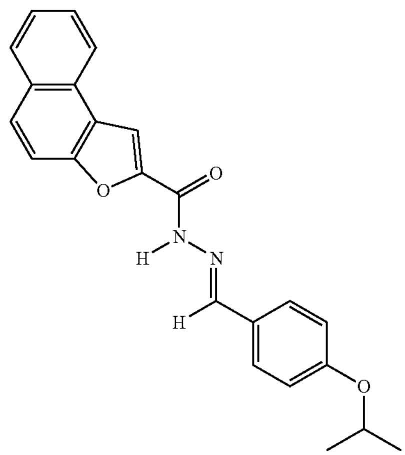 [SMILES: CC(C)Oc1ccc(/C=N/NC(=O)c2cc3c(ccc4ccccc43)o2)cc1] | >100 μM |
| MDG503 | SPECS | AN-988/40679917 | 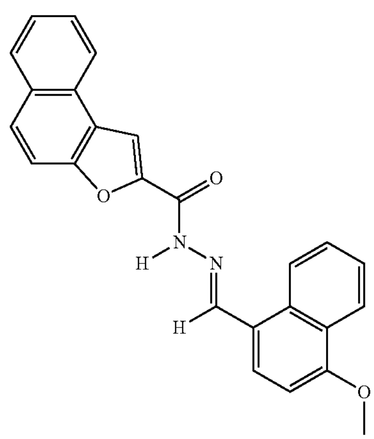 [SMILES: COc1ccc(/C=N/NC(=O)c2cc3c(ccc4ccccc43)o2)c2ccccc12] | >100 μM |
| MDG504 | SPECS | AN-988/40679919 | 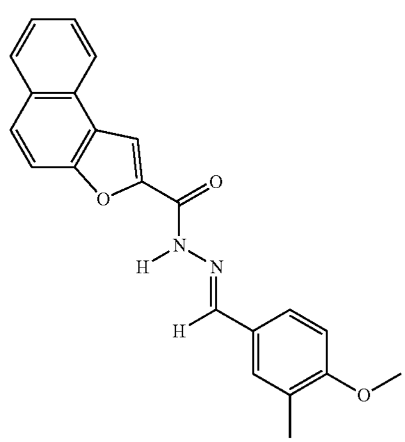 [SMILES: COc1ccc(/C=N/NC(=O)c2cc3c(ccc4ccccc43)o2)cc1C] | >100 μM |

-continued

| COM-POUND | Supplier | Supplier_ID | Structure | Activity (AR wt TR-FRET) |
|---|---|---|---|---|
| MDG505 | SPECS | AN-988/40679923 | 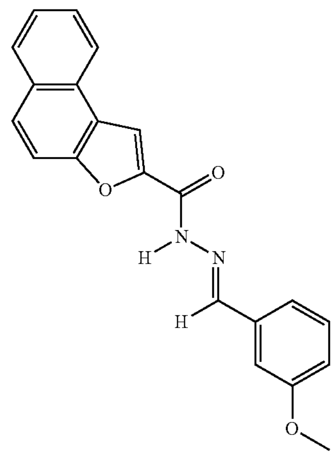 [SMILES: COc1cccc(/C=N/NC(=O)c2cc3c(ccc4ccccc43)o2)c1] | >100 μM |
| MDG506 | SPECS | AN-988/40679931 | 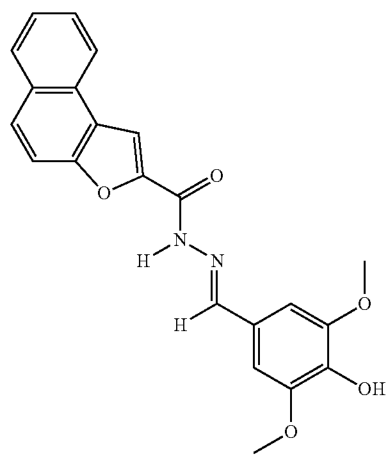 [SMILES: COc1cc(/C=N/NC(=O)c2cc3c(ccc4ccccc43)o2)cc(OC)c1O] | 26.3 ± 3.8 μM |
| MDG507 | SPECS | AN-988/40680452 | 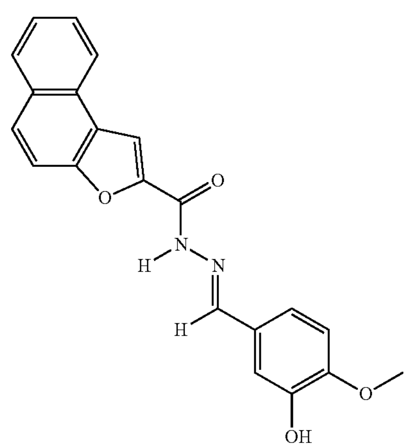 [SMILES: COc1ccc(/C=N/NC(=O)c2cc3c(ccc4ccccc43)o2)cc1O] | >100 μM |

| COM-POUND | Supplier | Supplier_ID | Structure | Activity (AR wt TR-FRET) |
|---|---|---|---|---|
| MDG508 | SPECS | AN-988/40680498 | 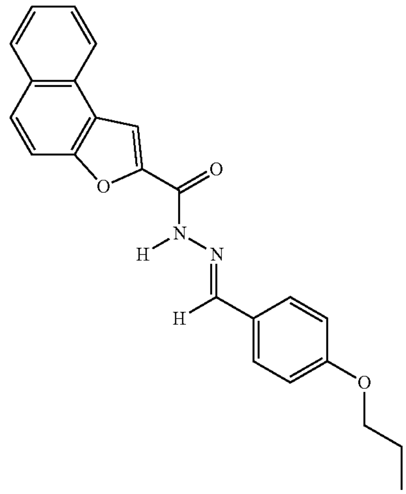 [SMILES: CCCOc1ccc(/C=N/NC(=O)c2cc3c(ccc4ccccc43)o2)cc1] | 17.9 ± 6.9 μM |
| MDG509 | SPECS | AN-988/40680500 | 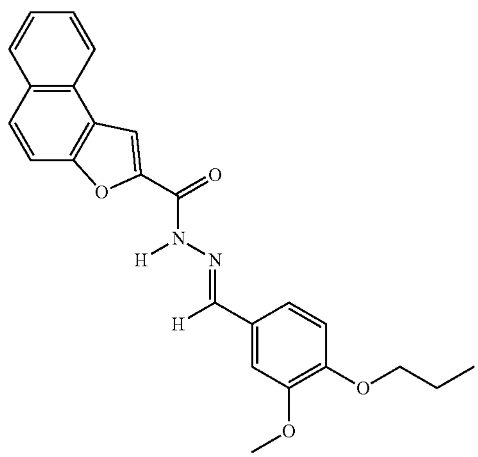 [SMILES: CCCOc1ccc(/C=N/NC(=O)c2cc3c(ccc4ccccc43)o2)cc1OC] | >100 μM |
| MDG510 | SPECS | AN-988/40680503 | 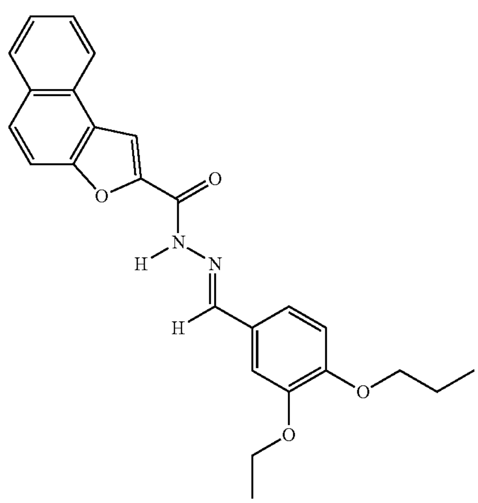 [SMILES: CCCOc1ccc(/C=N/NC(=O)c2cc3c(ccc4ccccc43)o2)cc1OCC] | >100 μM |

-continued

| COMPOUND | Supplier | Supplier_ID | Structure | Activity (AR wt TR-FRET) |
|---|---|---|---|---|
| MDG511 | SPECS | AN-988/40680531 | 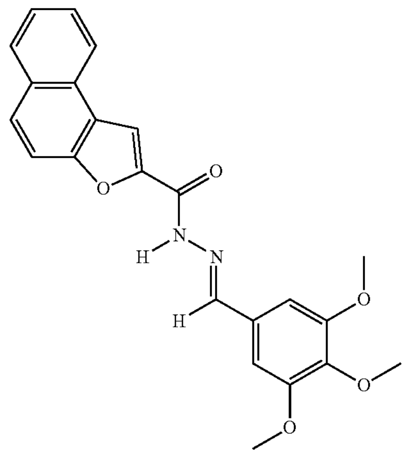 [SMILES: COc1cc(/C=N/NC(=O)c2cc3c(ccc4ccccc43)o2)cc(OC)c1OC] | >100 μM |
| MDG512 | SPECS | AN-988/40680532 | 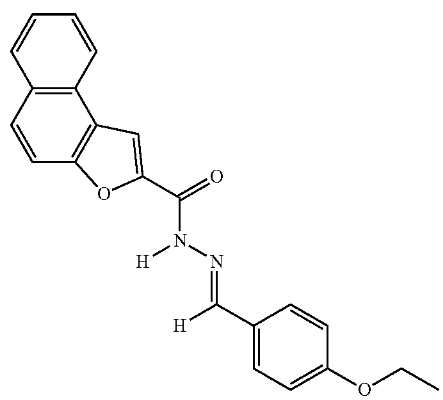 [SMILES: CCOc1ccc(/C=N/NC(=O)c2cc3c(ccc4ccccc43)o2)cc1] | >100 μM |
| MDG513 | SPECS | AN-988/40680546 | 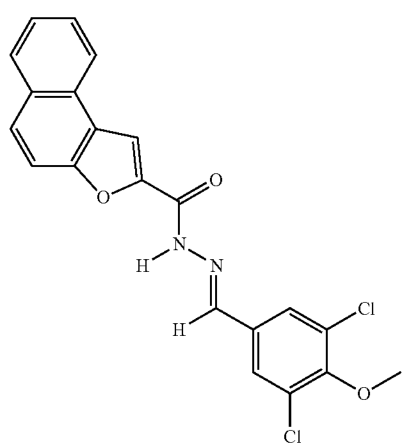 [SMILES: COc1c(Cl)cc(/C=N/NC(=O)c2cc3c(ccc4ccccc43)o2)cc1Cl] | >100 μM |

| COM-POUND | Supplier | Supplier_ID | Structure | Activity (AR wt TR-FRET) |
|---|---|---|---|---|
| MDG514 | SPECS | AN-988/40680547 | 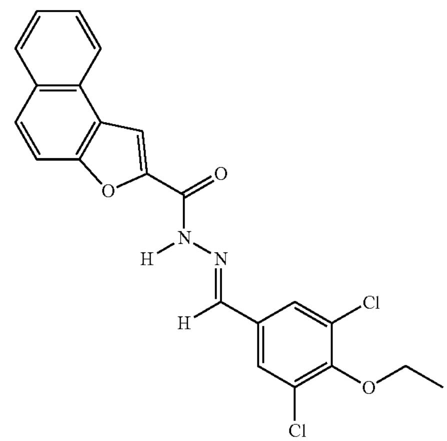 [SMILES: CCOc1c(Cl)cc(/C=N/NC(=O)c2cc3c(ccc4ccccc43)o2)cc1Cl] | >100 μM |
| MDG515 | SPECS | AN-988/40680562 | 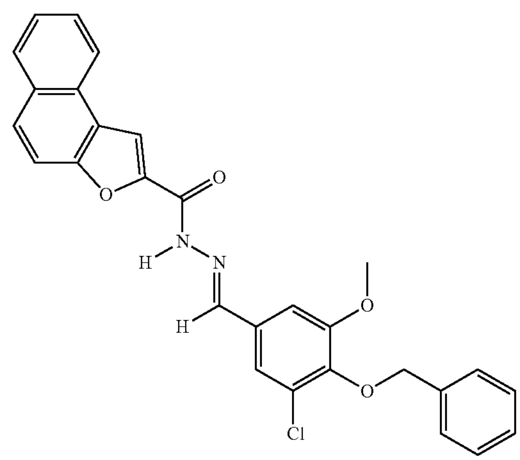 [SMILES: COc1cc(/C=N/NC(=O)c2cc3c(ccc4ccccc43)o2)cc(Cl)c1OCc1ccccc1] | >100 μM |
| MDG516 | SPECS | AN-988/40680571 | 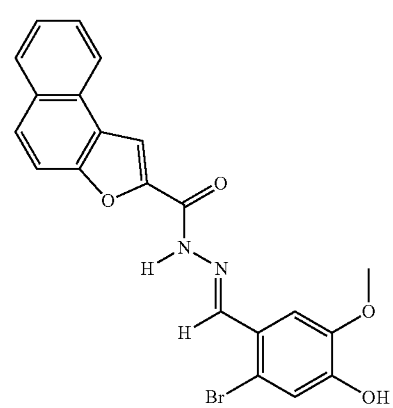 [SMILES: COc1cc(/C=N/NC(=O)c2cc3c(ccc4ccccc43)o2)c(Br)cc1O] | >100 μM |

-continued

| COM-POUND | Supplier | Supplier_ID | Structure | Activity (AR wt TR-FRET) |
|---|---|---|---|---|
| MDG598 | SPECS | AN-648/41220887 | 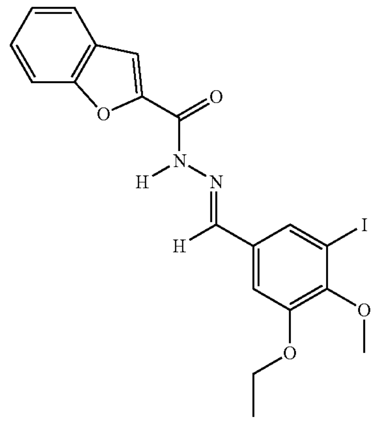 [SMILES: CCOc1cc(/C=N/NC(=O)c2cc3ccccc3o2)cc(I)c1OC] | >100 μM |
| MDG599 | Chembridge | 8806676 | 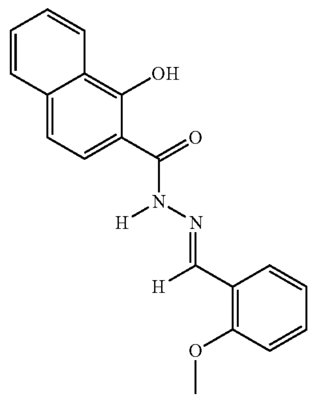 [SMILES: COc1ccccc1/C=N/NC(=O)c1ccc2ccccc2c1O] | >100 μM |
| MDG600 | Chembridge | 5113192 | 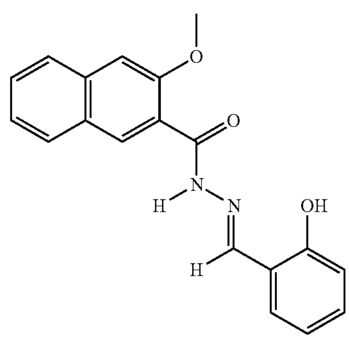 [SMILES: COc1cc2ccccc2cc1C(=O)N/N=C/c1ccccc1O] | >100 μM |
| MDG601 | Chembridge | 5238483 | 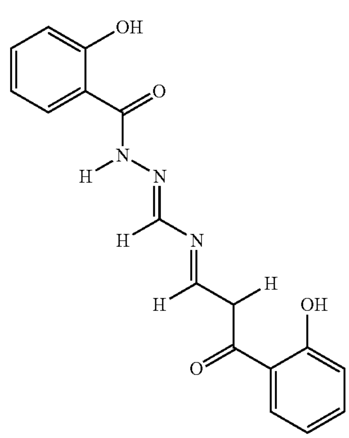 [SMILES: O=C(C/C=N/C=N/NC(=O)c1ccccc1O)c1ccccc1O] | >100 μM |

-continued

| COMPOUND | Supplier | Supplier_ID | Structure | Activity (AR wt TR-FRET) |
|---|---|---|---|---|
| MDG602 | Chembridge | 5331730 | 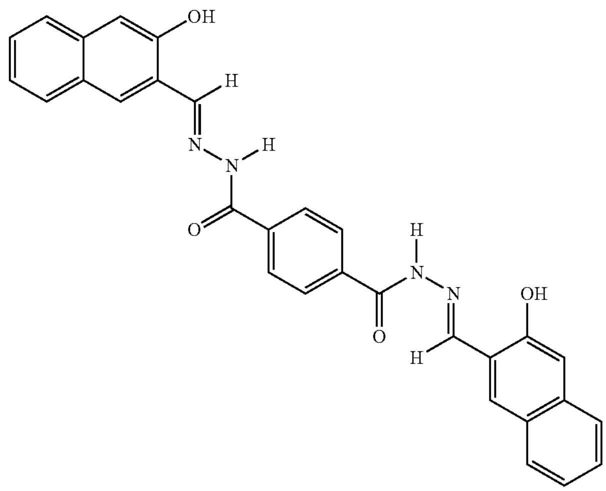 [SMILES: O=C(N/N=C/c1cc2ccccc2cc1O)c1ccc(C(=O)N/N=C/c2cc3ccccc3cc2O)cc1] | >100 μM |
| MDG603 | Chembridge | 5660431 | 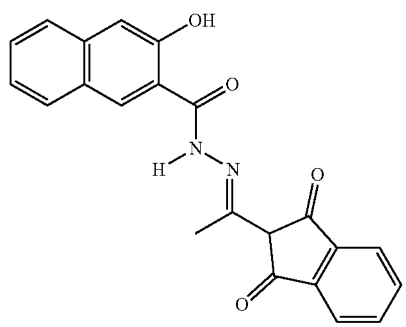 [SMILES: C/C(=N\NC(=O)c1cc2ccccc2cc1O)C1C(=O)c2ccccc2C1=O] | 11.3 ± 2.6 μM |
| MDG604 | Chembridge | 5653834 | 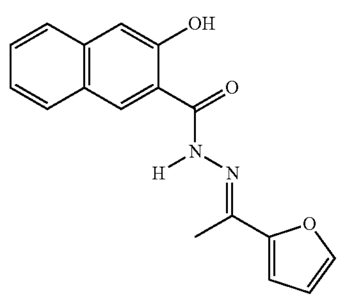 [SMILES: C/C(=N\NC(=O)c1cc2ccccc2cc1O)c1ccco1] | >100 μM |
| MDG605 | Chembridge | 5367002 | 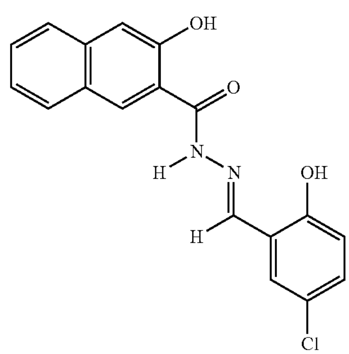 [SMILES: O=C(N/N=C/c1cc(Cl)ccc1O)c1cc2ccccc2cc1O] | 10.3 ± 1.4 μM |

-continued

| COMPOUND | Supplier | Supplier_ID | Structure | Activity (AR wt TR-FRET) |
|---|---|---|---|---|
| MDG607 | Chembridge | 5327458 | 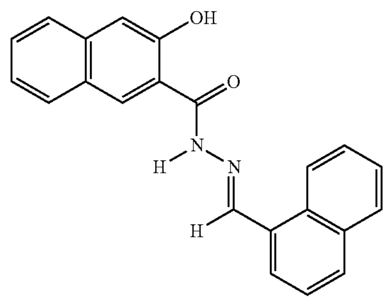 [SMILES: O=C(N/N=C/c1cccc2ccccc12)c1cc2ccccc2cc1O] | >100 μM |
| MDG608 | MDG Laboratory | MDG608 | 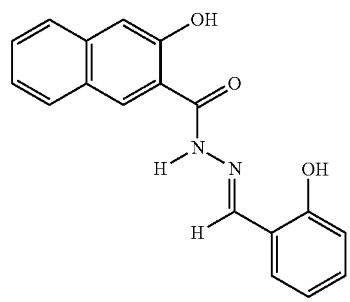 [SMILES: O=C(N/N=C/c1ccccc1O)c1cc2ccccc2cc1O] | 55.2 ± 19.2 μM |
| MDG609 | MDG Laboratory | MDG609 | 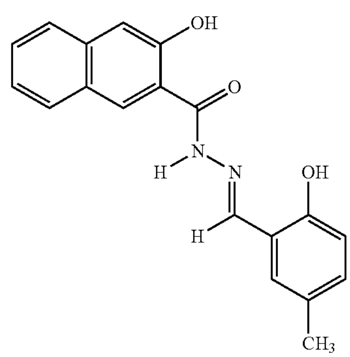 | >100 μM |
| MDG610 | MDG Laboratory | MDG610 | 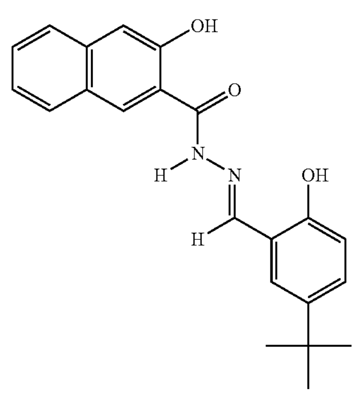 [SMILES: CC(C)(C)c1ccc(O)c(/C=N/NC(=O)c2cc3ccccc3cc2O)c1] | >100 μM |

| COMPOUND | Supplier | Supplier_ID | Structure | Activity (AR wt TR-FRET) |
|---|---|---|---|---|
| MDG611 | MDG Laboratory | MDG611 | (3-hydroxy-naphthalene-2-carbohydrazide with 2,5-dihydroxybenzylidene) | 39.9 ± 16.9 µM |
| MDG612 | MDG Laboratory | MDG612 | (3-hydroxy-naphthalene-2-carbohydrazide with 2-hydroxy-5-methoxybenzylidene) | 52.9 ± 13.5 µM |
| MDG613 | MDG Laboratory | MDG613 | (3-hydroxy-naphthalene-2-carbohydrazide with 2-hydroxy-5-iodobenzylidene) | >100 µM |
| MDG614 | MDG Laboratory | MDG614 | (3-hydroxy-naphthalene-2-carbohydrazide with 2-hydroxy-5-nitrobenzylidene) | 33.4 ± 4.7 µM |

| COM-POUND | Supplier | Supplier_ID | Structure | Activity (AR wt TR-FRET) |
|---|---|---|---|---|
| MDG615 | MDG Laboratory | MDG615 | 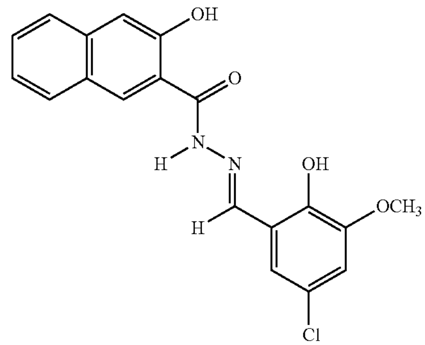 [SMILES: COc1cc(Cl)cc(/C=N/NC(=O)c2cc3ccccc3cc2O)c1O] | >100 µM |
| MDG616 | MDG Laboratory | MDG616 | 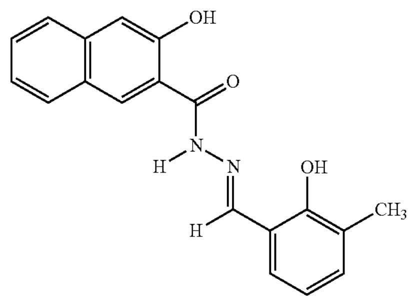 [SMILES: Cc1cccc(/C=N/NC(=O)c2cc3ccccc3cc2O)c1O] | 13.2 ± 2.8 µM |
| MDG617 | MDG Laboratory | MDG617 | 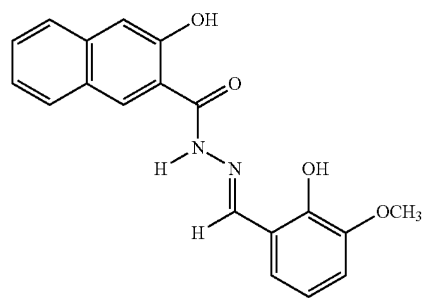 [SMILES: COc1cccc(/C=N/NC(=O)c2cc3ccccc3cc2O)c1O] | 12.2 ± 0.5 µM |
| MDG618 | MDG Laboratory | MDG618 | 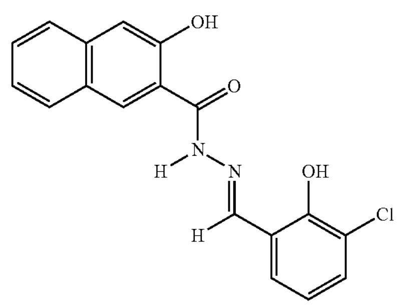 [SMILES: O=C(N/N=C/c1cccc(Cl)c1O)c1cc2ccccc2cc1O] | >200 µM |
| MDG619 | MDG Laboratory | MDG619 | 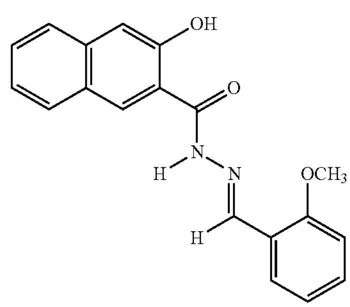 [SMILES: COc1ccccc1/C=N/NC(=O)c1cc2ccccc2cc1O] | >100 µM |

| COM-POUND | Supplier | Supplier_ID | Structure | Activity (AR wt TR-FRET) |
|---|---|---|---|---|
| MDG620 | MDG Laboratory | MDG620 | 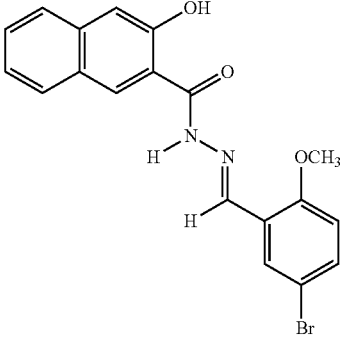 [SMILES: COc1ccc(Br)cc1/C=N/NC(=O)c1cc2ccccc2cc1O] | >100 μM |
| MDG621 | MDG Laboratory | MDG621 | 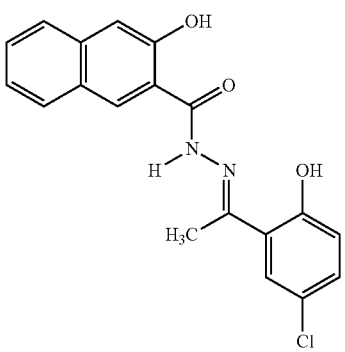 [SMILES: C/C(=N\NC(=O)c1cc2ccccc2cc1O)c1cc(Cl)ccc1O] | >100 μM |
| MDG622 | MDG Laboratory | MDG622 | 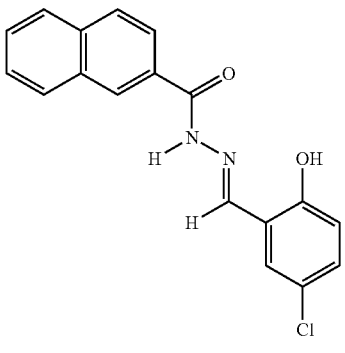 [SMILES: O=C(N/N=C/c1cc(Cl)ccc1O)c1ccc2ccccc2c1] | >100 μM |
| MDG623 | SPECS | AN-329/11482602 | 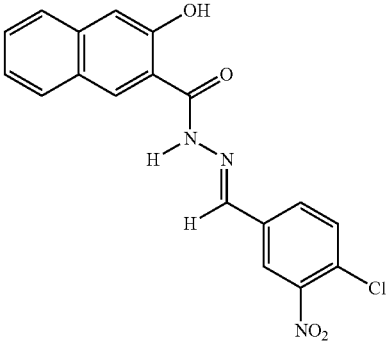 [SMILES: O=C(N/N=C/c1ccc(Cl)c([N+](=O)[O-])c1)c1cc2ccccc2cc1O] | >100 μM |

-continued
| COMPOUND | Supplier | Supplier_ID | Structure | Activity (AR wt TR-FRET) |
|---|---|---|---|---|
| MDG624 | MDG Laboratory | MDG624 | 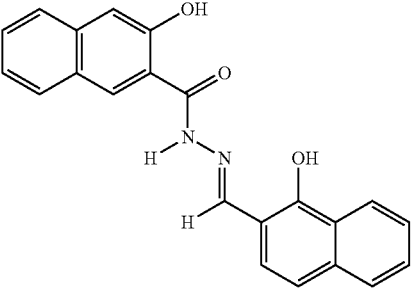 [SMILES: O=C(N/N=C/c1ccc2ccccc2c1O)c1cc2ccccc2cc1O] | >100 μM |
| MDG625 | MDG Laboratory | MDG625 | 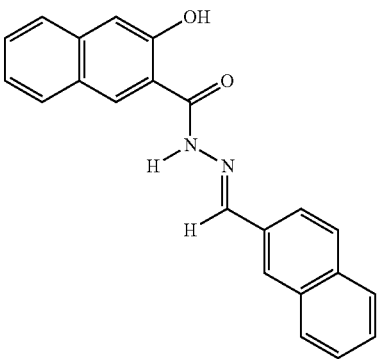 [SMILES: O=C(N/N=C/c1ccc2ccccc2c1)c1cc2ccccc2cc1O] | >100 μM |
| MDG626 | MDG Laboratory | MDG626 | 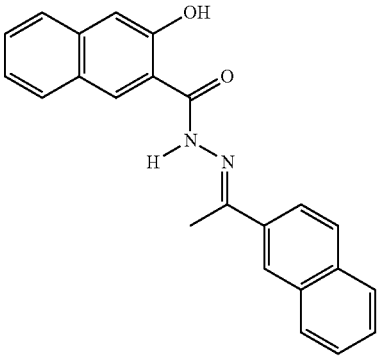 [SMILES: C/C(=N\NC(=O)c1cc2ccccc2cc1O)c1ccc2ccccc2c1] | >100 μM |
| MDG627 | MDG Laboratory | MDG627 | 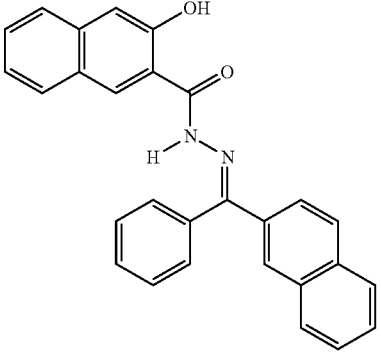 [SMILES: O=C(N/N=C(\c1ccccc1)c1ccc2ccccc2c1)c1cc2ccccc2cc1O] | >100 μM |

-continued

| COMPOUND | Supplier | Supplier_ID | Structure | Activity (AR wt TR-FRET) |
|---|---|---|---|---|
| MDG628 | MDG Laboratory | MDG628 | 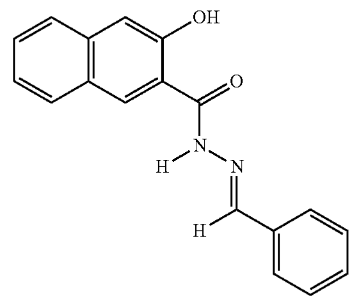 [SMILES: O=C(N/N=C/c1ccccc1)c1cc2ccccc2cc1O] | >100 μM |
| MDG629 | MDG Laboratory | MDG629 | 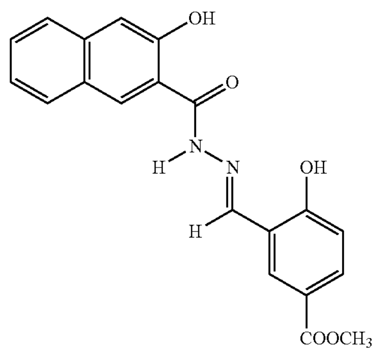 [SMILES: COC(=O)c1ccc(O)c(/C=N/NC(=O)c2cc3ccccc3cc2O)c1] | 60.76 μM |
| MDG630 | MDG Laboratory | MDG630 | 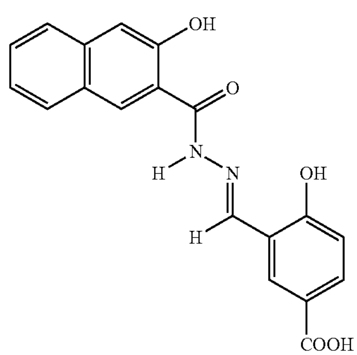 [SMILES: O=C(O)c1ccc(O)c(/C=N/NC(=O)c2cc3ccccc3cc2O)c1] | 43.5 ± 3.7 μM |
| MDG631 | MDG Laboratory | MDG631 | 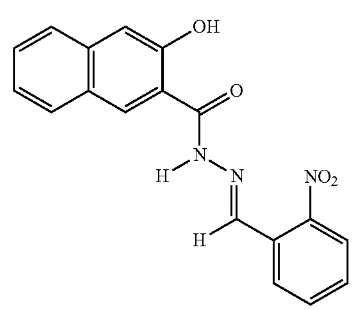 [SMILES: Nc1ccccc1/C=N/NC(=O)c1cc2ccccc2cc1O] | >100 μM |

-continued

| COMPOUND | Supplier | Supplier_ID | Structure | Activity (AR wt TR-FRET) |
|---|---|---|---|---|
| MDG632 | MDG Laboratory | MDG632 | [naphthalene-OH with C(=O)-NH-N=CH-(2-aminophenyl)] | >100 μM |
| MDG633 | MDG Laboratory | MDG633 | [naphthalene-OH with C(=O)-NH-N=CH-(2-NO₂-5-Cl-phenyl)] | >100 μM |

Materials and Methods
Time-Resolved Fluorescence Resonance Energy Transfer (TR-FRET) Assay Lanthascreen TR-FRET AR Coactivator Assay kit (Invitrogen, cat no. PV4381) was used to screen for potential coactivator disruptors. Black low volume 384-wells assay plates (Corning, N.Y., cat no. 3676) were used to perform the assay (total volume 20 μl) and TR FRET signal measured with PHERAstar equipment (BMG LabTech) using a Lanthascreen optic module excitation 335 nm, emission 520 nm-channel A and 495 nm-channel B.

TR FRET values were calculated at 10 flashes per well, using a delay time of 100 μs and integration time 200 μs as recommended by the Invitrogen assay guidelines. The ratio 520 nm/495 nm was then calculated and plotted against the concentration. A serial dilution of compounds was firstly prepared in 100×DMSO (Sigma-Aldrich) starting from the maximum desired concentration to achieve a 12 point range concentration using 96-well polypropylene plates (Nalgene Nunc, Rochester, N.Y.). Each 100× solution was diluted to 2× concentration with TR-FRET co-regulator buffer A (Invitrogen proprietary buffer), yielding a final concentration of 1% DMSO in each well. 10 μl of 2× solution was then added to the 384 well plate, following addition of 5 μl 4×AR-LBD and 5 μl of D11-FxxLF/Tb Anti-GST antibody in agonist mode and 5 μl of D11-FxxLF/Tb anti-GST antibody/DHT (Included at a concentration equal to $EC_{80}$ as determined by running the assay in agonist mode first).

$$EC_{80}=10^{((\log EC_{50})+((1/\text{Hill Slope})\times\log(80/(100-80))))}$$

D11-FxxLF and Tb antibody were premixed in light protecting vials prior to use. A final concentration of DTT 5 mM was used in the assay buffer in order to prevent protein degradation. All plates (agonist and antagonist mode) were incubated between 2 and 4 hours at room temperature protected from light prior to TR-FRET measurement. $IC_{50}$ values were determined by testing each ligand at concentrations ranging from 100 μM to 45 μM using two fold and three fold dilutions to generate a 12 point dose response curve. Data was fitted using the sigmoidal dose response (variable slope) available from Graphpad Prism 5.

$$Y=\text{Bottom}+(\text{Top-Bottom})/(1+10^{((\log IC_{50}-X)*\text{Hill-Slope})})$$

Z' factor for these assays was >0.5 as calculated by the equation provided by Zhang et al. [Zhang J H, Chung T D, Oldenburg K R (1999) A Simple Statistical Parameter for Use in Evaluation and Validation of High Throughput Screening Assays. *J Biomol Screen* 4:67-73].

$$Z-\text{factor}=1-\frac{3\times(\sigma_p+\sigma_n)}{|\mu_p-\mu_n|}$$

In line with the assay protocol, a known agonist, dihydrotestosterone (DHT, cat no. A8380, Sigma) and a known antagonist, cyproterone acetate (cat no. C3412, Sigma), were used as controls in the assay. A control with no AR-LBD present was included to account for diffusion enhanced FRET or ligand-independent coactivator recruitment. A negative control with 2×DMSO was present to account for any solvent vehicle effects.

The same procedure was used for AR T877A (Invitrogen cat no. PV4667), PR (Invitrogen cat no. PV4666), ER-α (Invitrogen cat no. PV4544), ER-β (Invitrogen cat no. PV4541) and GR (Invitrogen cat no. PV4683). The assay was adapted to exclude possible non-specific aggregation mechanism of inhibition by adding very low concentration of detergent Triton X-100 (0.001%) to the assay buffer following the Shoichet review guidelines [Shoichet BK (2006) Screening in a spirit haunted world. *Drug Discov Today* 11:607-615].

Fluorescence Polarisation (FP)

PolarScreen Androgen Receptor Competitor Assay Kit Green (Invitrogen, cat no. P3018) was used to investigate the binding of the test compound to the LBP site, occupied by a high affinity ligand (Fluormone).

100× test compound solutions in DMSO were diluted in AR green buffer (Invitrogen) to achieve 2× concentrations and placed in a 384 well plate (Corning, cat no. 3576) with 40 µl volume capacity. AR-LBD was supplemented with 5 mM DTT to prevent protein degradation. AR-LBD and Fluormone (2×) mix are prepared separately and then added to each compound dilution to achieve a final concentration LBD-fluormone of 50 nM and 2 nM respectively. Plates were incubated protected from light for at least 4 hours. Controls included a maximum mP positive control, which consists of the AR-LBD and fluormone mix (2×), and a minimum mP control, containing only Fluormone (2×). A vehicle control was added to account for DMSO effect, and a blank control containing buffer only. Fluorescence polarization was measured with PHERAstar equipment (BMG LabTech) using an optic module with excitation at 485 nm and emission at 530 nm.

Cell Culture

LNCaP cells (androgen-dependent), PC-3 (androgen-independent) and PWR-1E (normal prostatic epithelia) were cultured in RPMI-1640 Glutamax (Invitrogen), F12K (Invitrogen) and K-SFM media (Invitrogen). The first two were supplemented with 10% Fetal Bovine Serum (FBS), penicillin (100 units/ml), steptomyicin (100 µg/ml). K-SFM was supplemented with 5 ng/ml Epidermal Growth Factor (EGF) and 0.05 mg/ml Bovine Pituitary Extract (BPE). Cells were propagated at 1:3 or 1:6 dilutions at 37° C. in 5% $CO_2$.

Cell Viability and Cell Proliferation Assays

For cell viability (end point) assays LNCaP, PC-3 and PWR-1E cells were seeded at $2.5*10^4$/ml density in 200 µl volume of a 96-well plate in triplicate and incubated for 24 hours prior testing. Test compounds were included at different concentrations to achieve a final concentration of 0.5% DMSO in each well. Effect of 0.5% DMSO on cell-viability was also evaluated. Cell viability was assessed after 24 hours of treatment using 10% Alamar Blue reagent (Invitrogen) for each well. Cell viability was monitored by the reduction of resazurin, a blue, cell-permeable and non-toxic compound, to resorufin, a red and highly fluorescent product. Viable cells continuously convert resazurin to resorufin, increasing the overall colour and fluorescence of the media surrounding cells. Fluorescence intensity can be quantitatively determined with a fluorescence microplate reader at excitation/emission 544 nm/590 nm (Spectramax Gemini). For hormone dependent cell proliferation assays in androgen deprived LNCaP cells, cells were seeded at $2*10^4$ cells/ml in a 24-well plate in triplicate. Cells were plated in phenol red free RPMI Glutamax (Invitrogen) supplemented with 10% charcoal-stripped FBS to deplete endogenous steroids 48 hours prior the assay as described in previous reports. Optimal condition for the treatment was found to be 5 days and the concentration of DHT included to stimulate the cells was 0.1 nM. Cells were treated with different concentrations of test compounds with or without 0.1 nM DHT to achieve a final concentration of 0.1% DMSO in each well. A control for the vehicle was included to ensure no effect on viability could be detected. Media and treatments were replaced every second day, after washing the cells twice with 1×PBS. Supernatants were collected after five days for secreted PSA levels evaluation and cell proliferation was assessed for the same plate using Alamar Blue in order to exclude non-specific effects due to toxicity issues.

Prostate Specific Antigen (PSA) ELISA

Secreted levels of prostate specific antigen were evaluated with a commercially available kit (Quantikine Human Kallikrein 3/PSA Immunoassay, R&D systems). The assay was performed following manufacturer's guidelines. In brief, 50 µl of standards and cell culture samples were added to pre-coated wells containing assay diluent RD1W (R&D systems) and incubated for two hours at room temperature. Unbound material was washed several times and 200 µl of Horseradish Peroxidase (HRP) labeled PSA conjugate antibody was added to each well and further incubated for two hours at room temperature. Wells were washed and treated with colored substrate (Tetramethylbenzidine) for an additional 30 minutes, after which 50 µl of stop solution (Sulphuric Acid 2N) was added per well and absorbance (450 nm with correction at 540 nm) was read with a plate reader within 30 minutes (Versamax).

The invention claimed is:

1. A method of treating prostate cancer comprising administering to a patient in need thereof a compound of general formula (I), a tautomer thereof, a pharmaceutically acceptable salt thereof, or a solvate thereof,

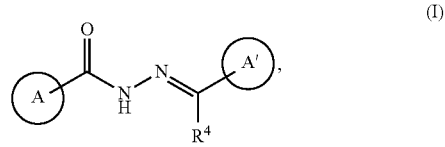

wherein A is selected from the group consisting of:

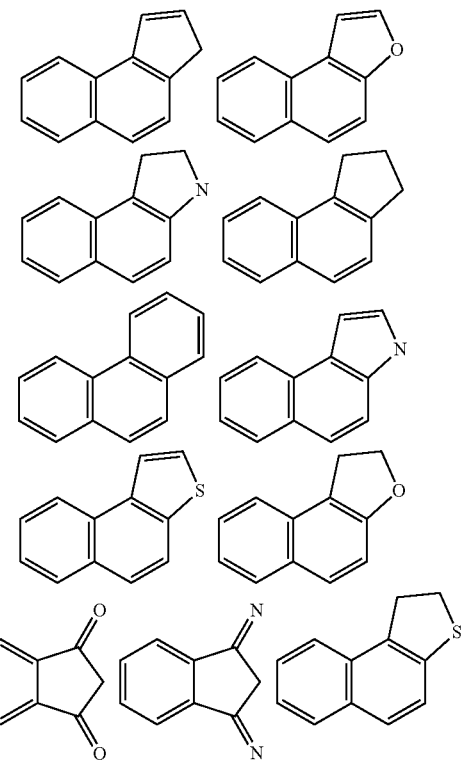

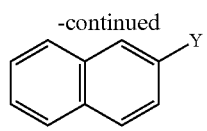

wherein A' is selected from the group consisting of:

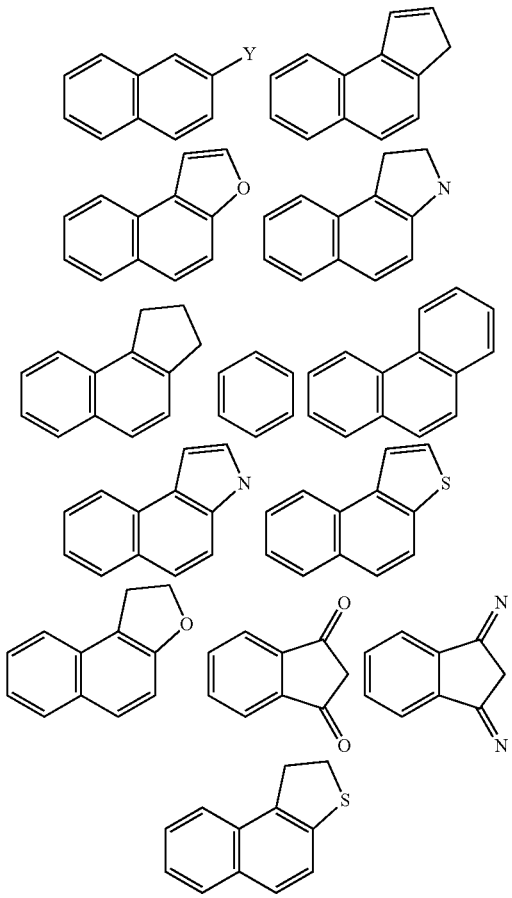

wherein at least one of A or A' is optionally substituted one or more times with at least one of $C_1$-$C_{10}$ alkyl, C(=O)H, C(=O)OH, C(=O)$OR^1$, C(=O)$NH_2$, C(=O)$NHR^1$, C(=O)$NR^1R^2$, C(=O)$R^1$, $CH_2F$, $CHF_2$, $CF_3$, C≡N, OH, $OR^1$, OC(=O)$R^1$, OC(=O)$OR^1$, OC(=O)$NH_2$, OC(=O)$NHR^1$, OC(=O)$NR^1R^2$, $NH_2$, $NHR^1$, $NR^1R^2$, N(H)C(=O)$R^1$, N($R^1$)C(=O)$R^2$, N(H)C(=O)$OR^1$, N($R^1$)C(=O)$OR^2$, N(H)C(=O)$NH_2$, N($R^1$)C(=O)$NH_2$, N(H)C(=O)$NHR^1$, N($R^1$)C(=O)$NHR^2$, N(H)C(=O)$NR^1R^2$, N($R^1$)C(=O)$NR^2R^3$, $NO_2$, SH, $SR^1$, S(=O)$R^1$, S(=O)$_2R^1$, $SO_3H$, OP(O)(OH)(OH), OP(O)(OH)(OR'), OP(O)($OR^1$)($OR^2$), H, Hal, $CH_2Hal$; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I, and wherein $R^1$, $R^2$ and $R^3$ are the same or different and are independently selected from the group consisting of $C_1$-$C_{20}$ aliphatic, $C_3$-$C_{20}$ cycloaliphatic and combinations thereof;

wherein Y is OH, SH or $NH_2$; and
$R^4$ is H or methyl;
with the proviso that the compound is not 3-hydroxy-N'-(4-hydroxy-3,5-dimethoxybenzylidene)-2-naphthohydrazide (MDG489), N'-(3-methoxybenzylidene)naphtho[2,1-b]furan-2-carbohydrazide (MDG505), 3-hydroxy-N'-(2-hydroxy-3-chlorobenzylidene)-2-naphthohydrazide (MDG618), 3-hydroxy-N'-[(1E)-1-(2-hydroxy-5-chlorophenyl)ethylidene]-2-naphthohydrazide (MDG621) and 3-hydroxy-N'-benzylidene-2-naphthohydrazide (MDG628).

2. The method of claim 1, wherein A is selected from the group consisting of:

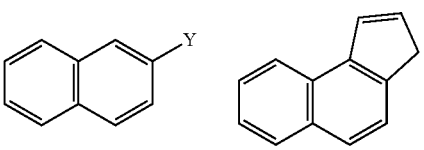

wherein A is optionally substituted one or more times with at least one of $C_1$-$C_{10}$ alkyl, C(=O)H, C(=O)OH, C(=O)$OR^1$, C(=O)$NH_2$, C(=O)$NHR^1$, C(=O)$NR^1R^2$, C(=O)$R^1$, OH, $OR^1$, OC(=O)$R^1$, OC(=O)$OR^1$, OC(=O)$NH_2$, OC(=O)$NHR^1$, OC(=O)$NR^1R^2$, $NH_2$, $NHR^1$, $NR^1R^2$, N(H)C(=O)$R^1$, N($R^1$)C(=O)$R^2$, N(H)C(=O)$OR^1$, N($R^1$)C(=O)$OR^2$, N(H)C(=O)$NH_2$, N($R^1$)C(=O)$NH_2$, N(H)C(=O)$NHR^1$, N($R^1$)C(=O)$NHR^2$, N(H)C(=O)$NR^1R^2$, N(R1)C(=O)$NR^2R^3$, $NO_2$, SH, $SR^1$, S(=O)$R^1$, S(=O)$_2R^1$, $SO_3H$, H, Hal, $CH_2Hal$; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I, wherein $R^1$, $R^2$ and $R^3$ are the same or different and are independently selected from the group consisting of $C_1$-$C_{20}$ aliphatic, $C_3$-$C_{20}$ cycloaliphatic and combinations thereof.

3. The method of claim 1, wherein A is selected from the group consisting of:

91

-continued

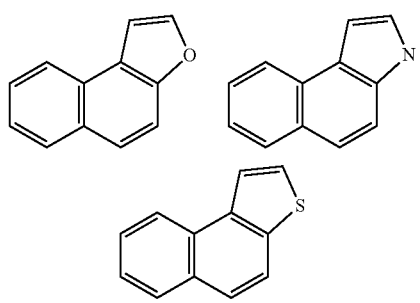

wherein A is optionally substituted one or more times with at least one of $C_1$-$C_6$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from $C_1$-$C_6$ aliphatic and combinations thereof.

4. The method of claim 1, wherein A is selected from the group consisting of:

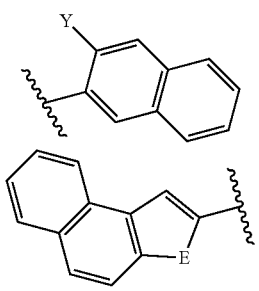

wherein Y is —OH, —SH or —NH$_2$, E is O, S or NH.

5. The method of claim 1, wherein A is selected from the group consisting of:

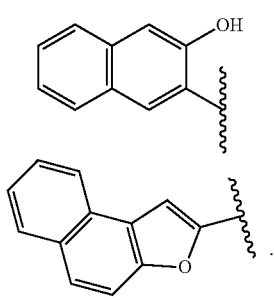

6. The method of claim 1, wherein A' is selected from the group consisting of:

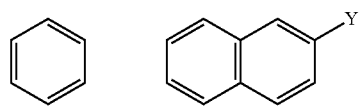

92

-continued

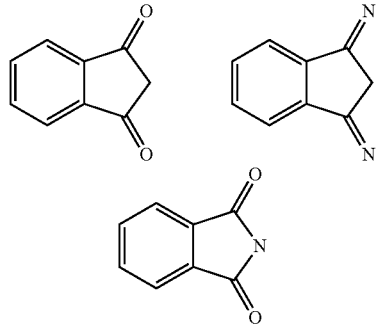

wherein A' is optionally substituted one or more times with at least one of $C_1$-$C_{10}$ alkyl, C(=O)OH, C(=O)OR$^1$, C(=O)R$^1$, OH, OR$^1$, OC(=O)OR$^1$, NH$_2$, NHR$^1$, NR$^1$R$^2$, NO$_2$, SH, SR$^1$, S(=O)R$^1$, S(=O)$_2$R$^1$, SO$_3$H, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, wherein R$^1$ and R$^2$ are the same or different and are independently selected from the group consisting of $C_1$-$C_{20}$ aliphatic, $C_3$-$C_{20}$ cycloaliphatic and combinations thereof.

7. The method of claim 1, wherein A' is selected from the group consisting of:

wherein
Y is selected from OH, SH, and NH$_2$;
X is selected from OH, OCH$_3$, COOH, COOCH$_3$, NO$_2$, Cl, Br, I and F;
Z is selected from CH and N;
E is selected from O, S, and NH;
R$^5$ and R$^6$ are the same or different and are $C_1$-$C_5$ alkyl; and
R$^7$ is $C_3$-$C_5$ straight chain alkyl.

8. The method of claim 1, wherein A is selected from the group consisting of:

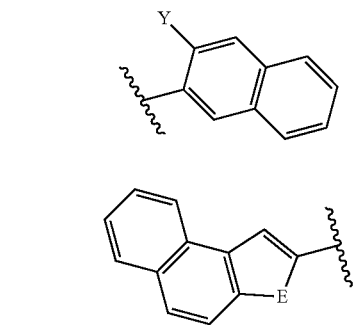

wherein Y is —OH, —SH or —NH$_2$, E is O, S or NH; and wherein A' is selected from the group consisting of:

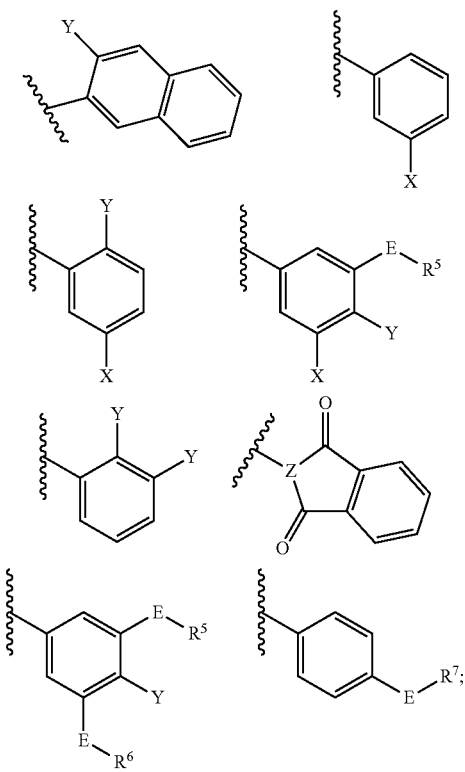

wherein
- Y is selected from OH, SH, and NH$_2$;
- X is selected from OH, OCH$_3$, COOH, COOCH$_3$, NO$_2$, Cl, Br, I and F;
- Z is selected from CH and N;
- E is selected from O, S, and NH;
- R$^5$ and R$^6$ are the same or different and are C$_1$-C$_5$ alkyl; and
- R$^7$ is C$_3$-C$_5$ straight chain alkyl.

9. The method of claim 1, wherein A' is selected from the group consisting of:

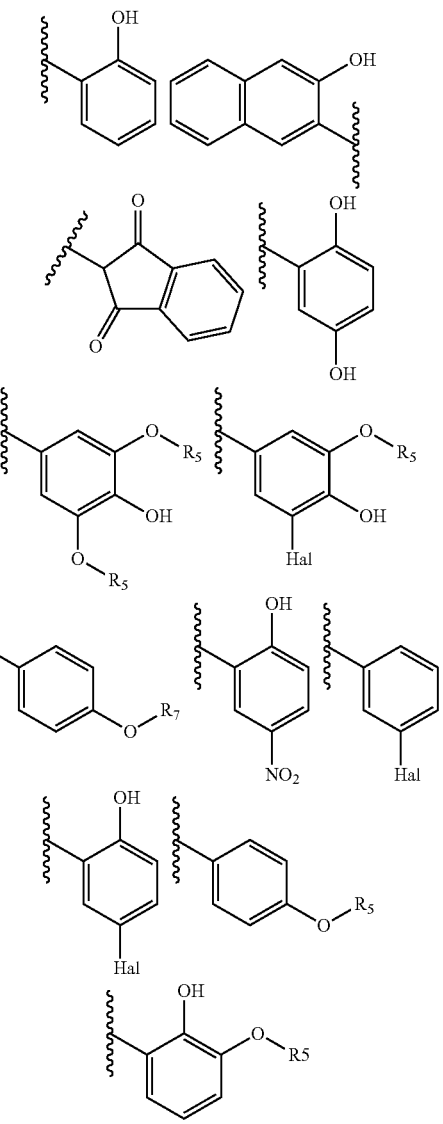

wherein Hal is Cl, Br, I or F; R$^5$ is the same or different and are C$_1$-C$_5$ alkyl; and
R$^7$ is C$_3$-C$_5$ straight chain alkyl.

10. The method of claim 1, wherein A' is selected from the group consisting of:

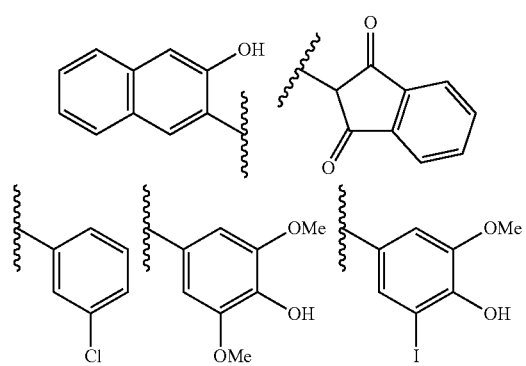

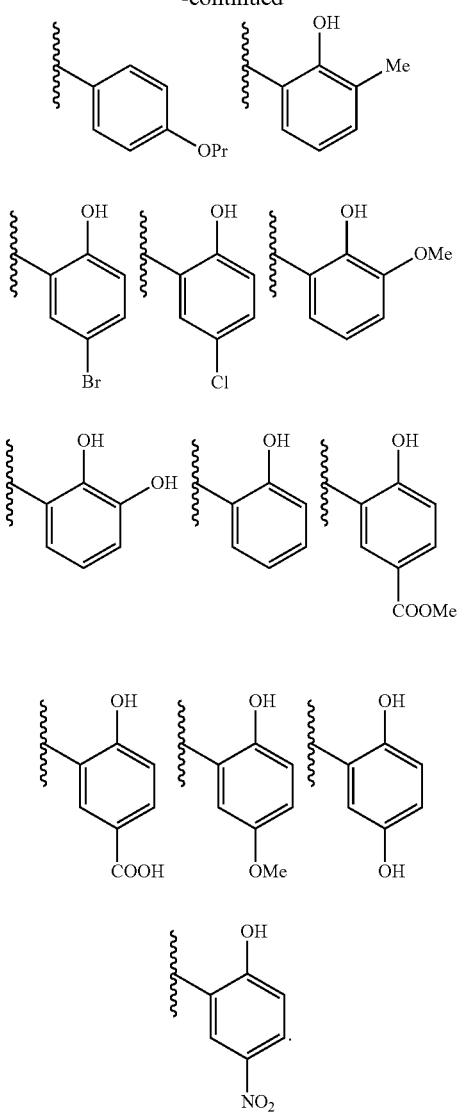
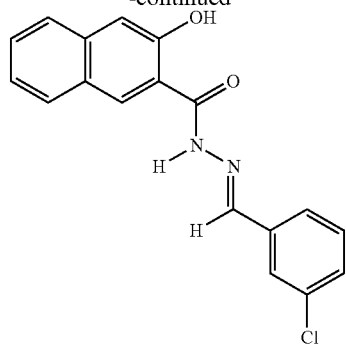
MDG491
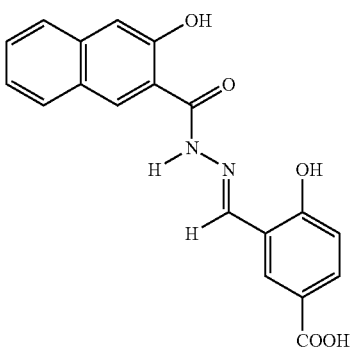
MDG630
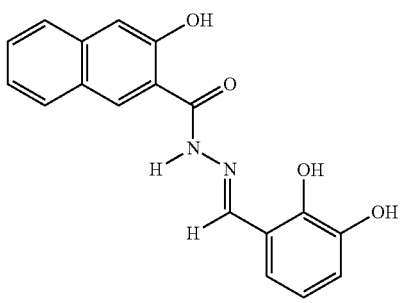
MDG173
11. The method of claim 1, wherein the compound is selected from the group consisting of:
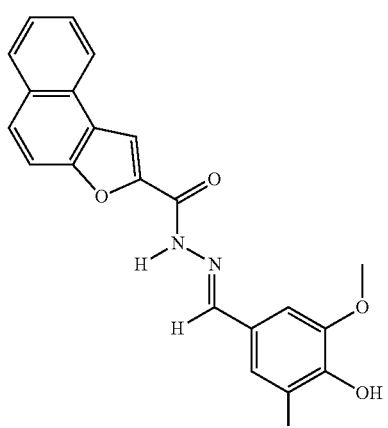
MDG15
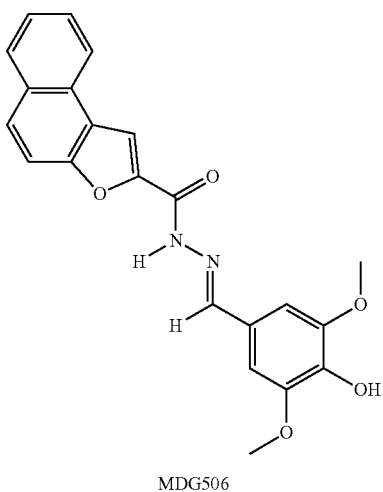
MDG506

-continued
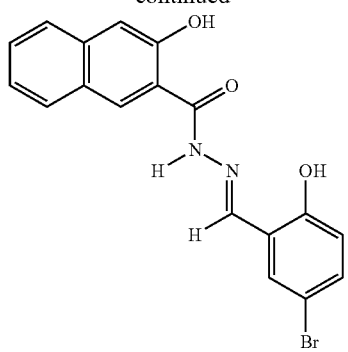
MDG292
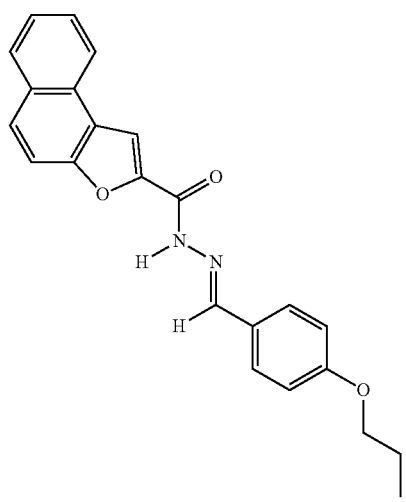
MDG508
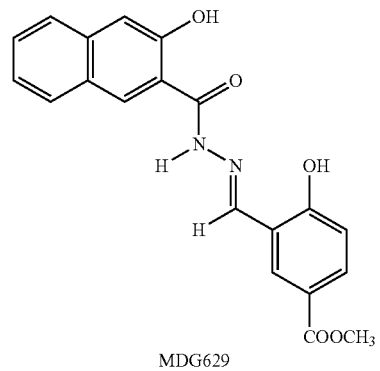
MDG629
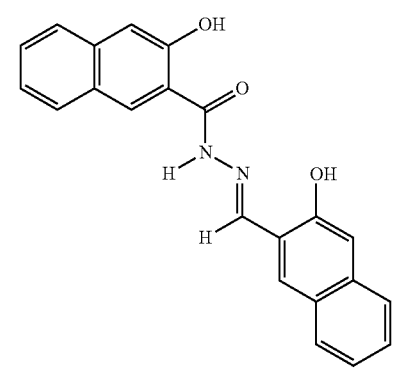
MDG483
-continued
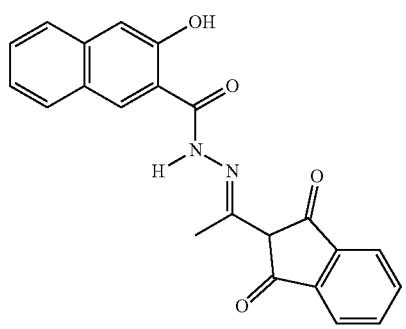
MDG603
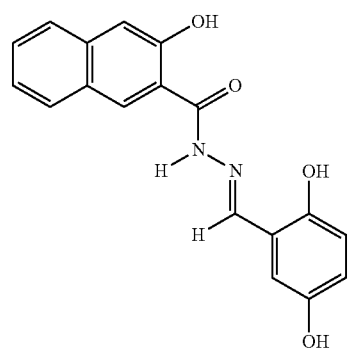
MDG611
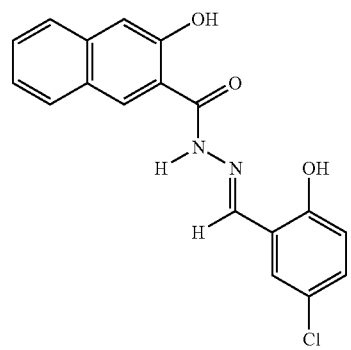
MDG605
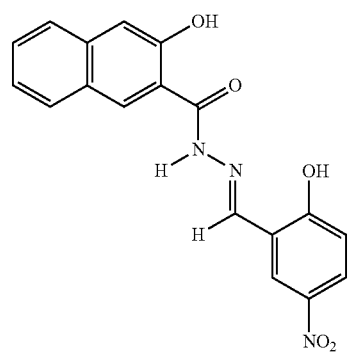
MDG614

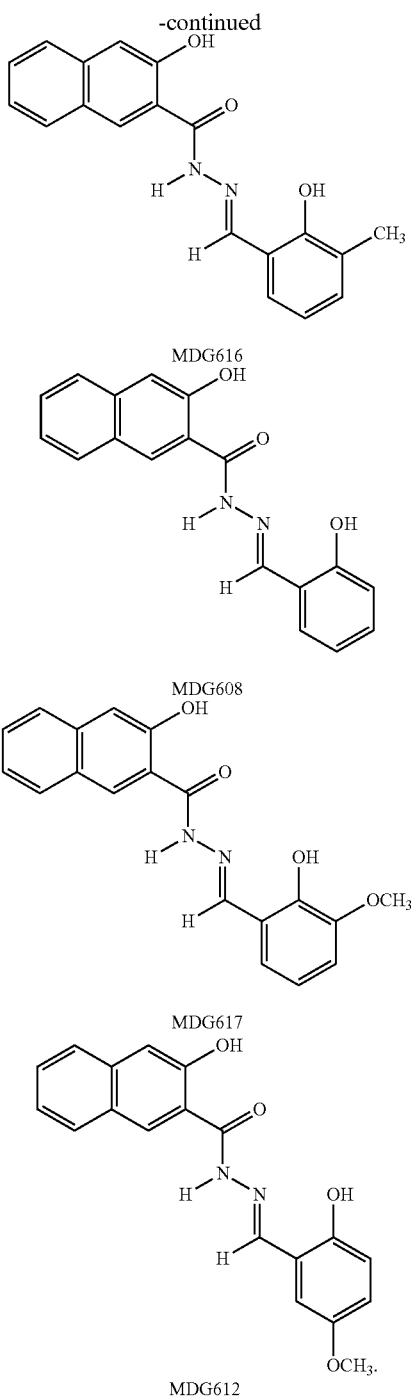

MDG616

MDG608

MDG617

MDG612

12. The method of claim 1, wherein A is:

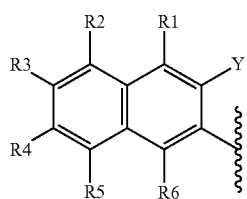

wherein Y is selected from OH, SH, and NH$_2$, each of R1-R6 are the same or different and are selected from the group consisting of C$_1$-C$_6$ alkyl, SH, NH$_2$, NR$_2$, COOH, COOR, CH$_2$Hal, H, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I; and wherein A' is selected from the group consisting of:

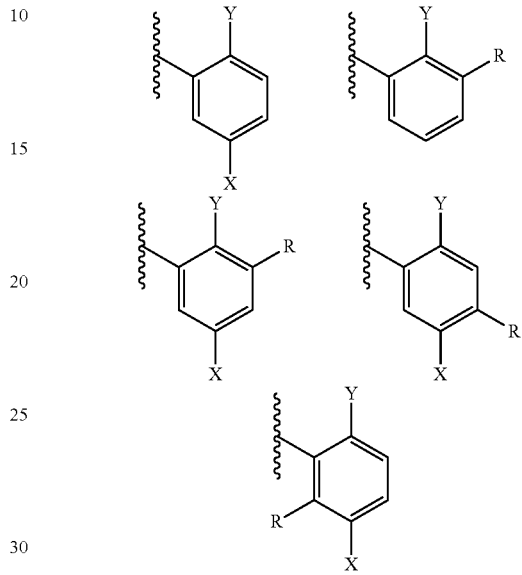

wherein
Y is selected from H, OH, SH, and NH$_2$;
X is selected from H, Hal, OH, OCH$_3$, COOCH$_3$, COOH, COOR, NO$_2$, wherein Hal is selected from Cl, I and F; and
R is selected from H, OH, C$_1$-C$_6$ alkyl, SH, NH$_2$, NR$_2$, COOH, COOR, CH$_2$Hal, Hal, CH$_2$Hal; CH$_2$OH, CH$_2$SH, CH$_2$NH$_2$, CH$_2$NH$_2$, CH$_2$COOH, CH$_2$COOR$^1$, NHC(NH)NH$_2$, wherein Hal is Cl, Br, F, and I, with the proviso that the compound is not 2-Naphthalenecarboxylic acid, 3-hydroxy-, 2-[(2,4-dihydroxyphenyl)methylene]hydrazide; 2-Naphthalenecarboxylic acid, 3-hydroxy-, 2-[(2,3-dihydroxyphenyl)methylene]hydrazide; 2-Naphthalenecarboxylic acid, 3-hydroxy-, 2-[(2,4,6-trihydroxyphenyl)methylene]hydrazide; 2-Naphthalenecarboxylic acid, 3-hydroxy-, 2-[(2,3,4-trihydroxyphenyl)methylene]hydrazide; 2-Naphthalenecarboxylic acid, 3-hydroxy-, 2-[[4-(diethylamino)-2-hydroxyphenyl]methylene]hydrazide; 2-Naphthalenecarboxylic acid, 3-hydroxy-, 2-[(5-bromo-2-hydroxy-3-iodophenyl)methylene]hydrazide; 2-Naphthalenecarboxylic acid, 3-hydroxy-, 2-[(3-bromo-2-hydroxy-5-nitrophenyl)methylene]hydrazide; 2-Naphthalenecarboxylic acid, 3-hydroxy-, 2-[(5-bromo-3-chloro-2-hydroxyphenyl)methylene]hydrazide; 2-Naphthalenecarboxylic acid, 3-hydroxy-, 2-[(2-hydroxy-3,5-diiodophenyl)methylene]hydrazide; 2-Naphthalenecarboxylic acid, 3-hydroxy-, 2-[(3-bromo-5-chloro-2-hydroxyphenyl)methylene]hydrazide; 2-Naphthalenecarboxylic acid, 3-hydroxy-, 2-[(3,5-dibromo-2-hydroxyphenyl)methylene]hydrazide; 2-Naphthalenecarboxylic acid, 3-hydroxy-, 2-[(3,5-dichloro-2-hydroxyphenyl)methylene]hydrazide; 2-Naphthalenecarboxylic acid, 3-hydroxy-, 2-[(2-hydroxy-3-nitrophenyl)methylene]hydrazide; 2-Naphthalenecarboxylic acid, 3-hydroxy-, 2-[(2-hydroxy-3,5-dinitrophenyl)methylene]hydrazide; or 2-Naphthalenecarboxylic acid, 3-hydroxy-, 2-[(5-chloro-2-hydroxy-3-nitrophenyl)methylene]hydrazide.

13. The method of claim 12, wherein A is:

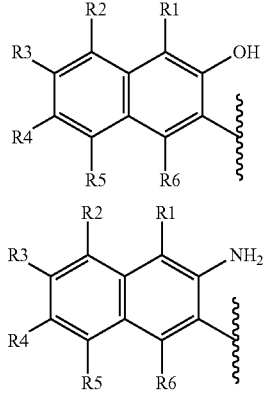

wherein each of $R^1$-$R^6$ are the same or different and are selected from the group consisting of $C_1$-$C_6$ alkyl, SH, $NH_2$, $NR_2$, COOH, COOR, $CH_2Hal$, H, Hal, $CH_2Hal$; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I; and wherein A' is selected from the group consisting of:

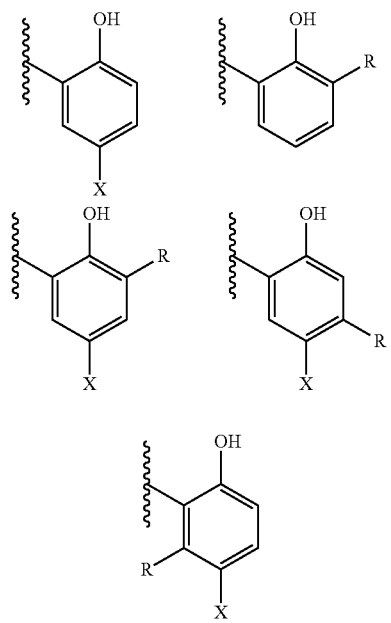

wherein
X is selected from H, Hal, OH, $OCH_3$, $COOCH_3$, COOH, COOR, $NO_2$, wherein Hal is selected from Cl, I and F; and
R is selected from H, OH, $C_1$-$C_6$ alkyl, SH, $NH_2$, $NR_2$, COOH, COOR, $CH_2Hal$, Hal, $CH_2Hal$; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I.

14. The method of claim 12, wherein A is:

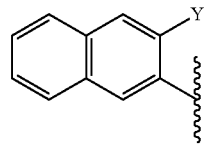

wherein Y is selected from OH, SH, and $NH_2$; and
wherein A' is selected from the group consisting of:

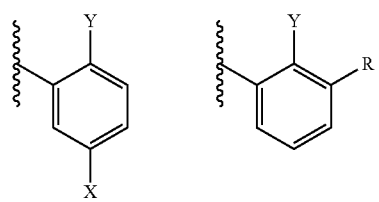

wherein
Y is selected from OH, SH, and $NH_2$;
X is selected from OH, COOH, COOR, $NO_2$, Cl, I and F; and
R is $C_1$-$C_6$ alkyl.

15. The method of claim 1, wherein the compound of formula (I) is selected from the group consisting of:

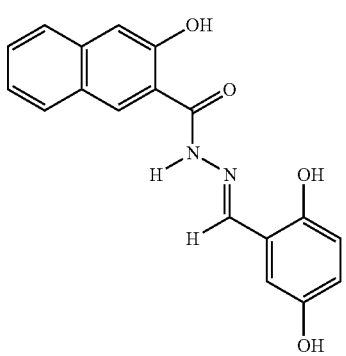
MDG611

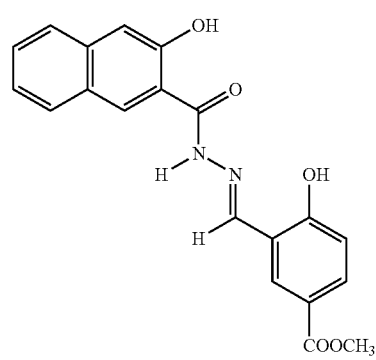
MDG629

16. A compound selected from the group consisting of:
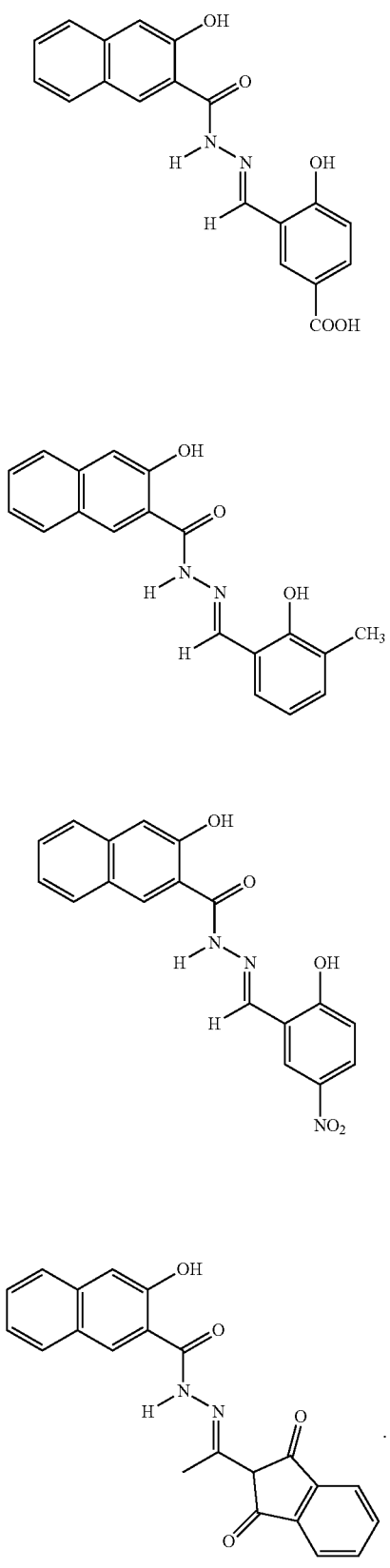

-continued

MDG603

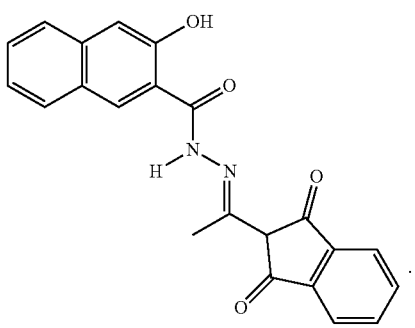

17. A pharmaceutical composition comprising a compound according to claim 16, a tautomer thereof, a pharmaceutically acceptable salt thereof, or a solvate thereof, and a pharmaceutically acceptable excipient.

18. A method of treating prostate cancer comprising administering to a patient in need thereof a composition comprising a therapeutically effective amount of a compound of general formula (I), a tautomer thereof, a pharmaceutically acceptable salt thereof, or a solvate thereof,

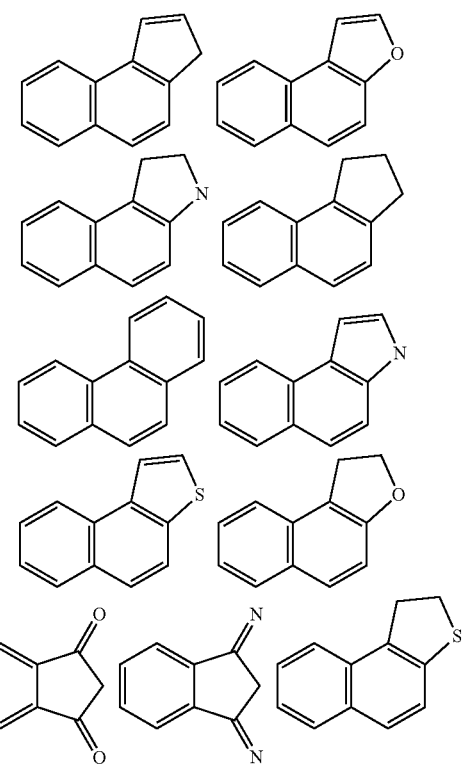

(I)

wherein A is selected from the group consisting of:

-continued

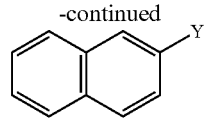

wherein A' is selected from the group consisting of:

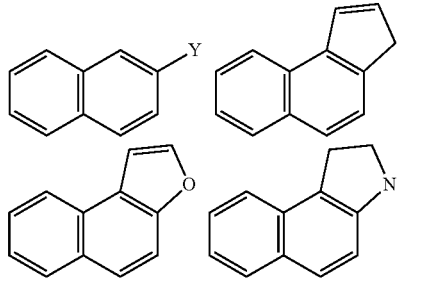

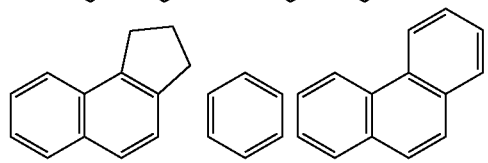

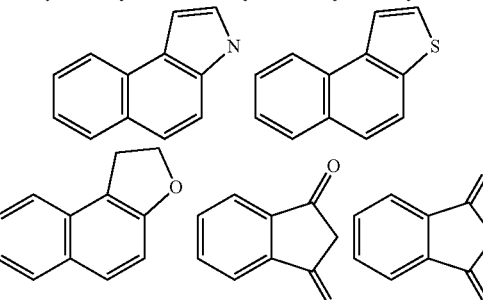

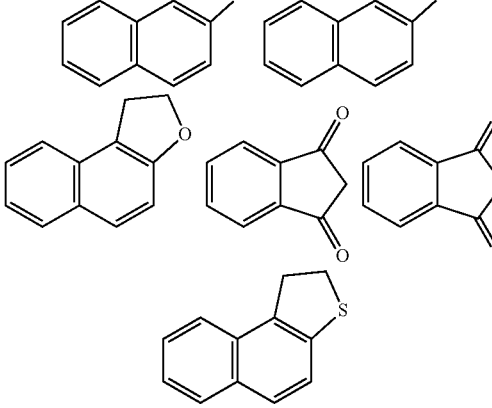

wherein at least one of A or A' is optionally substituted one or more times with at least one of $C_1$-$C_{10}$ alkyl, $C(=O)H$, $C(=O)OH$, $C(=O)OR^1$, $C(=O)NH_2$, $C(=O)NHR^1$, $C(=O)NR^1R^2$, $C(=O)R^1$, $CH_2F$, $CHF_2$, $CF_3$, $C\equiv N$, OH, $OR^1$, $OC(=O)R^1$, $OC(=O)OR^1$, $OC(=O)NH_2$, $OC(=O)NHR^1$, $OC(=O)NR^1R^2$, $NH_2$, $NHR^1$, $NR^1R^2$, $N(H)C(=O)R^1$, $N(R^1)C(=O)R^2$, $N(H)C(=O)OR^1$, $N(R^1)C(=O)OR^2$, $N(H)C(=O)NH_2$, $N(R^1)C(=O)NH_2$, $N(H)C(=O)NHR^1$, $N(R^1)C(=O)NHR^2$, $N(H)C(=O)NR^1R^2$, $N(R^1)C(=O)NR^2R^3$, $NO_2$, SH, $SR^1$, $S(=O)R^1$, $S(=O)_2R^1$, $SO_3H$, $OP(O)(OH)(OH)$, $OP(O)(OH)(OR^1)$, $OP(O)(OR^1)(OR^2)$, H, Hal, $CH_2$Hal; $CH_2OH$, $CH_2SH$, $CH_2NH_2$, $CH_2NH_2$, $CH_2COOH$, $CH_2COOR^1$, $NHC(NH)NH_2$, wherein Hal is Cl, Br, F, and I, and wherein $R^1$, $R^2$ and $R^3$ are the same or different and are independently selected from the group consisting of $C_1$-$C_{20}$ aliphatic, $C_3$-$C_{20}$ cycloaliphatic and combinations thereof;

wherein Y is OH, SH or $NH_2$; and $R^4$ is H or methyl;

with the proviso that the compound is not 3-hydroxy-N-(4-hydroxy-3,5-dimethoxybenzylidene)-2-naphthohydrazide (MDG489), N'-(3-methoxybenzylidene)naphtho[2,1-b]furan-2-carbohydrazide (MDG505), 3-hydroxy-N'-(2-hydroxy-3-chlorobenzylidene)-2-naphthohydrazide (MDG618), 3-hydroxy-N'-[(1E)-1-(2-hydroxy-5-chlorophenyl)ethylidene]-2-naphthohydrazide (MDG621) and 3-hydroxy-N'-benzylidene-2-naphthohydrazide (MDG628).

* * * * *